US006271014B1

(12) United States Patent
de Saint-Vis et al.

(10) Patent No.: US 6,271,014 B1
(45) Date of Patent: Aug. 7, 2001

(54) MAMMALIAN PROTEINASES; RELATED REAGENTS AND METHODS

(75) Inventors: Blandine Marie de Saint-Vis, Lyon; François Fossiez, Marcy l'Etoile; Christophe Caux, Lyon; Serge J. E. Lebecque, Civrieux d'Azergue, all of (FR)

(73) Assignee: Schering-Plough, Levallois-Perret (FR)

( * ) Notice: Subject to any disclaimer, the term of this patent is extended or adjusted under 35 U.S.C. 154(b) by 0 days.

(21) Appl. No.: 09/211,704

(22) Filed: Dec. 14, 1998

Related U.S. Application Data

(63) Continuation of application No. 09/005,263, filed on Jan. 9, 1998, now abandoned.

(51) Int. Cl.⁷ .............................. C12N 9/50; C12N 9/04

(52) U.S. Cl. .................... 435/226; 435/189; 435/219; 530/350; 536/23.2

(58) Field of Search ................................. 530/350, 23.2; 435/219, 226, 184

(56) References Cited

FOREIGN PATENT DOCUMENTS

WO 95/25171    9/1995    (WO).

OTHER PUBLICATIONS

Ngo et al., "Computational Complexity, Protein Structure Prediction, and the Levinthal Paradox," in The Protein Folding Problem and Tertiary Structure Prediction, Merz, Jr., Ed., Birkhauser Boston, pp. 492–494, 1994.*
Thornton et al., "Protein engineering," Cur. Opinion Biotech., vol. 6, No. 4, pp. 367–369, Aug. 1995.*
Rudinger, p. 6 of Peptide Hormones, Parsons, Ed., University Park Press, Jun. 1976.*
Carol B. Bausbaum & Zena Werb, Current Opinion in Cell Biology, 8:731–738, 1996. "Focalized proteolysis: spatial and temporal regulation of extracellular matrix degradation at the cell surface".
Peter D. Brown, Medical Oncology, 14:1–10, Mar. 1997. "Matrix metalloproteinase inhibitors in the treatment of cancer".
Alain Bernot, et al., Genomics, 50(2):147–160, Jun. 1, 1998. "A Transcriptional Map of the FMF Region".
A. Bernot, et al., GenBank, Accession Number AJ003147, Jan.22, 1998 & Dec. 11, 1998. Definition: "Homo sapiens complete genomic sequence between D16S3070 and D16S3275, containing Familial Mediterranean Fever gene disease."
Ann F. Chambers & Lynn M. Matrisian, J. Natl. Cancer Inst., 89(7):1260–1270, Sep. 3, 1997. "Changing Views of the Role of Matrix Metalloproteinases in Metastasis".
Wen–Tien Chen, Enzyme Protein, 49(1–3):59–71, 1996. "Proteases Associated with Invadopodia, and Their Role in Degradation of Extracellular Matrix".

Lisa M. Coussens & Zena Werb, Chem. Biol., 3:895–904, Nov. 1996. "Matrix metalloproteinases and the development of cancer".
Liliana Guedez, et al., Critical Reviews in Oncogenisis, 7(3&4):205–225, 1996. "The Role of Metalloproteinases and Their Inhibitors in Hematological Disorders".
T. Hudson, GenBank, Accession Number G22642, May 31, 1996. Definition: "human STS WI–15307."
K. Matsubara, et al., Result 1 from sequence search using Seq ID NO:1 as the query and disignated by Accession Number T20225, Jul. 24, 1996. Definition: "Human gene signature HUMGS01371".
Chris G.F. Mueller, et al., J. Exp. Med., 186(5):655–663, Aug. 29, 1997. "Polymerase Chain Reaction Selects a Novel Disintegrin Proteinase from CD40–Activated Germinal Center Dendritic Cells".
Hideaki Nagase, Zinc Metalloproteases in Health and Disease, Ed. N.M. Hooper, (Taylor and Francis: London, 1996) Chapter 7, pp. 153–204. "Matrix metalloproteinases".
F. Nollet, et al., GenBank, Accession No.: X89578, Feb. 6, 1997. Definition: "H. sapiens DNA for beta–catenin gene exon 1".
K. Okubo, et al., GenBank, Accession No.: D20397, Jul. 30, 1996. Definition: "HUMGS01371 Human promyelocyte Homo sapiens cDNA clone pm2867 3', mRNA sequence."
S.L. Parsons, et al., British Journal of Surgery, 84:160–166, Feb. 1997. "Matrix Metalloproteinases".
Xose S. Puente, et al., Cancer Research, 56(5):944–949, Mar. 1, 1996. "Molecular Cloning of a Novel Membrane–type Matrix Metalloproteinase from a Human Breast Carcinoma".
J.M. Ray, et al., Eur. Respir. J., 7(11):2062–2072, Nov. 1994. "The role of matrix metalloproteases and their inhibitors in tumor invasion, metastasis and angiogenesis".
H.H. Sato, et al., GenBank, Accession No.: D86331, Jul. 12, 1996. Definition: "Human MT2–MMP gene for matrix metalloprotein, complete cds".
D.C. Talbot & P.D. Brown, Eur. J. Cancer, 32A(14):2528–2533, Dec. 1996. "Experimental and Clinical Studies on the Use of Matrix Metalloproteinase Inhibitors for the Treatment of Cancer".
Bert E. Vallee & Davis S. Auld, Proc. Natl. Acad. Sci. USA, 87:220–224, Jan. 1990. "Active–site zinc ligands and activated $H_2O$ of zinc enzymes".
H. Will, et al., GenBank, Accession No.: A46722, Mar. 7, 1997. Definition: "Sequence 5 from Patent WO9525171".

(List continued on next page.)

Primary Examiner—Rebecca E. Prouty
Assistant Examiner—Richard Hutson
(74) Attorney, Agent, or Firm—Karen B. Dow; Hugh Wang; Edwin P. Ching

(57) ABSTRACT

Nucleic acids encoding various proteases, from a mammal, reagents related thereto, including specific antibodies, and purified proteins are described. Methods of using said reagents and related diagnostic kits are also provided.

13 Claims, No Drawings

OTHER PUBLICATIONS

H. Will, et al., *GenBank*, Accession No.: Z48482, Aug. 24, 1995. Definition: "H.sapiens mRNA for membrane-type matrix metalloproteinase 2".

Slawomir M. Wojtowicz–Praga, et al., *Investigational New Drugs*, 15:61–75, 1997. "Matrix metalloproteinase inhibitors".

* cited by examiner

MAMMALIAN PROTEINASES; RELATED REAGENTS AND METHODS

This filing is a continuation application of commonly assigned, U.S. Pat. No. 09/005,263, filed Jan. 9, 1998, now abandoned, which is incorporated herein by reference.

FIELD OF THE INVENTION

The present invention contemplates compositions related to proteins from animals, e.g., mammals, which function as proteinases. In particular, it provides nucleic acids which encode the proteinases, antibodies to, and proteins which exhibit biological functions, e.g., capacity to degrade proteinaceous substrates.

BACKGROUND OF THE INVENTION

The proteases are a very broad group of enzymes which carry out an enzymatic function of hydrolyzing a peptide bond. See, e.g., Beynon (ed. 1989) *Proteolytic Enzymes: A Practical Approach* IRL Press, Oxford; *Methods in Enzymology* vols. 244 and 248. Within the group, there is a wide range of substrate specificities for the amino acids adjacent the cleavage sites. Proteases are typically categorized on the basis of their catalytic mechanisms, e.g., based upon studies of their active sites, or by the effects of pH. Four main categories of proteases are serine proteinases, sulfhydryl proteases, acid proteases, and metalloproteases. They may also be classified according to their sites of substrate cleavage, e.g., endoproteases, amino peptidases, or carboxy peptidases.

Proteases have traditionally held a large share of the industrial enzyme market. Proteases are used in many industrial processes, including in detergents and cleaning products, e.g., to degrade protein materials such as blood and stains, in leather production, e.g., to remove hair, in baking, e.g., to break down glutens, in flavorings, e.g., soy sauce, in meat tenderizing, e.g., to break down collagen, in gelatin or food supplement production, in the textile industry, in waste treatment, and in the photographic industry. See, e.g., Gusek (1991) *Inform* 1:14–18; Zamost, et al. (1996) *J. Industrial Microbiol.* 8:71–82; James and Simpson (1996) *CRC Critical Reviews in Food Science and Nutrition* 36:437–463; Teichgraeber, et al. (1993) *Trends in Food Science and Technology* 4:145–149; Tjwan, et al. (1993) *J. Dairy Research* 60:269–286; Haard (1992) *J. Aquatic Food Product Technology* 1:17–35; van Dijk (1995) *Laundry and Cleaning News* 21:32–33; Nolte, et al. (1996) *J. Textile Institute* 87:212–226; Chikkodi, et al. (1995) *Textile Res. J.* 65:564–569; and Shih (1993) *Poultry Science* 72:1617–1620.

Matrix metalloproteinases (MMPs) are a family of enzymes whose main physiological function is degradation of the extracellular matrix. See, e.g., Parsons, et al. (1997) *Br. J. Surgery* 84:160–166. These enzymes are present in normal healthy individuals and have been shown to have an important role in processes such as wound healing (see Wolf, et al. (1992) *J. Invest. Dermatol.* 99:870–872; and Wysocki, et al. (1993) *J. Invest. Dermatol.* 101:64–68), pregnancy and parturition (see Jeffrey (1991) *Seminars Perinatol.* 15:118–126), bone resorption (see Delaisse and Vaes, pp. 290–314 in Rifkin and Gay (eds. 1992) *Biology and Physiology of the Osteoclast* CRC Press, Ratan, Fla.), and mammary involution (Talhouk, et al. (1992) *J. Cell Biol.* 118:1271–1282). See also Nagase (1996) in Hooper (ed.) *Zinc Metalloproteinases in Health and Disease* Taylor and Francis, London. A recent focus on the MMPs is on their role in certain disease states in which breakdown of the extracellular matrix is a key feature, e.g., in rheumatoid arthritis (see Harris (1990) *NEJ Med.* 322:1277–1289), periodontal disease (see Page (1991) *J. Periodont. Res.* 26:230–242), and cancer (see Brown (1997) *Medical Oncology* 14:1–10; Chambers and Matisian (1997) *J. NCI* 89:1260–1270; Yu, et al. (1997) *Drugs and Aging* 11:229–244; Yu, et al. (1997) *Clinical Pharmacology* 11:229–244; Wojtowicz-Praga, et al. (1997) *Invest. New Drugs* 15:61–75; Coussens and Werb (1996) *Chem. Biol.* 3:895–904; and Talbot and Brown (1996) *Eur. J. Cancer* 32A:2528–2533).

While there are many uses for proteases, there is always the need for a more active or specific protease under various specific conditions. Alternatively, the distribution of these gene products may be useful as markers for specific cell or tissue types. There is a need for new proteinases of differing properties, specificities, and activities.

SUMMARY OF THE INVENTION

In a search for DC restricted molecules, a novel member of the MMP family of proteolytic enzymes was identified which belongs to the Membrane-type Matrix Metalloproteinase (MT-MMP) subclass. This fifth MT-MMP proteinase, located on chromosome 16p13.3, is present in spleen, lymph node, thymus, appendix, PBL, and bone marrow, and strongly expressed by DC and weakly by granulocytes and effector T cells. Interestingly, the mRNA expression of this gene is down-regulated by CD40L activation of $CD34^+$- and monocyte-derived DC. According to its cellular expression and putative membrane localization, a role is proposed for this novel Membrane-type Matrix Metalloproteinase gene in degradation of the extracellular matrix during DC migration.

The present invention provides a binding compound comprising an antibody binding site which specifically binds to primate F06B09 protein; a nucleic acid comprising sequence encoding at least 12 amino acids of primate F06B09 protein; a substantially pure protein which is specifically recognized by the above antibody binding site; a substantially pure primate F06B09 protein or peptide thereof; and a fusion protein comprising a 30 amino acid sequence portion of primate F06B09 protein sequence.

In certain binding compound embodiments, the antibody binding site is specifically immunoreactive with a protein selected from polypeptides of SEQ ID NO: 4; is raised against a purified or recombinantly produced primate F06B09 protein; is immunoselected on a substantially purified or recombinantly produced primate F06B09 protein; is in a monoclonal antibody, Fab, or F(ab)2; is detectably labeled; is attached to a solid substrate; is from a rabbit or mouse; binds with a Kd of at least about 300 $\mu$M; is fused to another protein segment; is in a chimeric antibody; or is coupled to another chemical moiety.

The invention also provides a method of making an antigen-antibody complex, comprising a step of contacting a primate biological sample to a specific binding antibody described. In preferred embodiments, the method further includes steps to purify the antigen or antibody.

Alternative embodiments provide an antibody binding site wherein the binding site is detected in a biological sample by a method comprising the steps of contacting a binding agent having an affinity for F06B09 protein with the biological sample; incubating the binding agent with the biological sample to form a binding agent:F06B09 protein complex; and detecting the complex. In certain embodiments, the biological sample is human, and the binding agent is an antibody.

The invention also provides kits containing a composition described above and instructional material for the use of the composition; or segregation of the composition into a container. Typically, the kit is used to make a qualitative or quantitative analysis.

The invention also embraces a cell comprising an antibody described above; a cell transfected with a nucleic acid described above; or a cell comprising a fusion protein described above.

In nucleic acid embodiments, the nucleic acid may encode a polypeptide which specifically binds an antibody generated against an immunogen selected from the group consisting of the mature polypeptides of SEQ ID NO: 4. Alternatively, the nucleic acid may encode at least 12 amino acids of SEQ ID NO: 4; comprise sequence of at least about 39 nucleotides selected from protein coding portions of SEQ ID NO: 1 or 3; hybridize to SEQ ID NO: 1 or 3 under stringent wash conditions of at least 45° C. and less than about 150 mM salt; comprise sequence made by a synthetic method; be an expression vector; be detectably labeled; be attached to a solid substrate; be from human; bind with a Kd of at least about 300 $\mu$M; be fused to another nucleic acid segment; be coupled to another chemical moiety; be operably associated with promoter, ribosome binding site, or poly-A addition site; be a PCR product; be transformed into a cell, including a bacterial cell; be in a sterile composition; be capable of selectively hybridizing to a nucleic acid encoding an F06B09 protein; comprise a natural sequence; comprise a mature protein coding segment of SEQ ID NO: 1 or 3; encode proteolytically active portion of F06B09; be detected in a biological sample by a method comprising: contacting a biological sample with a nucleic acid probe capable of selectively hybridizing to said nucleic acid, incubating the nucleic acid probe with the biological sample to form a hybrid of the nucleic acid probe with complementary nucleic acid sequences present in the biological sample; and determining the extent of hybridization of the nucleic acid probe to the complementary nucleic acid sequences, including the method where the nucleic acid probe is capable of hybridizing to a nucleic acid encoding a protein selected from the group consisting of the mature polypeptides of SEQ ID NO 4.

In protein or polypeptide embodiments, the proteins may bind with a Kd of at least about 300 $\mu$M to an antibody generated against an immunogen of the polypeptides of SEQ ID NO: 4; be immunoselected on an antibody which selectively binds a polypeptide of SEQ ID NO: 4; comprise sequence of at least 12 contiguous residues of SEQ ID NO: 4; exhibit a post-translational modification pattern distinct from natural F06B09; be 3-fold or fewer substituted from natural sequence; be recombinantly produced; be denatured; have sequence of full length natural polypeptide; be detectably labeled; be attached to a solid substrate; be from human; be in a sterile composition; be fused to another protein segment; be coupled to another chemical moiety; comprise at least a fragment of at least 32 amino acid residues from a human F06B09 protein; comprise mature polypeptide sequence selected from the group consisting of SEQ ID NO 4 and 4; be a soluble protein; be a naturally occurring protein; or be a proteolytically active portion of F06B09.

The invention also provides an isolated protein which specifically binds to an antibody generated against an immunogen selected from the group consisting of the full length polypeptides of SEQ ID NO: 4. Preferably such protein binds to the antibody with a Kd of at least about 300 $\mu$M; is immunoselected on an antibody which selectively binds a polypeptide of SEQ ID NO: 4; comprises sequence of at least 12 contiguous residues of SEQ ID NO: 4; exhibits a post-translational modification pattern distinct from natural F06B09; is 3-fold or fewer substituted from natural sequence; is recombinantly produced; is denatured; has sequence of full length natural polypeptide; is detectably labeled; is attached to a solid substrate; is from human; is in a sterile composition; is fused to another protein segment; is coupled to another chemical moiety; comprises at least a fragment of at least 32 amino acid residues from a human F06B09 protein; comprises mature polypeptide sequence selected from the group consisting of SEQ ID NO 4; is a soluble protein; or comprises a proteolytic activity of F06B09.

In certain other embodiments, the invention embraces a fusion protein described above, which comprises sequence from an enzymatically active portion of SEQ ID NO: 4. Preferably such protein binds with a Kd of at least about 300 $\mu$M to an antibody generated against an immunogen having sequence of a polypeptide of SEQ ID NO. 4; is immunoselected on an antibody which selectively binds a polypeptide of SEQ ID NO: 4; comprises sequence of at least 12 contiguous residues of SEQ ID NO: 4; is recombinantly produced; is denatured; has sequence of full length natural polypeptide; is detectably labeled; is attached to a solid substrate; comprises sequence from human; is in a sterile composition; is fused to another protein segment; is coupled to another chemical moiety; comprises at least a fragment of at least 32 amino acid residues from a human F06B09 protein; comprises mature polypeptide sequence from SEQ ID NO 4; is a soluble protein; or comprises a proteolytic activity of F06B09.

The invention also provides a substantially pure protein described above which comprises a proteolytic activity of F06B09.

A method of modulating physiology or development of a cell comprising contacting said cell with said compositions is provided.

DETAILED DESCRIPTION

OUTLINE

| I. | General |
| II. | Definitions |
| III. | Nucleic Acids |
| IV. | Making F06B09 Protein |
| V. | Antibodies; binding compounds |
| | a. antibody production |
| | b. immunoassays |
| VI. | Purified F06B09 Protein |
| VII. | Physical Variants |
| VIII. | Binding Agent: F06B09 Protein Complexes |
| IX. | Functional Variants |
| X. | Uses |
| XI. | Kits |
| XII. | Substrate Identification |

I. General

Dendritic cells (DC), present in all lymphoid and non lymphoid organs, are professional antigen presenting cells (APC) which have the unique capacity to activate naive T cells. See, e.g., Banchereau and Steinman (1998) *Nature* 392:245–252; and Steinman (1991) *Annu. Rev. Immunol.* 9:271–296. DC, originated from bone-marrow, migrate as precursors through bloodstream to non lymphoid tissues where, at immature stage, DC such as the epidermal Langerhans cells capture antigens with high efficiency and become circulating veiled cells. These cells bearing antigens migrate from the peripheral non lymphoid tissues via lymphatics or bloodstream into lymphoid tissues where they localize in T cell-rich areas as mature interdigitating DC (IDC). See, e.g., Austyn (1996) *J. Exp. Med.* 183:1287–1292; Austyn, et al. (1988) *J. Exp. Med.* 167:646–651; Fossum (1988) *Scand. J. Immunol.* 27:97–105; Hoefsmit, et al. (1982) *Immumobiology.* 161:255–265; Kripke, et al. (1990) *J. Immunol.* 145:2833–2838; Larsen, et al. (1990) *J. Exp. Med.* 172:1483–1494; Macatonia, et al. (1987) *J. Exp. Med.* 166:1654–1667; Romani, et al. (1989) *J. Exp. Med.* 169:1169–1178. At this site, IDC efficiently present processed Ags to naive T cells and generate a specific immune response. See, e.g., Inaba, et al. (1983) *Proc. Natl. Acad. Sci. USA.* 80:6041–6045; and Inaba and Steinman (1985) *Science.* 229:475–479. Thus, migration constitutes an integral part of DC function.

The recruitment of DC into a site of tissue damage and the subsequent migration of DC into secondary lymphoid organs is dependent upon a dynamic and complex series of events, including activation by inflammatory stimuli. See, e.g., Butcher (1991) *Cell.* 67:1033–1036. This mechanism, implies transendothelial migration beyond the vascular compartment involving the expression of integrin molecules, the movement along leukocyte specific chemotactic gradients (Taub (1996) *Cytokine Growth Factor Rev.* 7:355–376) and possibly the secretion of matrix-degrading enzymes (Watanabe, et al. (1993) *J. Cell Sci.* 104:991–999). In addition, the trafficking of DC into tissues involves breaching the basement membrane (dermo-epidermic junction), which would necessitate the production of a matrix-degrading degrading enzyme.

Matrix metalloproteinases, or matrixins, represent a group of structurally related zinc-dependent endopeptidases that are involved in extracellular matrix and basement membrane degradation and cell-matrix interactions. See, e.g., Basbaum and Werb (1996) *Curr. Opin. Cell Biol.* 8:731–738; Birkedal-Hansen, et al. (1993) *Crit. Rev. Oral Biol. Med.* 4:197–250; Mignatti and Rifkin (1993) *Physiol. Rev.* 73:161–195; and Stetler-Stevenson, et al. (1993) *Annu. Rev. Cell Biol.* 9:541–573. They play crucial roles in tissue remodeling in normal and pathological processes, including development, repair, and cancer progression. All MMPs identified to date are synthesized as an inactive proenzyme form or zymogen, contain zinc-binding sites, and need proteqlytic activation to become functional proteases. According to their structural features and substrate specificity, four subclasses of MMPs have been established: collagenases have the unique capacity to degrade fibrillar collagens; gelatinases denature basement membranes and denatured collagens; stromelysins degrade many extracellular proteins, including proteoglycans, laminin, and fibronectin; and membrane-type MMPs are supposed to have proteolytic activity on other MMPs, required for their activation. See Matrisian (1992) *Bioessays.* 14:455–463; Stetler-Stevenson, et al. (1993) *Annu. Rev. Cell Biol.* 9:541–573; and Woessner (1991) *FASEB J.* 5:2145–2154. Among the 15 identified MMPs, four distinct members, presenting a transmembrane domain at the C terminus, have been described and are referred to as MT-MMP (Membrane-type matrix metalloproteinase). Sato, et al. (1994) *Nature* 370:61–65 first identified the MT1-MMP (MMP 14), responsible for the activation of progelatinase A (pro-MMP2) on the tumor cell surface that may trigger tissue invasion by tumor cells. Three additional members of this family, MT2-MMP (MMP 15), MT3-MMP (MMP 16) and MT4-MMP (MMP 17) have been isolated respectively from lung, placenta, and breast carcinoma cDNA libraries. See Puente, et al. (1996) *Cancer Res.* 56:944–949; Takino, et al. (1995) *J. Biol. Chem.* 270:23013–23020; and Will and Hinzmann (1995) *Eur. J. Biochem.* 231:602–608. All MT-MMPs, like the stromelysin-3 MMP (Basset, et al. (1990) *Nature* 348:699–704), contain a consensus insertion of about ten amino acids (RxK/RR) between the propeptide and the catalytic domain, corresponding to potential cleavage sites by enzymes called furin (Basbaum and Werb (1996) *Curr. Opin. Cell Biol.* 8:731–8; Sang and Douglas (1996) *J. Protein Chem.* 15:137–160). This cleavage is necessary to give rise to an activated form of MT-MMPs. The MT-MMPs are located in ternary complexes including a substrate, a tissue inhibitor of MMPs (TIMPs), and an activated MT-MMP, associated with the plasma membrane (Stetler-Stevenson, et al. (1993) *Annu. Rev. Cell Biol.* 9:541–573). As described for MT1-, MT2-, and MT3-MMPs, MT-MMPs may have a proteolytic activity on other MMPs like gelatinase A (pro-MMP2) and collagenase-3 (MMP 13) (see Butler, et al. (1997) *Eur. J. Biochem.* 244:653–657; Knauper, et al. (1996) *J. Biol. Chem.* 271:17124–17131; Kolkenbrock, et al. (1997) *Biol. Chem.* 378:71–76; Sato, et al. (1994) *Nature* 370:61–65; Strongin, et al. (1993) *J. Biol. Chem.* 268:14033–14039; and Takino, et al. (1995) *J. Biol. Chem.* 270:23013–23020).

The present invention provides DNA sequences encoding mammalian proteins which exhibit structural properties or motifs characteristic of a protease, more particularly a matrix metalloproteinase. The proteins described herein are designated F06B09. See Table 1.

Through an effort aiming at the identification of human dendritic cells (DC) specific genes, the cDNA coding for a fifth member of the human Membrane-type Matrix Metalloproteinases (MT-MMP) family has been cloned. The full-length 3691 bp cDNA which was mapped on chromosome 16p13.3, contains an open reading frame of some 1689 bp, encoding a 562 amino acid protein. The predicted protein was most homologous (48% amino acid homology) with the human matrix metalloproteinase MT4-MMP and has the typical features of member of the MMP family, including a prodomain with the activation locus, the zinc binding site, and the hemopexin domain.

The general roles of matrix metalloproteases are described above. The specific interaction of matrix metalloproteinases with other proteins, e.g., furin and progelatinase, are described in Basbaum and Werb (1996) *Current Opinion in Cell Biology* 8:731–738. Matrix metalloproteases are typically zinc endopeptidases that are required for the degradation of extracellular matrix components during normal embryo development, morphogenesis, and tissue remodeling. Their proteolytic activities are precisely regulated by endogenous tissue inhibitors of metalloproteases (TIMPS). Disruption of this balance results in diseases such as arthritis, atherosclerosis, and tumor growth and metastasis. Nagase (1996) in Hooper (ed.) *Zinc Metalloproteinases in Health and Disease* Taylor and Francis, London; Coussens and Werb (1996) *Chem. Biol.* 3:895–904. Therefore, F06B09 gene product could play a role in the migration of the dendritic cells (DC) or in the progression of the dendrites between the stromal cells. The way the MMPs act on the matrix is complex. The MMP is typically produced as an inactive proenzyme that needs to be processed by another protease, most probably furin, since F06B09 contains a site of cleavage for this convertase. This process probably occurs intracellularly (Basbaum and Werb (1996) *Current Opinion in Cell Biology* 8:731–738), and is likely followed by an interaction of F06B09 with other proteases like progelatinase.

A single 3.7 Kb mRNA transcript of this gene was found to be mainly expressed in CD34+-derived human DC and also weakly in in vitro generated granulocytes. No signal was detected in TF1, CHA, Jurkat, MRC5, or U937 cell lines, nor in freshly isolated monocytes, activated T and B cells, and activated peripheral blood lymphocytes (PBLs). Among normal adult human tissues, this mRNA was detected in spleen, lymph node, thymus, appendix, and bone marrow, but no expression was found in fetal tissues. RT-PCR distribution analysis showed a significant expression of the novel MT-MMP in activated DC and weakly in JY B cell line. Interestingly, it was found that the novel MT-MMP mRNA expression was down-regulated upon DC activation with CD40L. The expression pattern of this gene, which is predominantly expressed by DC, together with its putative membrane localization, suggest that it could be involved in the degradation of the extracellular matrix during DC migration.

The descriptions below are directed, for exemplary purposes, to primate embodiments, e.g., human, but are likewise applicable to related embodiments from other, e.g., natural, sources. Other ESTs have been identified from rodent cDNA libraries. These sources should, where appropriate, include various vertebrates, typically warm blooded animals, e.g., birds and mammals, particularly domestic animals, and primates. The sequences exhibit significant similarity to membrane-type matrix metalloproteases MT-MMP1 to 4. Table 2 shows an alignment of the family members.

TABLE 1

Human F06B09 nucleotide and predicted amino acid sequence.
SEQ ID NO: 1 and 2. Predicted signal sequence/cleavage is indicated.
Predicted extracellular domain about 1–527; transmembrane segment
about 528–543; cytoplasmic domain about 544–545.

```
CATGCAACAT AATCTTGCTC GATTCTAAAG TCAACGGATC CTGCAAAATT CGCGGCCGCG                    60

TCAACCCATT AGGTCTTGGC CTTGGAATAA AATTGCTTCT CGTCTGATTC CCGGGCCCAC                   120

CCGACCCAGC GGCGCAACCC TGGCCCTCCG GGACCCTCCG CTGACTCCAC CGCGCACTTC                   180

CCGGGACCCC CACACACATC CCAGCCCTCC GGCCGATCCC TCCCTACTCG GTGCCGGGTG                   240

CCCCCCTTTT TTTTCTAGGC CCGGATCTCC TCCCCCAGGT CCCCGGGGCG GCCCCAACCA                   300

GGCCCCCTTC AAACCCCGCC GGCGGCCCGG GCTGGGGCGC ACC ATG CGG CTG CGG                    355
                                             Met Arg Leu Arg
                                             -18          -15

CTC CGG CTT CTG GCG CTG CTG CTT CTG CAT GCT GGC ACC GCC CGC GCG                    403
Leu Arg Leu Leu Ala Leu Leu Leu Leu His Ala Gly Thr Ala Arg Ala
              -10                  -5                    1

CGC CCC GAA GCC CTC GGC GCA GGA CTT AGC CTG GGC TGT GAG AAC TGG                    451
Arg Pro Glu Ala Leu Gly Ala Gly Leu Ser Leu Gly Cys Glu Asn Trp
            5                  10                  15

CTG ACT CGC TAT GGT TAC CTA CCG CCA CCC GAC CCT GCC CAG GCC CAG                    499
Leu Thr Arg Tyr Gly Tyr Leu Pro Pro Pro Asp Pro Ala Gln Ala Gln
         20                  25                  30

CTG CAG AGC CCT GAA AAT TTG CGC GAT GCC ATC AAA GTC ATG CAA AGG                    547
Leu Gln Ser Pro Glu Asn Leu Arg Asp Ala Ile Lys Val Met Gln Arg
 35                  40                  45                  50

TTC GCG GGG CTG CCG GAG ACC GGC CGC ATG GAC CCA GGG ACA GTG GCC                    595
Phe Ala Gly Leu Pro Glu Thr Gly Arg Met Asp Pro Gly Thr Val Ala
                 55                  60                  65

ACC ATG CGT AAG CCC CGC TGC TCC CTG CCT GAC GTG CTG GGG GTG GCG                    643
Thr Met Arg Lys Pro Arg Cys Ser Leu Pro Asp Val Leu Gly Val Ala
                 70                  75                  80

GGG CTG GTC AGG CGG CGT CGC CGG TAC GGT CTG AGC GGC AGC GTG TGG                    691
Gly Leu Val Arg Arg Arg Arg Tyr Gly Leu Ser Gly Ser Val Trp
                 85                  90                  95

GAG AAG CGA ACC GTG ACA TGG AGG GTA CGT TCC TTC CCC CAG AGC TCC                    739
Glu Lys Arg Thr Val Thr Trp Arg Val Arg Ser Phe Pro Gln Ser Ser
        100                 105                 110

CAG GTG AGC CAG GAG ACC GTG CGG GTC CTC GTG AGC TAT GCC CTG ATG                    787
Gln Val Ser Gln Glu Thr Val Arg Val Leu Val Ser Tyr Ala Leu Met
115                 120                 125                 130

GCG TGG GGC ATG GAG TCA GGC CTC ACA TTT CAT GAG GTG GAT TCC CCC                    835
Ala Trp Gly Met Glu Ser Gly Leu Thr Phe His Glu Val Asp Ser Pro
                135                 140                 145
```

TABLE 1-continued

| | |
|---|---|
| CAG GGC CAG GAG CCC GAC ATC CTC ATA GAC TTT GCC CGC GCC TTC CAA<br>Gln Gly Gln Glu Pro Asp Ile Leu Ile Asp Phe Ala Arg Ala Phe Gln<br>          150                    155                   160 | 883 |
| CAG GAC AGC TAC CCC TTC GAC GGG TTG GGG GGC ACC CTA GCC CAT GCC<br>Gln Asp Ser Tyr Pro Phe Asp Gly Leu Gly Gly Thr Leu Ala His Ala<br>          165                    170                   175 | 931 |
| TTC TTC CCT GGG GAG CAC CCC ATC TCC GGG GAC ACT CAC TTT GAC GAT<br>Phe Phe Pro Gly Glu His Pro Ile Ser Gly Asp Thr His Phe Asp Asp<br>180                      185                   190 | 979 |
| GAG GAG ACC TGG ACT TTT GGG TCA AAA GAC GGC GAG GGG ACC GAC CTG<br>Glu Glu Thr Trp Thr Phe Gly Ser Lys Asp Gly Glu Gly Thr Asp Leu<br>195                      200                   205                   210 | 1027 |
| TTT GCC GTG GCT GTC CAT GAG TTT GGC CAC GCC CTG GGC ATG GGC CAC<br>Phe Ala Val Ala Val His Glu Phe Gly His Ala Leu Gly Met Gly His<br>                  215                    220                   225 | 1075 |
| TCC TCA GCC CCC GAC TCC ATT ATG AGG CCC TTC TAC CAG GGT CCG GTG<br>Ser Ser Ala Pro Asp Ser Ile Met Arg Pro Phe Tyr Gln Gly Pro Val<br>                  230                    235                   240 | 1123 |
| GGC GAC CCT GAC AAG TAC CGC CTG TCT CTG GAT GAC CGC GAT GGC CTG<br>Gly Asp Pro Asp Lys Tyr Arg Leu Ser Leu Asp Asp Arg Asp Gly Leu<br>          245                    250                    255 | 1171 |
| CAG CAA CTC TAT GGG AAG GCG CCC CAA ACC CCA TAT GAC AAG CCC ACA<br>Gln Gln Leu Tyr Gly Lys Ala Pro Gln Thr Pro Tyr Asp Lys Pro Thr<br>          260                    265                   270 | 1219 |
| AGG AAA CCC CTG GCT CCT CCG CCC CAG CCC CCG GCC TCG CCC ACA CAC<br>Arg Lys Pro Leu Ala Pro Pro Pro Gln Pro Pro Ala Ser Pro Thr His<br>275                      280                   285                   290 | 1267 |
| AGC CCA TCC TTC CCC ATC CCT GAT CGA TGT GAG GGC AAT TTT GAC GCC<br>Ser Pro Ser Phe Pro Ile Pro Asp Arg Cys Glu Gly Asn Phe Asp Ala<br>                  295                    300                   305 | 1315 |
| ATC GCC AAC ATC CGA GGG GAA ACT TTC TTC TTC AAA GGC CCC TGG TTC<br>Ile Ala Asn Ile Arg Gly Glu Thr Phe Phe Phe Lys Gly Pro Trp Phe<br>                  310                    315                   320 | 1363 |
| TGG CGC CTC CAG CCC TCC GGA CAG CTG GTG TCC CCG CGA CCC GCA CGG<br>Trp Arg Leu Gln Pro Ser Gly Gln Leu Val Ser Pro Arg Pro Ala Arg<br>          325                    330                   335 | 1411 |
| CTG CAC CGC TTC TGG GAG GGG CTG CCC GCC CAG GTG AGG GTG GTG CAG<br>Leu His Arg Phe Trp Glu Gly Leu Pro Ala Gln Val Arg Val Val Gln<br>          340                    345                   350 | 1459 |
| GCC GCC TAT GCT CGG CAC CGA GAC GGC CGA ATC CTC CTC TTT AGC GGG<br>Ala Ala Tyr Ala Arg His Arg Asp Gly Arg Ile Leu Leu Phe Ser Gly<br>355                      360                   365                   370 | 1507 |
| CCC CAG TTC TGG GTG TTC CAG GAC CGG CAG CTG GAG GGC GGG GCG CGG<br>Pro Gln Phe Trp Val Phe Gln Asp Arg Gln Leu Glu Gly Gly Ala Arg<br>                  375                    380                   385 | 1555 |
| CCG CTC ACG GAG CTG GGG CTG CCC CCG GGA GAG GAG GTG GAC GCC GTG<br>Pro Leu Thr Glu Leu Gly Leu Pro Pro Gly Glu Glu Val Asp Ala Val<br>                  390                    395                   400 | 1603 |
| TTC TCG TGG CCA CAG AAC GGG AAG ACC TAC CTG GTC CGC GGC CGG CAG<br>Phe Ser Trp Pro Gln Asn Gly Lys Thr Tyr Leu Val Arg Gly Arg Gln<br>          405                    410                   415 | 1651 |
| TAC TGG CGC TAC GAC GAG GCG GCG GCG CGC CCG GAC CCC GGC TAC CTT<br>Tyr Trp Arg Tyr Asp Glu Ala Ala Ala Arg Pro Asp Pro Gly Tyr Leu<br>          420                    425                   430 | 1699 |
| CGC GAC CTG AGC CTC TGG GAA GGC GCG CCC CCC TCC CCT GAC GAT GTC<br>Arg Asp Leu Ser Leu Trp Glu Gly Ala Pro Pro Ser Pro Asp Asp Val<br>435                      440                   445                   450 | 1747 |
| ACC GTC AGC AAC GCA GGT GAC ACC TAC TTC TTC AAG GGC GCC CAC TAC<br>Thr Val Ser Asn Ala Gly Asp Thr Tyr Phe Phe Lys Gly Ala His Tyr<br>                  455                    460                   465 | 1795 |

TABLE 1-continued

```
TGG CGC TTC CCC AAG AAC AGC ATC AAG ACC GAG CCG GAC GCC CCC CAG      1843
Trp Arg Phe Pro Lys Asn Ser Ile Lys Thr Glu Pro Asp Ala Pro Gln
            470                 475                 480

CCC ATG GGG CCC AAC TGG CTG GAC TGC CCC GCC CCG AGC TCT GGT CCC      1891
Pro Met Gly Pro Asn Trp Leu Asp Cys Pro Ala Pro Ser Ser Gly Pro
        485                 490                 495

CGC GCC CCC AGG CCC CCC AAA GGG ACC CCC GTG TCC GAA ACC TGC GAT      1939
Arg Ala Pro Arg Pro Pro Lys Gly Thr Pro Val Ser Glu Thr Cys Asp
    500                 505                 510

TGT CAG TGC GAG CTC AAC CAG GCC GCA GGA CGT TGG CCT GCT CCC ATC      1987
Cys Gln Cys Glu Leu Asn Gln Ala Ala Gly Arg Trp Pro Ala Pro Ile
515                 520                 525                 530

CCG CTG CTC CTC TTG CCC CTG CTG GTG GGG GGT GTA GCC TCC CGC          2032
Pro Leu Leu Leu Leu Pro Leu Leu Val Gly Gly Val Ala Ser Arg
                535                 540                 545

TGATGGGGGG AGCCATCCAG ACCGAACAGC GCCCTCCACG GCCGAGTCCC CCGCCGCTGG    2092

ACCTGGTCGG GGGTTGTGAG GCGCTGCGGA GGCCCCTTGT CTGTTCCCAC GGACGGGGGC    2152

TCGGCGCGCG ACTAAGCAGG GGGGATCTCC CGCGCAGGGG CGGCGGCGGC GGGGACCGGT    2212

CGCCTGGCGC TGGGCTCAGT CTCCTCAGGG TCTGAGACCC CGGCGCTGCC ACCGGAACCC    2272

GCCTTCAGGG GCGCACGCGC GCTGGGACCA TGCGTCGGTC GTCGCCCCCG TCGTTCCCTC    2332

CCGGCTGCCG CCAGGGGGCG GTCGGACCCC GCCTCCCGAG CCCGGGGAGG GGCGGGGAGG    2392

ACAAGGGGCG GGCCCGCGGC CTCACCCGGA GGGACGGCAG CCCCGGTCGC GCGCTGGCCC    2452

CGCAGGACCT TCCTTTTCCA GGAAGAGCCA GCTTTTCTCG GAGCGCAGTC CTGGGACTCT    2512

CCGCAGCCCC GCCCCGCCTG GCCACTGCGT CTGGCATTCC TGGGTCGTTA GAGGACAGGC    2572

CTGACTGCGA AGCTGTGCCT TGCCCCTCTC CCACCCGCAG TTTCTCACCC CGTTCTGCTC    2632

CCACAAGGCC CCCCTACAGT CACTGCCACA CTGGTGGGGA CCTGGGACCC AGACCCGGAA    2692

CCAGCCCAGA TATCACCCCT GAGGACCCAT GCGCCACGTC CTGGGTGGTG GAATCAGTGG    2752

GTGGAGGGAC GACCCTTGCT CTCCAGGCTG TTAACCTTTT CCGTTGCTCC CCCGCCACCC    2812

ACCTCCTCCT CCCCAGGCCA CCCAACTTGG GCACCTCCCT GGGCCCAGAA CTGCCTTCCA    2872

TTCAATGGGG AACCCTTCTA TCCCCAAGAA CCCCTTCCCT GCTTGCACCC TGGAGAGAAC    2932

AGCTTGACTC CCATCAACTC AACGCTGGTG GAAAGACAGG GACCGAACCC TGGCTCAGGC    2992

CTGGTCATTG CCTCCTCAGC ACTCCCTCCT GGGAGGCCTT AGCTCTAGAG TGAGGGGTGG    3052

GTGGAACCTG GGGGCACCTC GTTCACCCTG TCCCCACTCC CCACAGTTTT AGGATCTAAA    3112

TGATTGCCTC TGGAACTATT CTTCTAGACT ATCCCACATC AGAATCACTG GGAAATTTAA    3172

GTTTGCAGAT CCCACACTCA CCCTGAATCC TCACTCAGGG TGGGGTCAGG AATCTGCATT    3232

TTAACTAGTC GCGGGGATTG TGGGGGGCAG TAGCTGGCTG TTTCGTGGCA TTTCTGTGGC    3292

TCTGCAGTGT TCCTCCACCC CAGGACCAAT ATGTTCAGGC CACACCGATG GCCTGAACCC    3352

CATGGGTAGA GTCACTTAGG GGCCACTTCC TAAGTTGCTG TCCAGCCTCA GTGACCCCCT    3412

AGTGCTTCCT GGAGCTGAGG CTGTGGGCGG CTGTCCCAGC AACCAAGCGA GGGGTTGCCC    3472

CAGTTGCTCA TACAAACAGA TCAGCATGAG GACAGAAGGC AGGAGACTTT GGTCAGTTAC    3532

CTGGGAATTC TGGGCTGCCA GGAAACGATT TGGGCCTCTG TCAGTTTCTT TTCCATGTAT    3592

GAGGAGGGGG AAATTTGTAT ATTAGATACT TATTCATCCC ACTCTGGACA ATAAAAACGA    3652

ATGTACAAAA AAAACATAAA AAAAAAAAAT AAAGAAAATC AAA                      3695
```

Alternative sequence of F06B09 provides (SEQ ID NO: 3 and 4).
Notable motifs include: predicted signal sequence, as shown;

TABLE 1-continued propeptide domain from about 1–66; C switch motif from about 67–73; furin site from about 82–86; catalytic site from about 87–211; zinc binding site from about 212–222, with notable His at 212, 216, and 222; hinge region from about 260–290; hemopexin-like domain from about 291–525; transmembrane segment from about 526–538; and cytoplasmic tail from about 539–542.

| | | |
|---|---|---:|
| CATGCAACAT AATCTTGCTC GATTCTAAAG TCAACGGATC CTGCAAAATT CGCGGCCGCG | | 60 |
| TCAACCCATT AGGTCTTGGC CTTGGAATAA AATTGCTTCT CGTCTGATTC CCGGGCCCAC | | 120 |
| CCGACCCAGC GGCGCAACCC TGGCCCTCCG GGACCCTCCG CTGACTCCAC CGCGCACTTC | | 180 |
| CCGGGACCCC CACACACATC CCAGCCCTCC GGCCGATCCC TCCCTACTCG GTGCCGGGTG | | 240 |
| CCCCCCGCCC TCTCCAGGCC CGGATCTCCT CCCCCAGGTC CCCGGGGCGG CCCCAGCCAG | | 300 |
| GCCCCCTTCG AACCCCGCCG GCGGCCCGGG CTGGGGCGCA CC ATG CGG CTG CGG | | 355 |
| | Met Arg Leu Arg | |
| | -18        -15 | |
| CTC CGG CTT CTG GCG CTG CTG CTT CTG CTG GCA CCG CCC GCG CGC | | 402 |
| Leu Arg Leu Leu Ala Leu Leu Leu Leu Leu Ala Pro Pro Ala Arg | | |
|     -15             -10              -5                    | | |
| GCC CCG AAG CCC TCG GCG CAG GAC GTG AGC CTG GGC GTG GAC TGG CTG | | 450 |
| Ala Pro Lys Pro Ser Ala Gln Asp Val Ser Leu Gly Val Asp Trp Leu | | |
|  1               5                  10                  15 | | |
| ACT CGC TAT GGT TAC CTG CCG CCA CCC CAC CCT GCC CAG GCC CAG CTG | | 498 |
| Thr Arg Tyr Gly Tyr Leu Pro Pro Pro His Pro Ala Gln Ala Gln Leu | | |
|              20                  25                  30     | | |
| CAG AGC CCT GAG AAG TTG CGC GAT GCC ATC AAA GTC ATG CAG AGG TTC | | 546 |
| Gln Ser Pro Glu Lys Leu Arg Asp Ala Ile Lys Val Met Gln Arg Phe | | |
|          35                  40                  45         | | |
| GCG GGG CTG CCG GAG ACC GGC CGC ATG GAC CCA GGG ACA GTG GCC ACC | | 594 |
| Ala Gly Leu Pro Glu Thr Gly Arg Met Asp Pro Gly Thr Val Ala Thr | | |
|      50                  55                  60             | | |
| ATG CGT AAG CCC CGC TGC TCC CTG CCT GAC GTG CTG GGG GTG GCG GGG | | 642 |
| Met Arg Lys Pro Arg Cys Ser Leu Pro Asp Val Leu Gly Val Ala Gly | | |
|  65                  70                  75                 | | |
| CTG GTC AGG CGG CGT CGC CGG TAC GCT CTG AGC GGC AGC GTG TGG AAG | | 690 |
| Leu Val Arg Arg Arg Arg Tyr Ala Leu Ser Gly Ser Val Trp Lys | | |
| 80                  85                  90                  95 | | |
| AAG CGA ACC CTG ACA TGG AGG GTA CGT TCC TTC CCC CAG AGC TCC CAG | | 738 |
| Lys Arg Thr Leu Thr Trp Arg Val Arg Ser Phe Pro Gln Ser Ser Gln | | |
|              100                 105                 110    | | |
| CTG AGC CAG GAG ACC GTG CGG GTC CTC ATG AGC TAT GCC CTG ATG GCC | | 786 |
| Leu Ser Gln Glu Thr Val Arg Val Leu Met Ser Tyr Ala Leu Met Ala | | |
|          115                 120                 125        | | |
| TGG GGC ATG GAG TCA GGC CTC ACA TTT CAT GAG GTG GAT TCC CCC CAG | | 834 |
| Trp Gly Met Glu Ser Gly Leu Thr Phe His Glu Val Asp Ser Pro Gln | | |
|      130                 135                 140            | | |
| GGC CAG GAG CCC GAC ATC CTC ATC GAC TTT GCC CGC GCC TTC CAC CAG | | 882 |
| Gly Gln Glu Pro Asp Ile Leu Ile Asp Phe Ala Arg Ala Phe His Gln | | |
|  145                 150                 155               | | |
| GAC AGC TAC CCC TTC GAC GGG TTG GGG GGC ACC CTA GCC CAT GCC TTC | | 930 |
| Asp Ser Tyr Pro Phe Asp Gly Leu Gly Gly Thr Leu Ala His Ala Phe | | |
| 160                 165                 170                 175 | | |
| TTC CCT GGG GAG CAC CCC ATC TCC GGG GAC ACT CAC TTT GAC GAT GAG | | 978 |
| Phe Pro Gly Glu His Pro Ile Ser Gly Asp Thr His Phe Asp Asp Glu | | |
|              180                 185                 190    | | |
| GAG ACC TGG ACT TTT GGG TCA AAA GAC GGC GAG GGG ACC GAC CTG TTT | | 1026 |
| Glu Thr Trp Thr Phe Gly Ser Lys Asp Gly Glu Gly Thr Asp Leu Phe | | |
|          195                 200                 205        | | |
| GCC GTG GCT GTC CAT GAG TTT GGC CAC GCC CTG GGC CTG GGC CAC TCC | | 1074 |
| Ala Val Ala Val His Glu Phe Gly His Ala Leu Gly Leu Gly His Ser | | |

TABLE 1-continued

|  | 210 |  |  |  | 215 |  |  |  | 220 |  |  |  |  |
|---|---|---|---|---|---|---|---|---|---|---|---|---|---|
| TCA | GCC | CCC | AAC | TCC | ATT | ATG | AGG | CCC | TTC | TAC | CAG | GGT | CCG GTG GGC | 1122 |
| Ser | Ala | Pro | Asn | Ser | Ile | Met | Arg | Pro | Phe | Tyr | Gln | Gly | Pro Val Gly |  |
|  | 225 |  |  |  | 230 |  |  |  | 235 |  |  |  |  |

```
TCA GCC CCC AAC TCC ATT ATG AGG CCC TTC TAC CAG GGT CCG GTG GGC    1122
Ser Ala Pro Asn Ser Ile Met Arg Pro Phe Tyr Gln Gly Pro Val Gly
    225             230             235

GAC CCT GAC AAG TAC CGC CTG TCT CAG GAT GAC CGC GAT GGC CTG CAG    1170
Asp Pro Asp Lys Tyr Arg Leu Ser Gln Asp Asp Arg Asp Gly Leu Gln
240             245             250             255

CAA CTC TAT GGG AAG GCG CCC CAA ACC CCA TAT GAC AAG CCC ACA AGG    1218
Gln Leu Tyr Gly Lys Ala Pro Gln Thr Pro Tyr Asp Lys Pro Thr Arg
                260             265             270

AAA CCC CTG GCT CCT CCG CCC CAG CCC CCG GCC TCG CCC ACA CAC AGC    1266
Lys Pro Leu Ala Pro Pro Pro Gln Pro Pro Ala Ser Pro Thr His Ser
            275             280             285

CCA TCC TTC CCC ATC CCT GAT CGA TGT GAG GGC AAT TTT GAC GCC ATC    1314
Pro Ser Phe Pro Ile Pro Asp Arg Cys Glu Gly Asn Phe Asp Ala Ile
        290             295             300

GCC AAC ATC CGA GGG GAA ACT TTC TTC TTC AAA GGC CCC TGG TTC TGG    1362
Ala Asn Ile Arg Gly Glu Thr Phe Phe Phe Lys Gly Pro Trp Phe Trp
    305             310             315

CGC CTC CAG CCC TCC GGA CAG CTG GTG TCC CCG CGA CCC GCA CGG CTG    1410
Arg Leu Gln Pro Ser Gly Gln Leu Val Ser Pro Arg Pro Ala Arg Leu
320             325             330             335

CAC CGC TTC TGG GAG GGG CTG CCC GCC CAG GTG AGG GTG GTG CAG GCC    1458
His Arg Phe Trp Glu Gly Leu Pro Ala Gln Val Arg Val Val Gln Ala
                340             345             350

GCC TAT GCT CGG CAC CGA GAC GGC CGA ATC CTC CTC TTT AGC GGG CCC    1506
Ala Tyr Ala Arg His Arg Asp Gly Arg Ile Leu Leu Phe Ser Gly Pro
            355             360             365

CAG TTC TGG GTG TTC CAG GAC CGG CAG CTG GAG GGC GGG GCG CGG CCG    1554
Gln Phe Trp Val Phe Gln Asp Arg Gln Leu Glu Gly Gly Ala Arg Pro
        370             375             380

CTC ACG GAG CTG GGG CTG CCC CCG GGA GAG GAG GTG GAC GCC GTG TTC    1602
Leu Thr Glu Leu Gly Leu Pro Pro Gly Glu Glu Val Asp Ala Val Phe
    385             390             395

TCG TGG CCA CAG AAC GGG AAG ACC TAC CTG GTC CGC GGC CGG CAG TAC    1650
Ser Trp Pro Gln Asn Gly Lys Thr Tyr Leu Val Arg Gly Arg Gln Tyr
400             405             410             415

TGG CGC TAC GAC GAG GCG GCG GCG CGC CCG GAC CCC GGC TAC CCT CGC    1698
Trp Arg Tyr Asp Glu Ala Ala Ala Arg Pro Asp Pro Gly Tyr Pro Arg
                420             425             430

GAC CTG AGC CTC TGG GAA GGC GCG CCC CCC TCC CCT GAC GAT GTC ACC    1746
Asp Leu Ser Leu Trp Glu Gly Ala Pro Pro Ser Pro Asp Asp Val Thr
            435             440             445

GTC AGC AAC GCA GGT GAC ACC TAC TTC TTC AAG GGC GCC CAC TAC TGG    1794
Val Ser Asn Ala Gly Asp Thr Tyr Phe Phe Lys Gly Ala His Tyr Trp
        450             455             460

CGC TTC CCC AAG AAC AGC ATC AAG ACC GAG CCG GAC GCC CCC CAG CCC    1842
Arg Phe Pro Lys Asn Ser Ile Lys Thr Glu Pro Asp Ala Pro Gln Pro
    465             470             475

ATG GGG CCC AAC TGG CTG GAC TGC CCC GCC CCG AGC TCT GGT CCC CGC    1890
Met Gly Pro Asn Trp Leu Asp Cys Pro Ala Pro Ser Ser Gly Pro Arg
480             485             490             495

GCC CCC AGG CCC CCC AAA GCG ACC CCC GTG TCC GAA ACC TGC GAT TGT    1938
Ala Pro Arg Pro Pro Lys Ala Thr Pro Val Ser Glu Thr Cys Asp Cys
                500             505             510

CAG TGC GAG CTC AAC CAG GCC GCA GGA CGT TGG CCT GCT CCC ATC CCG    1986
Gln Cys Glu Leu Asn Gln Ala Ala Gly Arg Trp Pro Ala Pro Ile Pro
            515             520             525

CTG CTC CTC TTG CCC CTG CTG GTG GGG GGT GTA GCC TCC CGC             2028
```

TABLE 1-continued

```
Leu Leu Leu Leu Pro Leu Leu Val Gly Gly Val Ala Ser Arg
        530             535                 540
TGATGGGGGG AGCCATCCAG ACCGAACAGC GCCCTCCACG GCCGAGTCCC CCGCCGCTGG      2088
ACCTGGTCGG GGGTTGTGAG GCGCTGCGGA GGCCCCTTGT CTGTTCCCAC GGACGGGGGC      2148
TCGGGCGCGG ACTAAGCAGG GGGGATCTCC CGCGCAGGGG CGGCGGCGGC GGGGACCGGT      2208
CGCCTGGCGC TGGGCTCAGT CTCCTCAGGG TCTGAGACCC CGGCGCTGCC ACCGGAACCC      2268
GCCTTCAGGG GCGCACGCGC GCTGGGACCA TGCGTCGGTC GTCGCCCCCG TCGTTCCCTC      2328
CCGGCTGCCG CCAGGGGGCG GTCGGACCCC GCCTCCCGAG CCCGGGGAGG GGCGGGGAGG      2388
ACAAGGGGCG GGCCCGCGGC CTCACCCGGA GGGACGGCAG CCCCGGTCGC GCGCTGGCCC      2448
CGCAGGACCT TCCTTTTCCA GGAAGAGCCA GCTTTTCTCG GAGCGCAGTC CTGGGACTCT      2508
CCGCAGCCCC GCCCCGCCTG GCCACTGCGT CTGGCATTCC TGGGTCGTTA GAGGACAGGC      2568
CTGACTGCGA AGCTGTGCCT TGCCCCTCTC CCACCCGCAG TTTCTCACCC CGTTCTGCTC      2628
CCACAAGGCC CCCCTACAGT CACTGCCACA CTGGTGGGGA CCTGGGACCC AGACCCGGAA      2688
CCAGCCCAGA TATCACCCCT GAGGACCCAT GCGCCACGTC CTGGGTGGTG GAATCAGTGG      2748
CTGGAGGGAC GACCCTTGCT CTCCAGGCTG TTAACCTTTT CCGTTGCTCC CCCGqCACCC      2808
ACCTCCTCCT CCCCAGGCCA CCCAACTTGG GCACCTCCCT GGGCCCAGAA CTGCCTTCCA      2868
TTCAATGGGG AACCCTTCTA TCCCCAAGAA CCCCTTCCCT GCTTGCACCC TGGAGAGAAC      2928
AGCTTGACTC CCATCAACTC AACGCTGGTG GAAAGACAGG GACCGAACCC TGGCTCAGGC      2988
CTGGTCATTG CCTCCTCAGC ACTCCCTCCT GGGAGGCCTT AGCTCTAGAG TGAGGGGTGG      3048
GTGGAACCTG GGGGCACCTC GTTCACCCTG TCCCCACTCC CCACAGTTTT AGGATCTAAA      3108
TGATTGCCTC TGGAACTATT CTTCTAGACT ATCCCACATC AGAATCACTG GGAAATTTAA      3168
GTTTGCAGAT CCCACACTCA CCCTGAATCC TCACTCAGGG TGGGGTCAGG AATCTGCATT      3228
TTAACTAGTC GCGGGGATTG TGGGGGGCAG TAGCTGGCTG TTTCGTGGCA TTTCTGTGGC      3288
TCTGCAGTGT TCCTCCACCC CAGGACCAAT ATGTTCAGGC CACACCGATG GCCTGAACCC      3348
CATGGGTAGA GTCACTTAGG GGCCACTTCC TAAGTTGCTG TCCAGCCTCA GTGACCCCCT      3408
AGTGCTTCCT GGAGCTGAGG CTGTGGGCGG CTGTCCCAGC AACCACGCGA GGGGTTGCCC      3468
CAGTTGCTCA TACAAACAGA TCAGCATGAG GACAGAAGGC AGGAGACTTT GGTCAGTTAC      3528
CTGGGAATTC TGGGCTGCCA GGAAACGATT TGGGCCTCTG TCAGTTTCTT TTCCATGTAT      3588
GAGGAGGGGG AAATTTGTAT ATTAGATACT TATTCATCCC ACTCTGGACA ATAAAAACGA      3648
ATGTACAAAA AAAACATAAA AAAAAAAAAT AAAGAAAATC AAA                       3691
MRLRLRLLAL LLLLLAPPAR APKPSAQDVS LGVDWLTRYG YLPPPHPAQA
QLQSPEKLRD AIKVMQRFAG LPETGRMDPG TVATMRKPRC SLPDVLGVAG
LVRRRRRYAL SGSVWKKRTL TWRVRSFPQS SQLSQETVRV LMSYALMAWG
MESGLTFHEV DSPQGQEPDI LIDFARAFHQ DSYPFDGLGG TLAHAFFPGE
HPISGDTHFD DEETWTFGSK DGEGTDLFAV AVHEFGHALG LGHSSAPNSI
MRPFYQGPVG DPDKYRLSQD DRDGLQQLYG KAPQTPYDKP TRKPLAPPPQ
PPASPTHSPS FPIPDRCEGN FDAIANIRGE TFFFKGPWFW RLQPSGQLVS
PRPARLHRFW EGLPAQVRVV QAAYARHRDG RILLFSGPQF WVFQDRQLEG
GARPLTELGL PPGEEVDAVF SWPQNGKTYL VRGRQYWRYD EAAARPDPGY
PRDLSLWEGA PPSPDDVTVS NAGDTYFFKG AHYWRFPKNS IKTEPDAPQP
```

TABLE 1-continued

```
MGPNWLDCPA PSSGPRAPRP PKATPVSETC DCQCELNQAA GRWPAPIPLL

LLPLLVGGVA SR
```

TABLE 2

Comparison of various MMPs with F06B09. MT4-MMP (SEQ ID NO: 7) is from Genbank 3466295 (EMBL X89576); MT2-MMP (SEQ ID NO: 8) Z48482): MT1-MMP (SEQ ID NO: 9) is from Genbank 804994 (EMBL X83535; see also Genbank 1495995 (EMBL X90925) and 793763 (DDBJ D26512); and MT3-MMP (SEQ ID NO: 10) is from Genbank 2424979 (DDBJ D85511).

```
MT4-MMP    1                                                                        0

F06B09     1              MRLRLRLLALLLLLLAPPARAPKPSAQDVSLGVDWLTRY   39

MT2-MMP    1                                                                        0

MT1-MMP    1              MSPAPRPSRCLLLPLLTLGTALASLGSAQSSSFSPEAWLQQY 42

MT3-MMP    1 MILLTFSTGRRLDFVHHSGVFFLQTLLWILCATVCGTEQYFNVEVWLQKY 50

MT4-MMP    1                           MQQFGGLEATGILDEATLALMKTPR   25

F06B09    40 GYLPPPHPAQAQLQSPEKLRDAIKVMQRFAGLPETGRMDPGTVATMRKPR   89

MT2-MMP    1                                                MKRPR    5

MT1-MMP   43 GYLPPGDLRTHTQRSPQSLSAAIAAMQKFYGLQVTGKADADTMKAMRRPR   92

MT3-MMP   51 GYLPPTDPRMSVLRSAETMQSALAAMQQFYGINMTGKVDRNTIDWMKKPR  100
                                                          *. **

MT4-MMP   26 CSLPDLP-VLTQARRR--RQ--APAPTKWNKRNLSWRVRTFPRDSPLGHD   70

F06B09    90 CSLPDVL-GVAGLVRR--RRRYALSGSVKKKRTLTWRVRSFPQSSQLSQE  136

MT2-MMP    6 CGVPDQFGVRVKANLRRRRKRYALTGRKWNNHHLTFSIQNYT--EKLGWY   53

MT1-MMP   93 CGVPDKFGAEIKANVR--RKRYAIQGLKWQHNEITFCIQNYT--PKVGEY  138

MT3-MMP  101 CGVPDQTRGSSKFHIR--RKRYALTGQKWQHKHITYSIKNVT--PKVGDP  146
                * .**        *  *. *    *    .. ..     .

MT4-MMP   71 TVRALMYYALKVWSDIAPLNFHEVA---GS-----TADIQIDFSKADHND  112

F06B09   137 TVRVLMSYALMAWGMESGLTFHEVDSPQGQ-----EPDILIDFARAFHQD  181

MT2-MMP   54 HSMEAVRRAFRVWEQATPLVFQEVPYEDIRLRRQKEADIMVLFASGFHGD  103

MT1-MMP  139 ATYEAIRKAFRVWESATPLRFREVPYAYIREGHEKQADIMIFFAEGFHGD  188

MT3-MMP  147 ETRKAIRRAFDVWQNVTPLTFEEVPYSELENGK-RDVDITIIFASGFHGD  195
                 . *   *   . * * **        ** . *.   * *

MT4-MMP  113 GYPFDGPGGTVAHAFFPGHHHTAGDTHFDDDEAWTFRSSDAHGMDLFAVA  162

F06B09   182 SYPFDGLGGTLAHAFFPGEHPISGDTHFDDEETWTFGSKDGEGTDLFAVA  231

MT2-MMP  104 SSPFDGTGGFLAHAYFPGPG-LGGDTHFDADEPWTFSSTDLHGNNLFLVA  152

MT1-MMP  189 STPFDGEGGFLAHAYFPGPN-IGGDTHFDSAEPWTVRNEDLNGNDIFLVA  237

MT3-MMP  196 SSPFDGEGGFLAHAYFPGPG-IGGDTHFDSDEPWTLGNPNHDGNDLFLVA  244
              **** ** .***.***      ******  * **      *  .* **

MT4-MMP  163 VHEFGHAIGLSHVAAAHSIMRPYYQGPVGDPLRYGLPYEDKVRVWQLYGV  212

F06B09   232 VHEFGHALGLGHSSAPNSIMRPFYQGPVGDPDKYRLSQDDRDGLQQLYG-  280

MT2-MMP  153 VHELGHALGLEHSSNPNAIMAPFYQWKDVDN--FKLPEDDLRGIQQLYGT  200
```

TABLE 2-continued

Comparison of various MMPs with F06B09. MT4-MMP (SEQ ID NO: 7) is from Genbank 3466295 (EMBL X89576); MT2-MMP (SEQ ID NO: 8) Z48482): MT1-MMP (SEQ ID NO: 9) is from Genbank 804994 (EMBL X83535; see also Genbank 1495995 (EMBL X90925) and 793763 (DDBJ D26512); and MT3-MMP (SEQ ID NO: 10) is from Genbank 2424979 (DDBJ D85511).

```
MT1-MMP  238 VHELGHALGLEHSSDPSAIMAPFYQWMDTEN--FVLPDDDRRGIQQLYGG 285

MT3-MMP  245 VHELGHALGLEHSNDPTAIMAPFYQYMETDN--FKLPNDDLQGIQKIYGP 292
             *** ***.** *     .** *.**       . . * .*    . ...**

MT4-MMP  213 RESVSPTAQ--PEEPPLLP----------EP------------PDNRSSA 238

F06P09   281 KAPQTPYDK--PTRKPLAP----------PPQ----------PPASPTH 307

MT2-MMP  201 PDGQPQPTQPLPTVTPRRPG-----RPDHRPPRPPQPPPPGGKPERPPKP 245

MT1-MMP  286 ESG-------FPTKMPPQP------RTTSRP----------SVPDKPKNP 312

MT3-MMP  293 PDKIPPPTRPLPTVPPHRSIPPADPRKNDRP----------KPPRPPTG 331
                      *   *              *               *

MT4-MMP  239 PPR----------KDVPHRCSTHFDAVAQIRGEAFFFKGKYFWRLTRDRH 278

F06B09   308 SPS----------FPIPDRCEGNFDAIANIRGETFFFKGPWFWRLQPSGQ 347

MT2-MMP  246 GPPVQPRATERPDQYGPNICDGDFDTVAMLRGEMFVFKGRWFWRVRHNR- 294

MT1-MMP  313 -------------TYGPNICDGNFDTVAMLRGEMFVFKERWFWRVRNNQ- 348

MT3-MMP  332 RPS--------YPGAKPNICDGNFNTLAILRREMFVFKDQWFWRVRNNR- 372
                  *   *   *..* .* * * ** ***.

MT4-MMP  279 LVSLQPAQMHRFWRGLPLHLDSVDAVYERTSDHKIVFFKGDRYWVFKDNN 328

F06B09   348 LVSPRPARLHRFWEGLPAQVRVVQAAYARHRDGRILLFSGPQFWVFQDR- 396

MT2-MMP  295 VLDNYPMPIGHFWRGLPGDIS---AAYERQ-DGRFVFFKGDRYWLFREAN 340

MT1-MMP  349 VMDGYPMPIGQFWRGLPASIN---TAYERK-DGKFVFFKGDKHWVFDEAS 394

MT3-MMP  373 VMDGYPMQITYFWRGLPPSID---AVYENS-DGNFVFFKGNKYWVFKDTT 418
             ..  *  .  **  ***  .   . *  . * . * * .*.* .

MT4-MMP  329 VEEGYPRPVSDFSLP--PGG-IDAAFSWAHNDRTYFFKDQLYWRYDDHTR 375

F06B09   397 QLEGGARPLTELGLP--PGEEVDAVFSWPQNGKTYLVRGRQYWRYDEAAA 444

MT2-MMP  341 LEPGYPQPLTSYGL-GIPYDRIDTAIWWEPTGHTFFFQEDRYWRFNEETQ 389

MT1-MMP  395 LEPGYPKHIKELGR-GLPTDKIDAALFWMPNGKTYFFRGNKYYRFNEELR 443

MT3-MMP  419 LQPGYPHDLITLGS-GIPPHGIDSAIWWEDVGKTYFFKDRYWRYSEEMK 467
              *  ..       * .*. *   .*. .   * *..

MT4-MMP  376 HMDPGYPAQSPLWRGVPSTLDDAMRWS-DGASYFFRGQEYWKVLDGELEV 424

F06B09   445 RPDPGYPRDLSLWEGAPPSPDDVTVSN-AGDTYFFKGAHYWRFPKNSIKT 493

MT2-MMP  390 RGDPGYPKPISVWQGIPASPKGAFLSNDAAYTYFYKGTKYWKFDNERLRM 439

MT1-MMP  444 AVDSEYPKNIKVWEGIPESPRGSFMGSDEVFTYFYKGNKYWKFNNQKLKV 493

MT3-MMP  468 TMDPGYPKPITVWKGIPESPQGAFVHKENGFTYFYKGKEYWKFNNQILKV 517
              * **   .* * *.        .**..* **.     .

MT4-MMP  425 APGYPQSTARDWLVCGDSQADGSVAAGV-------DAAEGPRAPPGQHDQ 467

F06B09   494 EPDAPQPMGPNWLDCPAP-------------------SSGPRAP----RP 520

MT2-MMP  440 EPGYPKSILRDFMGCQEHVEPGPRWPDVARPPFNPHGGAEPGADSAEGDV 489
```

TABLE 2-continued

Comparison of various MMPs with F06B09. MT4-MMP (SEQ ID NO: 7) is from Genbank 3466295 (EMBL X89576); MT2-MMP (SEQ ID NO: 8) Z48482); MT1-MMP (SEQ ID NO: 9) is from Genbank 804994 (EMBL X83535; see also Genbank 1495995 (EMBL X90925) and 793763 (DDBJ D26512); and MT3-MMP (SEQ ID NO: 10) is from Genbank 2424979 (DDBJ D85511).

```
MT1-MMP  494  EPGYPKSALRDWMGCPSGGRPDE--------------GTEEETEVIIIEV  529

MT3-MMP  518  EPGYPRSILKDFMGCDGPTDRVKEG------------HSPPDDVDIVIKL  555
               *  *.     . *

MT4-MMP  468  SRS--------------------EDGYEVCSCTSGASSPPGAPGPLVAAT  497

F06B09   521  PKA--------------------TPVSETCDCQCELN---QAAGRWPAPI  547

MT2-MMP  490  GDGDGDFGAGVNKDRGSRVVVQMEEVARTVNVVMVLVPLLLLLCVLGLTY  539

MT1-MMP  530  D---------------------EEGGGAVSAAAVVLPVLLLLLVLAVGL  557

MT3-MMP  556  DN----------------------TASTVKAIAIVIPCILALCLLVLVY  582

MT4-MMP  498  MLLLLP-PLSPGALWTAAQALTL                            519

F06B09   548  PLLLLP-LLVGGVASR                                   562

MT2-MMP  540  ALVQMQRKGAPRVLLYCKRSLQEWV                          564

MT1-MMP  558  AVFFFRRHGTPRRLLYCQRSLLDKV                          582

MT3-MMP  583  TVFQFKRKGTPRHILYCKRSMQEWV                          607
```

In the search for DC specific genes, a novel matrix-metalloproteinase homologue (MMP) from the Memrbrane-type Matrix Metalloproteinases (MT-MMP) family subclass was identified. Of interest, this novel gene designated F06B09 is predominantly expressed by both CD34$^+$- and monocyte-derived DC and is down-regulated after DC maturation by CD40L L cells. The deduced protein sequence of F06B09 is clearly a member of the MMP family, characterized by the presence of a prodomain with the activation locus containing the essential cysteine residue, a catalytic domain including the zinc-binding site with the consensus sequence HExGHxxxxxH and an hemopexin-like domain (Birkedal-Hansen (1995) Curr. Opin. Cell Biol. 7:728–735; Shapiro (1998) Curr. Opin. Cell Biol. 10:602–608). MMPs belonging to the metzincin (or Clan) superfamily, can be classified into at least four subfamilies of closely related members: collagenases, stromelysins, gelatinases, and MT-MMP, although there are some MMPs like the macrophage metalloelastase (Belaaouaj, et al. (1995) J. Biol. Chem. 270:14568–14575) and the stromelysin 3 (Basset, et al. (1990) Nature 348:699–704) that do not belong to these subclasses. According to its structural characteristic and its high level of homology with MT4-MMP (Puente, et al. (1996) Cancer Res. 56:944–949), F06B09 represents the fifth member of the MT-MMP subclass. All MT-MMPs present a putative transmembrane domain in the C-terminal portion and a characteristic insertion between the propeptide and the catalytic domain containing the consensus amino acid sequence RxK/RR (Basbaum and Werb (1996) Curr. Opin. Cell Biol. 8:731–738). In order to activate MT-MMPs, this site is cleaved by enzymes called furin. Like other MMPs or matrixins, the novel 14T-MMP contains noncatalytic domains, in addition to the protease domain, which are likely involved in interactions with substrates or other proteins. MT-MMPs have the ability to cleave substrates, e.g., other MMPs. Effectively, MT1-, MT2- and MT3-MMP can activate proMMP2 (progelatinase A) into MMP2 on the cell surface (Butler, et al. (1997) Eur. J. Biochem. 244:653–657; Knauper, et al. (1996) J. Biol. Chem. 271:17124–17131; Kolkenbrock, et al. (1997) Biol. Chem. 378:71–76; Sato, et al. (1994) Nature 370:61–65; Strongin, et al. (1993) J. Biol. Chem. 268:14033–14039; and Takino, et al. (1995) J. Biol. Chem. 270:23013–23020), which as an active form degrades type IV collagen, the major component of basement membranes (Wilhelm, et al. (1989) J. Biol. Chem. 264:17213–17221). Thus, active MMP-2 (gelatinase A) plays a key role in the invasion of migrating cells into tissues. Several reports demonstrate that an overexpression of MMPs, especially MMP-2 and MMP-9, is associated with the invasive behavior of tumor cells (Shapiro (1998) Curr. Opin. Cell Biol. 10:602–608; Stetler-Stevenson, et al. (1993) Annu. Rev. Cell Biol. 9:541–573). Concerning the MT4-MMP, the most homologous gene to F06B09, it is uncertain whether this MT-MMP can activate proMMP-2. Phylogenetic analysis shows that among the MT-MMPs, MT4-MMP and F06B09 are distinguished from others and form a group of closely related proteins. It is speculated that these two MT-MMP share similar biological activities. It has been shown than MT-MMPs are overexpressed in cancers; in particular, high levels of MT1-MMP are associated with invasiveness of cervical cancer cells (Gilles, et al. (1996) Int. J. Cancer. 65:209–213), breast, colon, neck and lung carcinomas (Okada, et al. (1995) Proc. Natl. Acad. Sci. USA. 92:2730–2734; Sato, et al. (1994) Nature 370:61–65; Ueno, et al. (1997) Cancer Res. 57:2055–2060) and gastric cancers (Mori, et al. (1997) Int. J. Cancer. 74:316–321). Furthermore, MT4-MMP was isolated from a breast carcinoma (Puente, et al. (1996) Cancer Res. 56:944–949). Interestingly, the novel MT-MMP identified in the present report constitutes the first MT-MMP isolated from a DC library. It will be interesting to further study F06B09 expression in pathological tissues.

MT-MMP participate not only to the control of cell migration and tissue remodeling through their involvement in degradation of extracellular matrix and basement membranes, but also in the processing of pro-enzymes and pro-cytokines.

Of note, the genes for human MT1-MMP, 2, and 3 have been localized on three different chromosomes by in situ hybridization (Mattei, et al. (1997) *Genomics*. 40:168–169; Mignon, et al. (1995) *Genomics*. 28:360–361), and while the novel MT-MMP gene is on the same chromosome as MT2-MMP, both genes are on different loci: MT2-MMP is on chromosome 16q12 (Mattei, et al. (1997) *Genomics*. 40:168–169; Yasumitsu, et al. (1997) DNA Res. 4:77–79), and the novel MT-MMP is on chromosome 16p13.3.

The predominant expression of F06B09 in immature DC, and its putative membrane localization, suggests a role for this MT-MMP in degradation of extracellular matrix during DC migration. Furthermore, like MT1-MMP, which may trigger invasion by tumor cells by activating progelatinase A on tumor cell surface, this novel MT-MMP could be involved in cancer invasion.

The proteins of this invention are defined in part by their sequences, and by their physicochemical and biological properties. The biological properties of the human proteases described herein, e.g., human F06B09, are defined by their amino acid sequences, and mature sizes. They also should share certain biological enzymatic properties of their respective proteins.

The human protease F06B09 translation product exhibits structural motifs of a member of the matrix metalloproteinase family of proteases, more specifically to a family of matrix degrading proteinases. These proteins, in the latent form, typically possess a prodomain form which masks the catalytic site, which chelates a zinc ion. See Vallee and Auld (1990) *Biochemistry* 29:5647–5659. The processed mature protein is typically a potent cell-matrix degrading enzyme. See, e.g., Birkedal-Hansen (1990) *Proc. Nat'l. Acad. Sci. USA* 87:5578–5582. The enzyme may remain attached to the cell membrane after activation, and many of these proteases may localize to the leading cellular processes when the cell migrates. This may suggest other protein-protein interactions, e.g., with domains which specifically localize the enzymes by cytoskeletal or other mechanisms.

The pro-enzyme activation (furin) site would correspond to the Arg stretch from 86–90 of SEQ ID NO: 2; or 212–222 of SEQ ID NO: 4. It is likely that the activating enzyme will be one of the furin/PACE proteases, which are essentially ubiquitously expressed. By analogy to the MT1-MMP, these proteases activate other proteases, e.g., gelatinase A, collagenases, and others, that assist in the degradation of the extracellular matrix. See, e.g., Basbaum and Werb (1996) Current Opinion in Cell Biology 8:731–738.

F06B09 contains the zinc binding peptide consensus at about residues 212–222 of SEQ ID NO: 4, with characteristic His residues at 212, 216, and 222. There is also a hemopexin-like domain at about residues 291–525 and a matrixin-like domain corresponding to about residues 1–211. Natural substrates for the proteinase may be identified using standard methods. Substrate sequence specificity may be determined, and search for such sequences in databases may identify specific candidates for physiological substrates.

One of skill will readily recognize that some sequence variations may be tolerated, e.g., conservative substitutions or positions remote from the critical helical structures and remote from the identified or consensus critical active site regions, without altering significantly the biological activity of each respective molecule.

F06B09 proteins are present in specific cell types, e.g., dendritic cells, and the interaction of the protease with a substrate will be important for mediating various aspects of cellular physiology or development. The cellular types which express messages encoding F06B09 suggest that signals important in cell differentiation and development are mediated by them. See, e.g., Gilbert (1991) *Developmental Biology* (3d ed.) Sinauer Associates, Sunderland, Mass.; Browder, et al. (1991) Developmental Biology (3d ed.) Saunders, Philadelphia, Pa.; Russo, et al. (1992) *Development: The Molecular Genetic Approach* Springer-Verlag, New York, N.Y.; and Wilkins (1993) *Genetic Analysis of Animal Development* (2d ed.) Wiley-Liss, New York, N.Y. In particular, the proteases may be necessary for the conversion of pro-proteins to proteins, e.g., cytokine or protein precursors to mature forms, or for proper immunological function, e.g., antigen processing and presentation. Alternatively, the proteases may be important in dendritic cell trafficking, e.g., to traverse through extracellular matrix or vascular surfaces.

II. Definitions

The term "binding composition" refers to molecules that bind with specificity to F06B09, e.g., in an antibody-antigen interaction. However, other compounds, e.g., complex associated proteins, may also specifically associate with F06B09 to the exclusion of other molecules. Typically, the association will be in a natural physiologically relevant protein-protein interaction, either covalent or non-covalent, and may include members of a multiprotein complex, including carrier compounds or dimerization partners. The molecule may be a polymer, or chemical reagent. A functional analog may be a protease with structural modifications, or may be a wholly unrelated molecule, e.g., which has a molecular shape which interacts with the appropriate substrate cleavage determinants.

The term "binding agent: F06B09 protein complex", as used herein, refers to a complex of a binding agent and an F06B09 protein that is formed by specific binding of the binding agent to the F06B09 protein. Specific binding of the binding agent means that the binding agent has a specific binding site that recognizes a site on the F06B09 protein, typically in the native conformation, but possibly in a denatured conformation, e.g., a Western blot. For example, antibodies raised to an F06B09 protein and recognizing an epitope on the F06B09 protein are capable of forming a binding agent:F06B09 protein complex by specific binding. Typically, the formation of a binding agent: F06B09 protein complex allows the measurement of F06B09 protein in a biological sample, e.g., a mixture with other proteins and biologics. The term "antibody: F06B09 protein complex" refers to an embodiment in which the binding agent is an antibody. The antibody may be monoclonal, polyclonal, or a binding fragment of an antibody, e.g., an Fab, F(ab)2, or Fv fragment. The antibody will preferably be a polyclonal antibody for cross-reactivity determinations.

"Homologous" nucleic acid sequences, when compared, exhibit significant similarity or identity. The standards for homology in nucleic acids are either measures for homology generally used in the art by sequence comparison and/or phylogenetic relationship, or based upon hybridization conditions. Hybridization conditions are described in greater detail below.

An "isolated" nucleic acid is a nucleic acid, e.g., an RNA, DNA, or a mixed polymer, which is substantially separated from other biologic components which naturally accompany a native sequence, e.g., proteins and flanking genomic sequences from the originating species. The term embraces a nucleic acid sequence which has been removed from its naturally occurring environment, and includes recombinant or cloned DNA isolates and chemically synthesized analogs, or analogs biologically synthesized by heterologous systems. A substantially pure molecule includes isolated forms of the molecule. An isolated nucleic acid will usually contain homogeneous nucleic acid molecules, but will, in some embodiments, contain nucleic acids with minor sequence heterogeneity. This heterogeneity is typically found at the polymer ends or portions not critical to a desired biological function or activity.

As used herein, the term "F06B09" protein shall encompass, when used in a protein context, a protein having amino acid sequences, particularly from the protein motif portions, shown in SEQ ID NO: 2 or 4, respectively. In many contexts, a significant fragment of such a protein will be functionally equivalent. The invention also embraces a polypeptide which exhibits similar structure to human F06B09 protein, e.g., which interacts with F06B09 specific binding components. These binding components, e.g., antibodies, typically bind to F06B09 protein with high affinity, e.g., at least about 100 nM, usually better than about 30 nM, preferably better than about 10 nM, and more preferably at better than about 3 nM.

The term "polypeptide" or "protein" as used herein includes a significant fragment or segment of protease motif portion of F06B09 protein, and encompasses a stretch of amino acid residues of at least about 8 amino acids, generally at least about 10 amino acids, more generally at least about 12 amino acids, often at least about 14 amino acids, more often at least about 16 amino acids, typically at least about 18 amino acids, more typically at least about 20 amino acids, usually at least about 22 amino acids, more usually at least about 24 amino acids, preferably at least about 26 amino acids, more preferably at least about 28 amino acids, and, in particularly preferred embodiments, at least about 30 or more amino acids, e.g., 35, 40, 45, 50, 60, 70, 80, 100, etc. Preferred ends of such polypeptides will correspond to a motif or boundary described above, e.g., in Table 1. Preferably, a polypeptide will contain a plurality of distinct, e.g., discrete or nonoverlapping, segments of the specified length. Typically, the plurality will be at least two, more usually at least three, and preferably 5, 7, or even more. While the length minima are provided, longer lengths, of various sizes, may be appropriate, e.g., one of length 7, and two of length 12.

A "recombinant" nucleic acid is defined either by its method of production or its structure. In reference to its method of production, e.g., a product made by a process, the process is use of recombinant nucleic acid techniques, e.g., involving human intervention in the nucleotide sequence, typically selection or production. Alternatively, it can be a nucleic acid made by generating a sequence comprising fusion of two fragments which are not naturally contiguous to each other, but is meant to exclude products of nature, e.g., naturally occurring mutants. Thus, for example, products made by transforming cells with any non-naturally occurring vector is encompassed, as are nucleic acids comprising sequence derived using any synthetic oligonucleotide process. Such is often done to replace a codon with a redundant codon encoding the same or a conservative amino acid, while typically introducing or removing a sequence recognition site. Alternatively, it is performed to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. Specifically included are synthetic nucleic acids which, by genetic code redundancy, encode polypeptides similar to fragments of these antigens, and fusions of sequences from various different species variants.

"Solubility" is reflected by sedimentation measured in Svedberg units, which are a measure of the sedimentation velocity of a molecule under particular conditions. The determination of the sedimentation velocity was classically performed in an analytical ultracentrifuge, but is typically now performed in a standard ultracentrifuge. See, Freifelder (1982) *Physical Biochemistry* (2d ed.) W. H. Freeman & Co., San Francisco, Calif.; and Cantor and Schimmel (1980) *Biophysical Chemistry* parts 1–3, W. H. Freeman & Co., San Francisco, Calif. As a crude determination, a sample containing a putatively soluble polypeptide is spun in a standard full sized ultracentrifuge at about 50 K rpm for about 10 minutes, and soluble molecules will remain in the supernatant. A soluble particle or polypeptide will typically be less than about 30 S, more typically less than about 15 S, usually less than about 10 S, more usually less than about 6 S, and, in particular embodiments, preferably less than about 4S, and more preferably less than about 3S. Solubility of a polypeptide or fragment depends upon the environment and the polypeptide. Many parameters affect polypeptide solubility, including temperature, electrolyte environment, size and molecular characteristics of the polypeptide, and nature of the solvent. Typically, the temperature at which the polypeptide is used ranges from about 40° C. to about 65° C. Usually the temperature at use is greater than about 18° C. and more usually greater than about 22° C. For diagnostic purposes, the temperature will usually be about room temperature or warmer, but less than the denaturation temperature of components in the assay. For therapeutic purposes, the temperature will usually be body temperature, typically about 37° C. for humans, though under certain situations the temperature may be raised or lowered in situ or in vitro.

The size and structure of the polypeptide should generally be in a substantially stable state, and usually not in a denatured state. The polypeptide may be associated with other polypeptides in a quaternary structure, e.g., to confer solubility, or associated with lipids or detergents in a manner which approximates natural lipid bilayer interactions.

The solvent will usually be a biologically compatible buffer, of a type used for preservation of biological activities, and will usually approximate a physiological solvent. Usually the solvent will have a neutral pH, typically between about 5 and 10, and preferably about 7.5. On some occasions, a detergent will be added, typically a mild nondenaturing one, e.g., CHS (cholesteryl hemisuccinate) or CHAPS (3-[3-cholamidopropyl)-dimethylammonio]-1-propane sulfonate), or a low enough concentration as to avoid significant disruption of structural or physiological properties of the protein.

"Substantially pure" in a protein context typically means that the protein is isolated from other contaminating proteins, nucleic acids, and other biologicals derived from the original source organism. Purity, or "isolation" may be assayed by standard methods, and will ordinarily be at least about 50% pure, more ordinarily at least about 60% pure, generally at least about 70% pure, more generally at least about 80% pure, often at least about 85% pure, more often at least about 90% pure, preferably at least about 95% pure, more preferably at least about 98% pure, and in most preferred embodiments, at least 99% pure. Similar concepts apply, e.g., to antibodies or nucleic acids.

"Substantial similarity" in the nucleic acid sequence comparison context means either that the segments, or their complementary strands, when compared, are identical when optimally aligned, with appropriate nucleotide insertions or deletions, in at least about 50% of the nucleotides, generally at least about 56%, more generally at least about 59%, ordinarily at least about 62%, more ordinarily at least about 65%, often at least about 68%, more often at least about 71%, typically at least about 74%, more typically at least about 77%, usually at least about 80%, more usually at least about 85%, preferably at least about 90%, more preferably at least about 95 to 98% or more, and in particular embodiments, as high at about 99% or more of the nucleotides. Alternatively, substantial similarity exists when the segments will hybridize under selective hybridization conditions, to a strand, or its complement, typically using a sequence derived from SEQ ID NO: 1 or 3. Typically, selective hybridization will occur when there is at least about 55% similarity over a stretch of at least about 30 nucleotides, preferably at least about 65% over a stretch of at least about 25 nucleotides, more preferably at least about 75%, and most preferably at least about 90% over about 20 nucleotides. See Kanehisa (1984) *Nucl. Acids Res.* 12:203–213. The length of similarity comparison, as described, may be over longer stretches, and in certain embodiments will be over a stretch of at least about 17 nucleotides, usually at least about 20 nucleotides, more usually at least about 24 nucleotides, typically at least about 28 nucleotides, more typically at least about 40 nucleotides, preferably at least about 50 nucleotides, and more preferably at least about 75 to 100 or more nucleotides, e.g., 150, 200, etc. Various combinations of plurality of such segments will also be made.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optical alignment of sequences for comparison can be conducted, e.g., by the local homology algorithm of Smith and Waterman (1981) *Adv. Appl. Math.* 2:482, by the homology alignment algorithm of Needlman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng and Doolittle (1987) *J. Mol. Evol.* 35:351–360. The method used is similar to the method described by Higgins and Sharp (1989) *CABIOS* 5:151–153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described Altschul, et al. (1990) *J. Mol. Biol.* 215:403–410. Software for performing BLAST analyses is publicly available through the National Center for Biotechnology Information (http:www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul, et al., supra). These initial neighborhood word hits act as seeds for initiating searches to find longer HSPs containing them. The word hits are then extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff and Henikoff (1989) *Proc. Nat'l. Acad. Sci. USA* 89:10915) alignments (B) of 50, expectation (E) of 10, M=5, N=4, and a comparison of both strands.

In addition to calculating percent sequence identity, the BLAST algorithm also performs a statistical analysis of the similarity between two sequences (see, e.g., Karlin and Altschul (1993) *Proc. Nat'l. Acad. Sci. USA* 90:5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences of polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

"Stringent conditions", in referring to homology or substantial similarity in the hybridization context, will be stringent combined conditions of salt, temperature, organic solvents, and other parameters, typically those controlled in hybridization reactions. The combination of parameters is generally more important than the measure of any single parameter. See, e.g., Wetmur and Davidson (1968) *J. Mol. Biol.* 31:349–370. A nucleic acid probe which binds to a target nucleic acid under stringent conditions is specific for said target nucleic acid. Such a probe is typically more than 11 nucleotides in length, and is sufficiently identical or complementary to a target nucleic acid over the region specified by the sequence of the probe to bind the target under stringent hybridization conditions. Hybridization under stringent conditions should give a background of at least 2-fold over background, preferably at least 3–5 or more.

F06B09 proteins from other mammalian species can be cloned and isolated by cross-species hybridization of closely related species. See, e.g., below. Similarity may be relatively low between distantly related species, and thus hybridization of relatively closely related species is advisable. Alternatively, preparation of an antibody preparation which exhibits less species specificity may be useful in expression cloning approaches.

The phrase "specifically binds to an antibody" or "specifically immunoreactive with", when referring to a protein or peptide, refers to a binding reaction which is determinative of the presence of the protein in the presence of a heterogeneous population of proteins and other biological components. Thus, under designated immunoassay conditions, the specified antibodies bind to a particular protein and do not significantly bind other proteins present in the sample. Specific binding to an antibody under such conditions may require an antibody that is selected for its specificity for a particular protein. For example, antibodies raised to the human F06B09 protein immunogen with the amino acid sequence depicted in SEQ ID NO: 2 or 4 can be selected by immunoaffinity or similar methods to obtain antibodies specifically immumoreactive with F06B09 proteins and not with other proteins.

III. Nucleic Acids

F06B09 proteins are exemplary of larger classes of structurally and functionally related proteins. The F06B09 proteins will typically serve to cleave or process various proteins produced or processed by various cell types, e.g., for antigen presentation. The preferred embodiments, as disclosed, will be useful in standard procedures to isolate genes from different individuals or other species, e.g., warm blooded animals, such as birds and mammals. Cross hybridization will allow isolation of related genes encoding proteins from individuals, strains, or species. A number of different approaches are available to successfully isolate a suitable nucleic acid clone based upon the information provided herein. Southern blot hybridization studies can qualitatively determine the presence of homologous genes in human, monkey, rat, dog, cow, and rabbit genomes under specific hybridization conditions.

Complementary sequences will also be used as probes or primers. Based upon identification of the likely amino terminus, other peptides should be particularly useful, e.g., coupled with anchored vector or poly-A complementary PCR techniques or with complementary DNA of other peptides.

Techniques for nucleic acid manipulation of genes encoding F06B09 proteins, such as subcloning nucleic acid sequences encoding polypeptides into expression vectors, labeling probes, DNA hybridization, and the like are described generally in Sambrook, et al. (1989) *Molecular Cloning: A Laboratory Manual* (2nd ed.) Vol. 1–3, Cold Spring Harbor Laboratory, Cold Spring Harbor Press, NY, which is incorporated herein by reference. This manual is hereinafter referred to as "Sambrook, et al."

There are various methods of isolating DNA sequences encoding F06B09 proteins. For example, DNA is isolated from a genomic or cDNA library using labeled oligonucleotide probes having sequences identical or complementary to the sequences disclosed herein. Full-length probes may be used, or oligonucleotide probes may be generated by comparison of the sequences disclosed. Such probes can be used directly in hybridization assays to isolate DNA encoding F06B09 proteins, or probes can be designed for use in amplification techniques such as PCR, for the isolation of DNA encoding F06B09 proteins.

To prepare a cDNA library, mRNA is isolated from cells, preferably which express high levels of an F06B09 protein. cDNA is prepared from the mRNA and ligated, e.g., into a recombinant vector. The vector is transfected into a recombinant host for propagation, screening, and cloning. Methods for making and screening cDNA libraries are well known. See Gubler and Hoffman (1983) *Gene* 25:263–269 and Sambrook, et al.

For a genomic library, the DNA can be extracted from tissue, and often either mechanically sheared or enzymatically digested to yield fragments of about 12–20 kb. The fragments are then separated by gradient centrifugation and cloned in bacteriophage lambda vectors. These vectors and phage are packaged in vitro, as described in Sambrook, et al. Recombinant phage are analyzed by plaque hybridization as described in Benton and Davis (1977) *Science* 196:180–182. Colony hybridization is carried out as generally described in, e.g., Grunstein, et al. (1975) *Proc. Natl. Acad. Sci. USA.* 72:3961–3965.

DNA encoding an F06B09 protein can be identified in either cDNA or genomic libraries by its ability to hybridize with the nucleic acid probes described herein, e.g., in colony or plaque hybridization assays. The corresponding DNA regions are isolated, e.g., by standard methods familiar to those of skill in the art. See, e.g., Sambrook, et al.

Various methods of amplifying target sequences, such as the polymerase chain reaction, can also be used to prepare DNA encoding F06B09 proteins. Polymerase chain reaction (PCR) technology may be used to amplify such nucleic acid sequences directly from mRNA, from cDNA, and/or from genomic libraries or cDNA libraries. The isolated sequences encoding F06B09 proteins may also be used as templates for PCR amplification.

Typically, in PCR techniques, oligonucleotide primers complementary to two flanking regions in the DNA region to be amplified are synthesized. The polymerase chain reaction is then carried out using the two primers. See Innis, et al. (eds. 1990) *PCR Protocols: A Guide to Methods and Applications* Academic Press, San Diego, Calif. Primers can be selected to amplify the entire regions encoding a full-length human F06B09 protein or to amplify smaller DNA segments, as desired. Once such regions are PCR-amplified, they can be sequenced and oligonucleotide probes can be prepared from sequence obtained using standard techniques. These probes can then be used to isolate DNA's encoding F06B09 proteins.

Oligonucleotides for use as probes are usually chemically synthesized according to the solid phase phosphoramidite triester method first described by Beaucage and Carruthers (1983) *Tetrahedron Lett.* 22(20):1859–1862, or using an automated synthesizer, as described in Needham-VanDevanter, et al. (1984) *Nucleic Acids Res.*

12:6159–6168. Purification of oligonucleotides is performed e.g., by native acrylamide gel electrophoresis or by anion-exchange HPLC as described in Pearson and Regnier (1983) *J. Chrom.* 255:137–149. The sequence of the synthetic oligonucleotide can be verified using, e.g., the chemical degradation method of Maxam, A. M. and Gilbert, W. in Grossman and Moldave (eds. 1980) *Methods in Enzymology* 65:499–560, Academic Press, New York.

An isolated nucleic acid encoding a human F06B09 protein was identified. The nucleotide sequence, corresponding open reading frames, and mature peptides are provided in Table 1 or SEQ ID NO: 1 or 3.

This invention provides isolated DNA or fragments to encode an F06B09 protein or specific fragment thereof. In addition, this invention provides isolated or recombinant DNA which encodes a protein or polypeptide, and which is capable of hybridizing under appropriate conditions, e.g., high stringency, with the DNA sequences described herein. Said biologically active protein or polypeptide can be a functional protease segment, or fragment, and have an amino acid sequence as disclosed in SEQ ID NO: 2 or 4. Preferred embodiments will be full length natural sequences, from isolates, or proteolytic fragments thereof. Further, this invention contemplates the use of isolated or recombinant DNA, or fragments thereof, which encode proteins which exhibit high measures of identity to an F06B09 protein, or which were isolated, e.g., using cDNA encoding an F06B09 protease polypeptide as a probe. The isolated DNA can have the respective regulatory sequences in the 5' and 3' flanks, e.g., promoters, enhancers, poly-A addition signals, and others.

IV. Making Human F06B09 Proteins

DNAs which encode an F06B09 protein, or fragments thereof, can be obtained by chemical synthesis, screening cDNA libraries, or by screening genomic libraries prepared from a wide variety of cell lines or tissue samples.

These DNAs can be expressed in a wide variety of host cells for the synthesis of a full-length protein or fragments which can in turn, e.g., be used to generate polyclonal or monoclonal antibodies; for binding studies; for construction and expression of modified molecules; and for structure/function studies. Each of F06B09, or their fragments, can be expressed in host cells that are transformed or transfected with appropriate expression vectors. These molecules can be substantially purified to be free of protein or cellular contaminants, other than those derived from the recombinant host, and therefore are particularly useful in pharmaceutical compositions when combined with a pharmaceutically acceptable carrier and/or diluent. The antigen, e.g., F06B09, or portions thereof, may be expressed as fusions with other proteins or possessing an epitope tag.

Expression vectors are typically self-replicating DNA or RNA constructs containing the desired antigen gene or its fragments, usually operably linked to appropriate genetic control elements that are recognized in a suitable host cell. The specific type of control elements necessary to effect expression will depend upon the eventual host cell used. Generally, the genetic control elements can include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also usually contain an origin of replication that allows the vector to replicate independently from the host cell.

The vectors of this invention contain DNAs which encode an F06B09 protein, or a significant fragment thereof, typically encoding, e.g., a biologically active polypeptide, or protein. The DNA can be under the control of a viral promoter and can encode a selection marker. This invention further contemplates use of such expression vectors which are capable of expressing eukaryotic cDNA coding for an F06B09 protein in a prokaryotic or eukaryotic host, where the vector is compatible with the host and where the eukaryotic cDNA coding for the protein is inserted into the vector such that growth of the host containing the vector expresses the cDNA in question. Usually, expression vectors are designed for stable replication in their host cells or for amplification to greatly increase the total number of copies of the desirable gene per cell. It is not always necessary to require that an expression vector replicate in a host cell, e.g., it is possible to effect transient expression of the protein or its fragments in various hosts using vectors that do not contain a replication origin that is recognized by the host cell. It is also possible to use vectors that cause integration of an F06B09 protein gene or its fragments into the host DNA by recombination, or to integrate a promoter which controls expression of an endogenous gene.

Vectors, as used herein, contemplate plasmids, viruses, bacteriophage, integratable DNA fragments, and other vehicles which enable the integration of DNA fragments into the genome of the host. Expression vectors are specialized vectors which contain genetic control elements that effect expression of operably linked genes. Plasmids are the most commonly used form of vector, but many other forms of vectors which serve an equivalent function are suitable for use herein. See, e.g., Pouwels, et al. (1985 and Supplements) *Cloning Vectors: A Laboratory Manual* Elsevier, N.Y.; and Rodriguez, et al. (eds. 1988) *Vectors: A Survey of Molecular Cloning Vectors and Their Uses* Buttersworth, Boston, Mass.

Suitable host cells include prokaryotes, lower eukaryotes, and higher eukaryotes. Prokaryotes include both gram negative and gram positive organisms, e.g., *E. coli* and *B. subtilis*. Lower eukaryotes include yeasts, e.g., S. cerevisiae and Pichia, and species of the genus Dictyostelium. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or its derivatives. Vectors that can be used to express F06B09 proteins or fragments thereof include, but are not limited to, such vectors as those containing the lac promoter (pUC-series); trp promoter (pBR322-trp); Ipp promoter (the pIN-series); lambda-pP or pR promoters (pOTS); or hybrid promoters such as ptac (pDR540). See Brosius, et al. (1988) "Expression Vectors Employing Lambda-, trp-, lac-, and Ipp-derived Promoters", in Rodriguez and Denhardt (eds.) *Vectors: A Survey of Molecular Cloning Vectors and Their Uses* 10:205–236 Buttersworth, Boston, Mass.

Lower eukaryotes, e.g., yeasts and Dictyostelium, may be transformed with F06B09 protein sequence containing vectors. For purposes of this invention, the most common lower eukaryotic host is the baker's yeast, Saccharomyces cerevisiae. It will be used generically to represent lower eukaryotes although a number of other strains and species will be essentially equivalent. Yeast vectors typically consist of a replication origin (unless of the integrating type), one or more selection genes, a promoter, DNA encoding the desired protein or its fragments, and sequences for translation termination, polyadenylation, and transcription termination. Suitable expression vectors for yeast include such constitutive promoters as 3-phosphoglycerate kinase and various other glycolytic enzyme gene promoters or such inducible promoters as the alcohol dehydrogenase 2 promoter or metallothionine promoter. Suitable vectors include derivatives of the following types: self-replicating low copy number (such as the YRp-series), self-replicating high copy number (such as the YEp-series), integrating types (such as the YIp-series), or mini-chromosomes (such as the YCp-series).

Higher eukaryotic tissue culture cells are typically the preferred host cells for expression of the functionally active F06B09 protease polypeptides. In principle, many higher eukaryotic tissue culture cell lines may be used, e.g., insect baculovirus expression systems, whether from an invertebrate or vertebrate source. However, mammalian cells are preferred to achieve proper natural processing, both cotranslationally and posttranslationally. Transformation or transfection and propagation of such cells are routine. Useful cell lines include HeLa cells, Chinese hamster ovary (CHO) cell lines, baby rat kidney (BRK) cell lines, insect cell lines, bird cell lines, and monkey (COS) cell lines. Expression vectors for such cell lines usually include an origin of replication, a promoter, a translation initiation site, RNA splice sites (e.g., if genomic DNA is used), a polyadenylation site, and a transcription termination site. These vectors also may contain selection and/or amplification genes. Suitable expression vectors may be plasmids, viruses, or retroviruses carrying promoters derived, e.g., from such sources as from adenovirus, SV40, parvoviruses, vaccinia virus, or cytomegalovirus. Representative examples of suitable expression vectors include pCDNA1; pCD, see Okayama, et al. (1985) *Mol. Cell Biol.* 5:1136–1142; pMC1neo Poly-A, see Thomas, et al. (1987) *Cell* 51:503–512; and a baculovirus vector such as pAC 373 or pAC 610.

It is likely that F06B09 protein need not be glycosylated to elicit biological responses. However, it will occasionally be desirable to express an F06B09 polypeptide in a system which provides a specific or defined glycosylation pattern. In this case, the usual pattern will be that provided naturally by the expression system. However, the pattern will be modifiable by exposing the polypeptide, e.g., in unglycosylated form, to appropriate glycosylating proteins introduced into a heterologous expression system. For example, an F06B09 protein gene may be co-transformed with one or more genes encoding mammalian or other glycosylating enzymes. It is further understood that over glycosylation may be detrimental to F06B09 protein biological activity, and that one of skill may perform routine testing to optimize the degree of glycosylation which confers optimal biological activity.

An F06B09 protein, or a fragment thereof, may be engineered to be phosphatidyl inositol (PI) linked to a cell membrane, but can be removed from membranes by treatment with a phosphatidyl inositol cleaving enzyme, e.g., phosphatidyl inositol phospholipase-C. This releases the antigen in a biologically active form, and allows purification by standard procedures of protein chemistry. See, e.g., Low (1989) *Biochem. Biophys. Acta* 988:427–454; Tse, et al. (1985) *Science* 230:1003–1008; and Brunner, et al. (1991) *J. Cell Biol.* 114:1275–1283.

Now that F06B09 proteins have been characterized, fragments or derivatives thereof can be prepared by conventional processes for synthesizing peptides. These include processes such as are described in Stewart and Young (1984) *Solid Phase Peptide Synthesis* Pierce Chemical Co., Rockford, Ill.; Bodanszky and Bodanszky (1984) *The Practice of Peptide Synthesis* Springer-Verlag, New York, N.Y.; Bodanszky (1984) *The Principles of Peptide Synthesis* Springer-Verlag, New York, N.Y.; and Dawson, et al. (1994) *Science* 266:776–779. For example, an azide process, an acid chloride process, an acid anhydride process, a mixed anhydride process, an active ester process (for example, p-nitrophenyl ester, N-hydroxysuccinimide ester, or cyanomethyl ester), a carbodiimidazole process, an oxidative-reductive process, or a dicyclohexylcarbodiimide (DCCD)/ additive process can be used. Solid phase and solution phase syntheses are both applicable to the foregoing processes.

The prepared protein and fragments thereof can be isolated and purified from the reaction mixture by means of peptide separation, for example, by extraction, precipitation, electrophoresis and various forms of chromatography, and the like. The F06B09 proteins of this invention can be obtained in varying degrees of purity depending upon its desired use. Purification can be accomplished by use of known protein purification techniques or by the use of the antibodies or binding partners herein described, e.g., in immunoabsorbant affinity chromatography. This immunoabsorbant affinity chromatography is carried out, e.g., by first linking the antibodies to a solid support and then contacting the linked antibodies with solubilized lysates of appropriate source cells, lysates of other cells expressing the ligand, or lysates or supernatants of cells producing the F06B09 proteins as a result of recombinant DNA techniques, see below.

Multiple cell lines may be screened for one which expresses an F06B09 polypeptide or protein at a high level compared with other cells. Various cell lines, e.g., a mouse thymic stromal cell line TA4, is screened and selected for its favorable handling properties. Natural F06B09 proteins can be isolated from natural sources, or by expression from a transformed cell using an appropriate expression vector. Purification of the expressed protein is achieved by standard procedures, or may be combined with engineered means for effective purification at high efficiency from cell lysates or supernatants. Epitope or other tags, e.g., FLAG or $His_6$ segments, can be used for such purification features.

V. Antibodies

Antibodies can be raised to various F06B09 proteins, including individual, polymorphic, allelic, strain, or species variants, and fragments thereof, both in their naturally occurring (full-length) forms and in their recombinant forms. Additionally, antibodies can be raised to F06B09 proteins in either their native (or active) forms or in their inactive, e.g., denatured, forms. Anti-idiotypic antibodies may also be used.

A. Antibody Production

A number of immunogens may be used to produce antibodies specifically reactive with F06B09 proteins. Recombinant protein is a preferred immunogen for the production of monoclonal or polyclonal antibodies. Naturally occurring protein may also be used either in pure or impure form. Synthetic peptides, made using the human F06B09 protein sequences described herein, may also used as an immunogen for the production of antibodies to F06B09 proteins. Recombinant protein can be expressed in eukaryotic or prokaryotic cells as described herein, and purified as described. Naturally folded or denatured material can be used, as appropriate, for producing antibodies. Either monoclonal or polyclonal antibodies may be generated, e.g., for subsequent use in immunoassays to measure the protein.

Methods of producing polyclonal antibodies are well known to those of skill in the art. Typically, an immunogen, preferably a purified protein, is mixed with an adjuvant and animals are immunized with the mixture. The animal's immune response to the immunogen preparation is monitored by taking test bleeds and determining the titer of reactivity to the F06B09 protein of interest. For example, when appropriately high titers of antibody to the immunogen are obtained, usually after repeated immunizations, blood is collected from the animal and antisera are prepared. Further fractionation of the antisera to enrich for antibodies reactive to the protein can be done if desired. See, e.g., Harlow and Lane; or Coligan.

Monoclonal antibodies may be obtained by various techniques familiar to those skilled in the art. Typically, spleen cells from an animal immunized with a desired antigen are immortalized, commonly by fusion with a myeloma cell (see, Kohler and Milstein (1976) *Eur. J. Immunol.* 6:511–519, incorporated herein by reference). Alternative methods of immortalization include transformation with Epstein Barr Virus, oncogenes, or retroviruses, or other methods known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according, e.g., to the general protocol outlined by Huse, et al. (1989) *Science* 246:1275–1281.

Antibodies, including binding fragments and single chain versions, against predetermined fragments of F06B09 proteins can be raised by immunization of animals with conjugates of the fragments with carrier proteins as described above. Monoclonal antibodies are prepared from cells secreting the desired antibody. These antibodies can be screened for binding to normal or defective F06B09 protein, or screened for agonistic or antagonistic activity, e.g., mediated through a receptor. These monoclonal antibodies will usually bind with at least a $K_D$ of about 1 mm, more usually at least about 300 $\mu$M, typically at least about 100 $\mu$M, more typically at least about 30 $\mu$M, preferably at least about 10 $\mu$M, and more preferably at least about 3 $\mu$M or better.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) *Basic and Clinical Immunology* (4th ed.) Lange Medical Publications, Los Altos, Calif., and references cited therein; Harlow and Lane (1988) *Antibodies: A Laboratory Manual* CSH Press; Goding (1986) *Monoclonal Antibodies: Principles and Practice* (2d ed.) Academic Press, New York, N.Y.; and particularly in Kohler and Milstein (1975) *Nature* 256:495–497, which discusses one method of generating monoclonal antibodies. Summarized briefly, this method involves injecting an animal with an immunogen. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve selection of libraries of antibodies in phage or similar vectors. See, e.g., Huse, et al. (1989) "Generation of a Large Combinatorial Library of the Immunoglobulin Repertoire in Phage Lambda," *Science* 246:1275–1281; and Ward, et al. (1989) *Nature* 341:544–546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see, Cabilly, U.S. Pat. No. 4,816,567; and Queen, et al. (1989) *Proc. Nat'l. Acad. Sci. USA* 86:10029–10033; or made in transgenic mice, see Mendez, et al. (1997) *Nature Genetics* 15:146–156.

The antibodies of this invention are useful for affinity chromatography in isolating F06B09 protein. Columns can be prepared where the antibodies are linked to a solid support, e.g., particles, such as agarose, SEPHADEX, or the like, where a cell lysate or supernatant may be passed through the column, the column washed, followed by increasing concentrations of a mild denaturant, whereby purified F06B09 protein will be released. The converse can be performed using protein to isolate specific antibodies.

Other antibodies may block enzymatic activity. The antibodies may also be used to screen expression libraries for particular expression products. Usually the antibodies used in such a procedure will be labeled with a moiety allowing easy detection of presence of antigen by antibody binding.

Antibodies to F06B09 proteins may be used for the identification of cell populations expressing F06B09 protein. By assaying the expression products of cells expressing F06B09 proteins it is possible to diagnose disease, e.g., metabolic conditions. The proteins may also be markers for specific tissue or cell subpopulations, e.g., dendritic cells.

Antibodies raised against each F06B09 protein will also be useful to raise anti-idiotypic antibodies. These will be useful in detecting or diagnosing various immunological conditions related to expression of the respective antigens.

B. Immunoassays

A particular protein can be measured by a variety of immunoassay methods. For a review of immunological and immunoassay procedures in general, see Stites and Terr (eds. 1991) *Basic and Clinical Immunology* (7th ed.). Moreover, the immunoassays of the present invention can be performed in many configurations, which are reviewed extensively in Maggio (ed. 1980) *Enzyme Immunoassay* CRC Press, Boca Raton, Fla.; Tijan (1985) "Practice and Theory of Enzyme Immunoassays," *Laboratory Techniques in Biochemistry and Molecular Biology*, Elsevier Science Publishers B.V., Amsterdam; and Harlow and Lane *Antibodies, A Laboratory Manual*, supra, each of which is incorporated herein by reference. See also Chan (ed. 1987) *Immunoassay: A Practical Guide* Academic Press, Orlando, Fla.; Price and Newman (eds. 1991) *Principles and Practice of Immunoassays* Stockton Press, NY; and Ngo (ed. 1988) *Non-isotopic Immunoassays* Plenum Press, NY.

Immunoassays for measurement of F06B09 proteins or peptides can be performed by a variety of methods known to those skilled in the art. In brief, immunoassays to measure the protein can be either competitive or noncompetitive binding assays. In competitive binding assays, the sample to be analyzed competes with a labeled analyte for specific binding sites on a capture agent bound to a solid surface. Preferably the capture agent is an antibody specifically reactive with F06B09 proteins produced as described above. The concentration of labeled analyte bound to the capture agent is inversely proportional to the amount of free analyte present in the sample.

In a competitive binding immunoassay, the F06B09 protein present in the sample competes with labeled protein for binding to a specific binding agent, for example, an antibody specifically reactive with the F06B09 protein. The binding agent may be bound to a solid surface to effect separation of bound labeled protein from the unbound labeled protein. Alternately, the competitive binding assay may be conducted in liquid phase and a variety of techniques known in the art may be used to separate the bound labeled protein from the unbound labeled protein. Following separation, the amount of bound labeled protein is determined. The amount of protein present in the sample is inversely proportional to the amount of labeled protein binding.

Alternatively, a homogeneous immunoassay may be performed in which a separation step is not needed. In these immunoassays, the label on the protein is altered by the binding of the protein to its specific binding agent. This alteration in the labeled protein results in a decrease or increase in the signal emitted by label, so that measurement of the label at the end of the immunoassay allows for detection or quantitation of the protein.

F06B09 proteins may also be determined by a variety of noncompetitive immunoassay methods. For example, a two-site, solid phase sandwich immunoassay may be used. In this type of assay, a binding agent for the protein, for example an antibody, is attached to a solid support. A second protein binding agent, which may also be an antibody, and which binds the protein at a different site, is labeled. After binding at both sites on the protein has occurred, the unbound labeled binding agent is removed and the amount of labeled binding agent bound to the solid phase is measured. The amount of labeled binding agent bound is directly proportional to the amount of protein in the sample.

Western blot analysis can be used to determine the presence of F06B09 proteins in a sample. Electrophoresis is carried out, for example, on a tissue sample suspected of containing the protein. Following electrophoresis to separate the proteins, and transfer of the proteins to a suitable solid support, e.g., a nitrocellulose filter, the solid support is incubated with an antibody reactive with the protein. This antibody may be labeled, or alternatively may be detected by subsequent incubation with a second labeled antibody that binds the primary antibody.

The immunoassay formats described above may employ labeled assay components. The label may be coupled directly or indirectly to the desired component of the assay according to methods well known in the art. A wide variety of labels and methods may be used. Traditionally, a radioactive label incorporating $^3$H, $^{125}$I, $^{35}$S, $^{14}$C, or $^{32}$P was used. Non-radioactive labels include ligands which bind to labeled antibodies, fluorophores, chemiluminescent agents, enzymes, and antibodies which can serve as specific binding pair members for a labeled ligand. The choice of label depends on sensitivity required, ease of conjugation with the compound, stability requirements, and available instrumentation. For a review of various labeling or signal producing systems which-may be used, see U.S. Pat. No. 4,391,904, which is incorporated herein by reference.

Antibodies reactive with a particular protein can also be measured by a variety of immunoassay methods. For a review of immunological and immunoassay procedures applicable to the measurement of antibodies by immunoassay techniques, see Stites and Terr (eds.) *Basic and Clinical Immunology* (7th ed.) supra; Maggio (ed.) *Enzyme Immunoassay*, supra; and Harlow and Lane *Antibodies, A Laboratory Manual*, supra.

In brief, inmunoassays to measure antisera reactive with F06B09 proteins can be either competitive or noncompetitive binding assays. In competitive binding assays, the sample analyte competes with a labeled analyte for specific binding sites on a capture agent bound to a solid surface. Preferably the capture agent is a purified recombinant F06B09 protein produced as described above. Other sources of F06B09 proteins, including isolated or partially purified naturally occurring protein, may also be used. Noncompetitive assays include sandwich assays, in which the sample analyte is bound between two analyte-specific binding reagents. One of the binding agents is used as a capture agent and is bound to a solid surface. The second binding agent is labeled and is used to measure or detect the resultant complex by visual or instrument means. A number of combinations of capture agent and labeled binding agent can be used. A variety of different immunoassay formats, separation techniques, and labels can be also be used similar to those described above for the measurement of F06B09 proteins. Similar methods may be used to evaluate or quantitate specific binding compounds.

VI. Purified F06B09 Proteins

Human F06B09 protein amino acid sequences are provided in Table 1 and SEQ ID NO: 2 or 4.

Purified protein or defined peptides are useful for generating antibodies by standard methods, as described above. Synthetic peptides or purified protein can be presented to an immune system to generate polyclonal and monoclonal antibodies. See, e.g., Coligan (1991) *Current Protocols in Immunology* Wiley/Greene, NY; and Harlow and Lane (1989) *Antibodies: A Laboratory Manual* Cold Spring Harbor Press, NY, which are incorporated herein by reference.

The specific binding composition can be used for screening an expression library made from a cell line which expresses an F06B09 protein. Many methods for screening are available, e.g., standard staining of surface expressed ligand, or by panning. Screening of intracellular expression can also be performed by various staining or immunofluorescence procedures. The binding compositions could be used to affinity purify or sort out cells expressing the ligand.

The peptide segments, along with comparison to homologous genes, can also be used to produce appropriate oligonucleotides to screen a library. The genetic code can be used to select appropriate oligonucleotides useful as probes for screening. In combination with polymerase chain reaction (PCR) techniques, synthetic oligonucleotides will be useful in selecting desired clones from a library, including natural allelic and polymorphic variants.

The peptide sequences allow preparation of peptides to generate antibodies to recognize such segments, and allow preparation of oligonucleotides which encode such sequences. The sequence also allows for synthetic preparation, e.g., see Dawson, et al. (1994) *Science* 266:776–779. Analysis of the structural features in comparison with the most closely related reported sequences has revealed similarities with other proteins, particularly the class of proteins known as proteases.

VII. Physical Variants

This invention also encompasses proteins or peptides having substantial amino acid sequence similarity with an amino acid sequence of an F06B09 protein. Natural variants include individual, polymorphic, allelic, strain, or species variants. Conservative substitutions in the amino acid sequence will normally preserve most relevant biological activities. In particular, various substitutions can be made, e.g., embodiments with 10-fold substitutions, 7-fold substitutions, 5-fold substitutions, 3-fold substitutions, 2-fold, and etc. Such embodiments will typically retain particular features, e.g., antigenicity, with the natural forms.

Amino acid sequence similarity, or sequence identity, is determined by optimizing residue matches, if necessary, by introducing gaps as required. This changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Homologous amino acid sequences include natural polymorphic, allelic, and interspecies variations in each respective protein sequence. Typical homologous proteins or peptides will have from 50–100% similarity (if gaps can be introduced), to 75–100% similarity (if conservative substitutions are included) with the amino acid sequence of the F06B09 protein. Similarity measures will be at least about 50%, generally at least about 60%, more generally at least about 65%, usually at least about 70%, more usually at least about 75%, preferably at least about 80%, and more preferably at least about 80%, and in particularly preferred embodiments, at least about 85% or more. See also Needleham, et al. (1970) *J. Mol. Biol.* 48:443–453; Sankoff, et al. (1983) *Time Warps, String Edits, and Macromolecules: The Theory and Practice of Sequence Comparison* Chapter One, Addison-Wesley, Reading, Mass.; and software packages from IntelliGenetics, Mountain View, Calif.; and the University of Wisconsin Genetics Computer Group, Madison, Wis.

Natural nucleic acids encoding mammalian F06B09 proteins will typically hybridize to the nucleic acid sequence of SEQ ID NO: 1 or 3 under stringent conditions. For example, nucleic acids encoding human F06B09 proteins will normally hybridize to the nucleic acid of SEQ ID NO: 1 or 3 under stringent hybridization conditions. Generally stringent conditions are selected to be about 10° C. lower than the thermal melting point (Tm) for the probe sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.2 molar at pH 7 and the temperature is at least about 50° C. Other factors may significantly affect the stringency of hybridization, including, among others, base composition and size of the complementary strands, the presence of organic solvents such as formamide, and the extent of base mismatching. A preferred embodiment will include nucleic acids which will bind to disclosed sequences in 50% formamide and 200 mM NaCl at 42° C. See, e.g., Sambrook, et al.

An isolated F06B09 protein DNA can be readily modified by nucleotide substitutions, nucleotide deletions, nucleotide insertions, and short inversions of nucleotide stretches. These modifications result in novel DNA sequences which encode F06B09 protein antigens, their derivatives, or proteins having highly similar physiological, immunogenic, or antigenic activity.

Modified sequences can be used to produce mutant antigens or to enhance expression. Enhanced expression may involve gene amplification, increased transcription, increased translation, and other mechanisms. Such mutant F06B09 protein derivatives include predetermined or site-specific mutations of the respective protein or its fragments. "Mutant F06B09 protein" encompasses a polypeptide otherwise falling within the homology definition of the human F06B09 protein as set forth above, but having an amino acid sequence which differs from that of an F06B09 protein as found in nature, whether by way of deletion, substitution, or insertion. In particular, "site specific mutant F06B09 protein" generally includes proteins having significant similarity with a protein having a sequence of SEQ ID NO: 2 or 4, and as sharing various biological activities, e.g., antigenic or immunogenic, with those sequences, and in preferred embodiments contain most or all of the disclosed sequence. This applies also to polymorphic variants from different individuals. Similar concepts apply to different F06B09 proteins, particularly those found in various warm blooded animals, e.g., mammals and birds. As stated before, it is emphasized that descriptions are generally meant to encompass other F06B09 proteins, not limited to the human embodiments specifically discussed.

Although site specific mutation sites are predetermined, mutants need not be site specific. F06B09 protein mutagenesis can be conducted by making amino acid insertions or deletions. Substitutions, deletions, insertions, or combinations may be generated to arrive at a final construct. Insertions include amino- or carboxyl-terminal fusions, e.g. epitope tags. Random mutagenesis can be conducted at a target codon and the expressed mutants can then be screened for the desired activity. Methods for making substitution mutations at predetermined sites in DNA having a known sequence are well known in the art, e.g., by M13 primer mutagenesis or polymerase chain reaction (PCR) techniques. See also, Sambrook, et al. (1989) and Ausubel, et al. (1987 and Supplements). The mutations in the DNA normally should not place coding sequences out of reading frames and preferably will not create-complementary regions that could hybridize to produce secondary mRNA structure such as loops or hairpins.

The present invention also provides recombinant proteins, e.g., heterologous fusion proteins using segments from these proteins. A heterologous fusion protein is a fusion of proteins or segments which are naturally not normally fused in the same manner. Thus, the fusion product of an immunoglobulin with an F06B09 protein polypeptide is a continuous protein molecule having sequences fused in a typical peptide linkage, typically made as a single translation product and exhibiting properties derived from each source peptide. A similar concept applies to heterologous nucleic acid sequences. Antibody fusion proteins are also contemplated.

In addition, new constructs may be made from combining similar functional domains from other proteins. For example, protein-binding or other segments may be "swapped" between different new fusion polypeptides or fragments. See, e.g., Cunningham, et al. (1989) *Science* 243:1330–1336; and O'Dowd, et al. (1988) *J. Biol. Chem.* 263:15985–15992. Thus, new chimeric polypeptides exhibiting new combinations of specificities will result from the functional linkage of protein-binding specificities and other functional domains.

VIII. Binding Agent:F06B09 Protein Complexes

An F06B09 protein that specifically binds to or that is specifically immunoreactive with an antibody generated against a defined immunogen, such as an immunogen consisting of the amino acid sequence of SEQ ID NO: 2 or 4, is typically determined in an immunoassay. The immunoassay uses a polyclonal antiserum which was raised to a protein of SEQ ID NO: 2 or 4. This antiserum is selected to have low crossreactivity against other proteases and any such crossreactivity is removed by immunoabsorption prior to use in the immunoassay.

In order to produce antisera for use in an immunoassay, the protein of SEQ ID NO: 2 or 4 is isolated as described herein. For example, recombinant protein may be produced in a mammalian cell line. An inbred strain of mice such as Balb/c is immunized with the protein of SEQ ID NO: 2 or 4 using a standard adjuvant, such as Freund's adjuvant, and a standard mouse immunization protocol (see Harlow and Lane, supra). Alternatively, a synthetic peptide, preferably near full length, derived from the sequences disclosed herein and conjugated to a carrier protein can be used an immunogen. Polyclonal sera are collected and titered against the immunogen protein in an immunoassay, for example, a solid phase immunoassay with the immunogen immobilized on a solid support. Polyclonal antisera with a titer of $10^4$ or greater are selected and tested for their cross reactivity against other proteases, e.g., using a competitive binding immunoassay such as the one described in Harlow and Lane, supra, at pages 570–573. Preferably two related proteins are used in this determination in conjunction with either F06B09 protein.

Immunoassays in the competitive binding format can be used for the crossreactivity determinations. For example, a protein of SEQ ID NO: 4 can be immobilized to a solid support. Proteins added to the assay compete with the binding of the antisera to the immobilized antigen. The ability of the above proteins to compete with the binding of the antisera to the immobilized protein is compared to the protein of SEQ ID NO: 4. The percent crossreactivity for the above proteins is calculated, using standard calculations. Those antisera with less than 10% crossreactivity with each of the proteins listed above are selected and pooled. The cross-reacting antibodies are then removed from the pooled antisera by immunoabsorption with the above-listed proteins.

The immunoabsorbed and pooled antisera are then used in a competitive binding immunoassay as described above to compare a second protein to the immunogen protein (e.g., the protein motif of SEQ ID NO: 4). In order to make this comparison, the two proteins are each assayed at a wide range of concentrations and the amount of each protein required to inhibit 50% of the binding of the antisera to the immobilized protein is determined. If the amount of the second protein required is less than twice the amount of the protein of SEQ ID NO: 4 that is required, then the second protein is said to specifically bind to an antibody generated to the immunogen.

It is understood that F06B09 proteins are families of homologous proteins that comprise two or more genes. For a particular gene product, such as the human F06B09 proteins, the term refers not only to the amino acid sequences disclosed herein, but also to other proteins that are polymorphic, allelic, non-allelic, or species variants or equivalents. It is also understood that the term "human F06B09 protein" includes equivalent proteins, e.g., nonnatural mutations introduced by deliberate mutation using conventional recombinant technology such as single site mutation, or by excising short sections of DNA encoding F06B09 proteins, or by substituting new amino acids, or adding new amino acids. Such minor alterations must substantially maintain the immunoidentity of the original molecule and/or its biological activity. Thus, these alterations include proteins that are specifically immunoreactive with a designated naturally occurring F06B09 protein, for example, the human F06B09 protein shown in SEQ ID NO: 4. The biological properties of the altered proteins can be determined by expressing the protein in an appropriate cell line and measuring, e.g., enzymatic activity under appropriate conditions. Particular protein modifications considered minor would include conservative substitution of amino acids with similar chemical properties, as described above for F06B09 protein families as a whole. By aligning a protein optimally with the protein of SEQ ID NO: 4, and by using the conventional immunoassays described herein to determine immunoidentity, or by using lymphocyte chemotaxis assays, one can determine the protein compositions of the invention.

IX. Functional Variants

The blocking of physiological response to F06B09 protein may result from the inhibition of enzymatic activity of the protein against its substrate, e.g., through competitive inhibition. Thus, in vitro assays of the present invention will often use isolated protein, membranes from cells expressing a recombinant membrane associated proteins, soluble fragments comprising enzymatically active segments of these proteins, or fragments attached to solid phase substrates. These assays will also allow for the diagnostic determination of the effects of either binding segment mutations and modifications, or protein mutations and modifications, e.g., protein analogs. This invention also contemplates the use of competitive drug screening assays, e.g., where neutralizing antibodies to antigen or enzyme fragments compete with a test compound for binding to the protein. In this manner, the antibodies can be used to detect the presence of a polypeptide which shares one or more antigenic binding sites of the protein and can also be used to occupy binding sites on the protein that might otherwise interact with, e.g., substrate.

"Derivatives" of F06B09 proteins include amino acid sequence mutants, glycosylation variants, and covalent or aggregate conjugates with other chemical moieties. Covalent derivatives can be prepared by linkage of functionalities to groups which are found in F06B09 protein amino acid side chains or at the N- or C- termini, e.g., by means which are well known in the art. These derivatives can include, without limitation, aliphatic esters or amides of the carboxyl terminus, or of residues containing carboxyl side chains, 0-acyl derivatives of hydroxyl group-containing residues, and N-acyl derivatives of the amino terminal amino acid or amino-group containing residues, e.g., lysine or arginine. Acyl groups are typically selected from the group of alkyl-moieties including, e.g., C3 to C18 normal alkyl, thereby forming alkanoyl aroyl species. Covalent attachment to carrier proteins may be important when immunogenic moieties are haptens.

In particular, glycosylation alterations are included, e.g., made by modifying the glycosylation patterns of a polypeptide during its synthesis and processing, or in further processing steps. Particularly preferred means for accomplishing this are by exposing the polypeptide to glycosylating enzymes derived from cells which normally provide such processing, e.g., mammalian glycosylation enzymes. Deglycosylation enzymes are also contemplated. Also embraced are versions of the same primary amino acid sequence which have other minor modifications, including phosphorylated amino acid residues, e.g., phosphotyrosine, phosphoserine, or phosphothreonine, or other moieties, including ribosyl groups or cross-linking reagents.

A major group of derivatives are covalent conjugates of the F06B09 protein or fragments thereof with other proteins or polypeptides. These derivatives can be synthesized in recombinant culture such as N- or C-terminal fusions or by the use of agents known in the art for their usefulness in cross-linking proteins through reactive side groups. Preferred protein derivatization sites with cross-linking agents are at free amino groups, carbohydrate moieties, and cysteine residues.

Fusion polypeptides between human F06B09 proteins and other homologous or heterologous proteins are also provided. Heterologous polypeptides may be fusions between different related proteins, resulting in, e.g., a hybrid protein exhibiting modified substrate or other binding specificity. Likewise, heterologous fusions may be constructed which would exhibit a combination of properties or activities of the derivative proteins. Typical examples are fusions of a reporter polypeptide, e.g., luciferase, with a segment or domain of a protein, e.g., a receptor-binding segment, so that the presence or location of the fused protein may be easily determined. See, e.g., Dull, et al., U.S. Pat. No. 4,859,609. Other gene fusion partners include bacterial β-galactosidase, trpE, Protein A, β-lactamase, alpha amylase, alcohol dehydrogenase, and yeast alpha mating factor. See, e.g., Godowski, et al. (1988) *Science* 241:812–816.

Such polypeptides may also have amino acid residues which have been chemically modified by phosphorylation, sulfonation, biotinylation, or the addition or removal of other moieties, particularly those which have molecular shapes similar to phosphate groups. In some embodiments, the modifications will be useful labeling reagents, or serve as purification targets, e.g., affinity ligands.

This invention also contemplates the use of derivatives of F06B09 proteins other than variations in amino acid sequence or glycosylation. Such derivatives may involve covalent or aggregative association with chemical moieties. These derivatives generally include the three classes: (1) salts, (2) side chain and terminal residue covalent modifications, and (3) adsorption complexes, for example with cell membranes. Such covalent or aggregative derivatives are useful as immunogens, as reagents in immunoassays, or in purification methods such as for affinity purification of ligands or other binding ligands. For example, an F06B09 protein can be immobilized by covalent bonding to a solid support such as cyanogen bromide-activated SEPHAROSE, by methods which are well known in the art, or adsorbed onto polyolefin surfaces, with or without glutaraldehyde cross-linking, for use in the assay or purification of anti-F06B09 protein antibodies. The F06B09 proteins can also be labeled with a detectable group, e.g., radioiodinated by the chloramine T procedure, covalently bound to rare earth chelates, or conjugated to another fluorescent moiety for use in diagnostic assays. Purification of F06B09 proteins may be effected by immobilized antibodies or substrate.

Isolated F06B09 protein genes will allow transformation of cells lacking expression of corresponding F06B09 proteins, e.g., either species types or cells which lack corresponding proteins and exhibit negative background activity. Expression of transformed genes will allow isolation of antigenically pure cell lines, with defined or single specie variants. This approach will allow for more sensitive detection and discrimination of the physiological effects of F06B09 protein substrate proteins. Subcellular fragments, e.g., cytoplasts or membrane fragments, can be isolated and used.

X. Uses

The present invention provides reagents which will find use in diagnostic applications as described elsewhere herein, e.g., in the general description for metabolic abnormalities, or below in the description of kits for diagnosis.

F06B09 protein nucleotides, e.g., human F06B09 protein DNA or RNA, may be used as a component in a forensic assay. For instance, the nucleotide sequences provided may be labeled using, e.g., $^{32}P$ or biotin and used to probe standard restriction fragment polymorphism blots, providing a measurable character to aid in distinguishing between individuals. Such probes may be used in well-known forensic techniques such as genetic fingerprinting. In addition, nucleotide probes made from F06B09 protein sequences may be used in in situ assays to detect chromosomal abnormalities.

Antibodies and other binding agents directed towards F06B09 proteins or nucleic acids may be used to purify the corresponding F06B09 protein molecule. As described in the Examples below, antibody purification of F06B09 protein components is both possible and practicable. Antibodies and other binding agents may also be used in a diagnostic fashion to determine whether F06B09 protein components are present in a tissue sample or cell population using well-known techniques described herein. The ability to attach a binding agent to an F06B09 protein provides a means to diagnose disorders associated with F06B09 protein misregulation. Antibodies and other F06B09 protein binding agents may also be useful as histological or sorting markers. As described in the examples below, F06B09 protein expression is limited to specific tissue types. By directing a probe, such as an antibody or nucleic acid to an F06B09 protein, it is possible to use the probe to distinguish tissue and cell types in situ or in vitro.

This invention also provides reagents with significant therapeutic value. The F06B09 protein (naturally occurring or recombinant), fragments thereof, and antibodies thereto, along with compounds identified as having binding affinity to an F06B09 protein, are useful in the treatment of conditions associated with abnormal metabolism, physiology, or development, including abnormal immune responsiveness or non-responsiveness. Abnormal proliferation, regeneration, degeneration, and atrophy may be modulated by appropriate therapeutic treatment using the compositions provided herein. The F06B09 proteins likely play roles in regulation or development of hematopoietic cells, e.g., lymphoid cells, which affect immunological responses.

Thus, for example, an antagonist of an F06B09 protein could be useful in blocking the conversion of an immature or inactive immunologically relevant pro-protein to the mature or active form. Since the F06B09 proteases were derived from dendritic cells, antagonists could also be important in preventing antigen processing and/or subsequent presentation. In addition, effects on DC migration or dendrite extension between cells may result. One potential therapeutic application of F06B09 would be to block this protease in inflammatory processes involving the dendritic cells (DC). The blocking could occur on the F06B09 MMP itself or on other molecules interacting with it.

Other abnormal developmental conditions are known in cell types shown to possess F06B09 protein encoding mRNA by northern blot analysis. See Berkow (ed.) *The Merck Manual of Diagnosis and Therapy.* Merck & Co., Rahway, N.J.; and Thorn, et al. *Harrison's Principles of Internal Medicine.* McGraw-Hill, N.Y. Developmental or functional abnormalities, e.g., of the immune system, cause significant medical abnormalities and conditions which may be susceptible to prevention or treatment using compositions provided herein.

Recombinant F06B09 protein antibodies can be purified and then administered to a patient. These reagents can be combined for therapeutic use with additional active or inert ingredients, e.g., in conventional pharmaceutically acceptable carriers or diluents, e.g., immunogenic adjuvants, along with physiologically innocuous stabilizers and excipients. These combinations can be sterile filtered and placed into dosage forms as by lyophilization in dosage vials or storage in stabilized aqueous preparations. This invention also contemplates use of antibodies or binding fragments thereof, including forms which are not complement binding.

Drug screening using antibodies or fragments thereof can identify compounds having binding affinity to F06B09 protein, including isolation of associated components. Various substrate candidates can be screened. Subsequent biological assays can then be utilized to determine if the compound has intrinsic enzyme blocking activity. Likewise, a compound having intrinsic stimulating activity might activate the activity of an F06B09 protein. This invention further contemplates the therapeutic use of antibodies to F06B09 protein as antagonists. This approach should be particularly useful with other F06B09 protein polymorphic or species variants.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds. 1990) *Goodman and Gilman's: The Pharmacological Bases of Therapeutics* (8th ed.) Pergamon Press; and (1990) *Remington's Pharmaceutical Sciences* (17th ed.) Mack Publishing Co., Easton, Pa. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index*, Merck & Co., Rahway, N.J. Dosage ranges would ordinarily be expected to be in amounts lower than 1 mM concentrations, typically less than about 10 $\mu$M concentrations, usually less than about 100 nM, preferably less than about 10 pM (picomolar), and most preferably less than about 1 fM (femtomolar), with an appropriate carrier. Slow release formulations, or a slow release apparatus will often be utilized for continuous administration.

F06B09 proteins, fragments thereof; antibodies to it or its fragments; antagonists; and agonists, may be administered directly to the host to be treated or, depending on the size of the compounds, it may be desirable to conjugate them to carrier proteins such as ovalbumin or serum albumin prior to their administration. Therapeutic formulations may be administered in any conventional dosage formulation. While it is possible for the active ingredient to be administered alone, it is preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. See, e.g., Gilman, et al. (eds. 1990) *Goodman and Gilman's: The Pharmacological Bases of Therapeutics* (8th ed.) Pergamon Press; and (1990) *Remington's Pharmaceutical Sciences* (17th ed.) Mack Publishing Co., Easton, Pa.; Avis, et al. (eds. 1993) *Pharmaceutical Dosage Forms: Parenteral Medications* Dekker, N.Y.; Lieberman, et al. (eds. 1990) *Pharmaceutical Dosage Forms: Tablets* Dekker, N.Y.; and Lieberman, et al. (eds. 1990) *Pharmaceutical Dosage Forms: Disperse Systems* Dekker, N.Y. The therapy of this invention may be combined with or used in association with other therapeutic agents.

Both the naturally occurring and the recombinant forms of the F06B09 proteins of this invention are particularly useful in kits and assay methods which are capable of screening compounds for binding activity to the proteins, including substrates or competitive inhibitors. Several methods of automating assays have been developed in recent years so as to permit screening of tens of thousands of compounds in a short period. See, e.g., Fodor, et al. (1991) *Science* 251:767–773, and other descriptions of chemical diversity libraries, which describe means for testing of binding affinity by a plurality of compounds. The development of suitable assays can be greatly facilitated by the availability of large amounts of purified, soluble F06B09 protein as provided by this invention.

For example, antagonists or inhibitors can normally be found once the protein has been structurally defined. Testing of potential substrates or analogs is now possible upon the development of highly automated assay methods using a purified enzyme. In particular, new agonists and antagonists will be discovered by using screening techniques described herein. Of particular importance are compounds found to have a combined blockage activity for multiple F06B09 protein substrates, e.g., compounds which can serve as antagonists for polymorphic or species variants of an F06B09 protein. Inhibitors can be identified, which may be useful as therapeutic entities.

This invention is particularly useful for screening compounds by using recombinant protein in a variety of drug screening techniques. The advantages of using a recombinant protein in screening for specific inhibitors include: (a) improved renewable source of the F06B09 protein from a specific source; (b) potentially greater number of molecules per cell giving better signal to noise ratio in assays; and (c) species variant specificity (theoretically giving greater biological and disease specificity).

One method of drug screening utilizes eukaryotic or prokaryotic host cells which are stably transformed with recombinant DNA molecules expressing an F06B09 protein substrate. Cells may be isolated which express a substrate in isolation from any others. Such cells, either in viable or fixed form, can be used for standard enzyme/substrate cleavage assays. See also, Parce, et al. (1989) *Science* 246:243–247; and Owicki, et al. (1990) *Proc. Nat'l. Acad. Sci. USA* 87:4007–4011, which describe sensitive methods to detect cellular responses. Competitive assays are particularly useful, where the cells (source of F06B09 protein) or homogenates are contacted and incubated with a labeled antibody having known binding affinity to the protein, such as $^{125}$I-antibody, and a test sample whose binding affinity to the binding composition is being measured. The bound and free labeled binding compositions are then separated to assess the degree of antigen binding. The amount of test compound bound is inversely proportional to the amount of labeled reagent binding to the known source. Any one of numerous techniques can be used to separate bound from free antigen to assess the degree of ligand binding. This separation step could typically involve a procedure such as adhesion to filters followed by washing, adhesion to plastic followed by washing, or centrifugation of the cell membranes. Viable cells could also be used to screen for the effects of drugs on F06B09 protein mediated functions, e.g., proprotein activation, substrate cleavage, and others. Some detection methods allow for elimination of a separation step, e.g., a proximity sensitive detection system.

Another method utilizes solubilized, unpurified or solubilized, purified F06B09 protein from transformed eukaryotic or prokaryotic host cells. This allows for a "molecular" binding assay with the advantages of increased specificity, the ability to automate, and high drug test throughput.

Another technique for drug screening involves an approach which provides high throughput screening for compounds having suitable binding affinity to an F06B09 protein, e.g., an antibody, is described in detail in Geysen, European Patent Application 84/03564, published on Sep. 13, 1984. First, large numbers of different small peptide test compounds are synthesized on a solid substrate, e.g., plastic pins or some other appropriate surface, see Fodor, et al., supra. Then all the pins are reacted with solubilized, unpurified or solubilized, purified F06B09 protein antibody, and washed. The next step involves detecting bound F06B09 protein antibody.

Rational drug design may also be based upon structural studies of the molecular shapes of the F06B09 protein and other effectors or analogs. See, e.g., *Methods in Enzymology* vols. 202 and 203. Effectors may be other proteins which mediate other functions in response to antigen binding, or other proteins which normally interact with the substrate. One means for determining which sites interact with specific other proteins is a physical structure determination, e.g., x-ray crystallography or 2 dimensional NMR techniques. These will provide guidance as to which amino acid residues form molecular contact regions. For a detailed description of protein structural determination, see, e.g., Blundell and Johnson (1976) *Protein Crystallography* Academic Press, NY.

A purified F06B09 protein can be coated directly onto plates for use in the aforementioned drug screening techniques. However, non-neutralizing antibodies to these antigens can be used as capture antibodies to immobilize the respective antigen on the solid phase. Candidates for screening include for hybridomas, to find clones with desired binding specificity, or for inhibitors, e.g., of enzymatic activity.

XI. Kits

This invention also contemplates use of F06B09 proteins, fragments thereof, peptides, and their fusion products in a variety of diagnostic kits and methods for detecting the presence of F06B09 protein or an F06B09 protein substrate. Typically the kit will have a compartment containing either a defined F06B09 peptide or gene segment or a reagent which recognizes one or the other, e.g., substrates or antibodies.

A kit for determining the-binding affinity of a test compound to an F06B09 protein would typically comprise a test compound; a labeled compound, e.g., an antibody having known binding affinity for the F06B09 protein; a source of F06B09 protein (naturally occurring or recombinant); and a means for separating bound from free labeled compound, such as a solid phase for immobilizing the F06B09 protein. Once compounds are screened, those having suitable binding affinity to the F06B09 protein can be evaluated in suitable biological assays, as are well known in the art, to determine whether they act as agonists or antagonists to a substrate. The availability of recombinant F06B09 polypeptides also provide well defined standards for calibrating such assays.

A preferred kit for determining the concentration of, for example, an F06B09 protein in a sample would typically comprise a labeled compound, e.g., antibody, having known binding affinity for the F06B09 protein, a source of F06B09 protein (naturally occurring or recombinant), and a means for separating the bound from free labeled compound, for example, a solid phase for immobilizing the F06B09 protein. Compartments containing reagents, and instructions, will normally be provided.

Antibodies, including antigen binding fragments, specific for the F06B09 protein, or fragments thereof, are useful in diagnostic applications to detect the presence of elevated levels of F06B09 protein and/or its fragments. Such diagnostic assays can employ lysates, live cells, fixed cells, immunofluorescence, cell cultures, body fluids, and further can involve the detection of antigens related to the ligand in serum, or the like. Diagnostic assays may be homogeneous (without a separation step between free reagent and F06B09 protein complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA), and the like. For example, unlabeled antibodies can be employed by using a second antibody which is labeled and which recognizes the antibody to an F06B09 protein or to a particular fragment thereof. Similar assays have also been extensively discussed in the literature. See, e.g., Harlow and Lane (1988) *Antibodies; A Laboratory Manual,* CSH Press, NY; Chan (ed. 1987) *Immunoassay: A Practical Guide* Academic Press, Orlando, Fla.; Price and Newman (eds. 1991) *Principles and Practice of Immunoassay* Stockton Press, NY; and Ngo (ed. 1988) *Nonisotopic Immunoassay* Plenum Press, NY.

Anti-idiotypic antibodies may have similar use to diagnose presence of antibodies against an F06B09 protein, as such may be diagnostic of various abnormal states. For example, overproduction of F06B09 protein may result in production of various immunological or other medical reactions which may be diagnostic of abnormal physiological states, e.g., in cell growth, activation, or differentiation.

Frequently, the reagents for diagnostic assays are supplied in kits, so as to optimize the sensitivity of the assay. For the subject invention, depending upon the nature of the assay, the protocol, and the label, either labeled or unlabeled antibody, or labeled F06B09 protein is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium providing appropriate concentrations of reagents for performing the assay.

Many of the aforementioned constituents of the drug screening and the diagnostic assays may be used without modification, or may be modified in a variety of ways. For example, labeling may be achieved by covalently or non-covalently joining a moiety which directly or indirectly provides a detectable signal. In any of these assays, the protein, test compound, F06B09 protein, or antibodies thereto can be labeled either directly or indirectly. Possibilities for direct labeling include label groups: radiolabels such as $^{125}$I, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups.

There are also numerous methods of separating the bound from the free antigen, or alternatively the bound from the free test compound. The F06B09 protein can be immobilized on various matrices followed by washing. Suitable matrices include plastic such as an ELISA plate, filters, and beads. Methods of immobilizing the F06B09 protein to a matrix include, without limitation, direct adhesion to plastic, use of a capture antibody, chemical coupling, and biotin-avidin. The last step in this approach usually involves the precipitation of enzyme/antibody or enzyme substrate complex by various methods including those utilizing, e.g., an organic solvent such as polyethylene glycol or a salt such as ammonium sulfate. Other suitable separation techniques include, without limitation, the fluorescein antibody magnetizable particle method described in Rattle, et al. (1984) Clin. Chem. 30:1457–1461, and the double antibody magnetic particle separation as described in U.S. Pat. No. 4,659,678.

Methods for linking proteins or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequence of an F06B09 protein. These sequences can be used as probes for detecting levels of the F06B09 protein message in samples from natural sources, or patients suspected of having an abnormal condition, e.g., immune problem. The preparation of both RNA and DNA nucleotide sequences, the labeling of the sequences, and the preferred size of the sequences has received ample description and discussion in the literature. Normally an oligonucleotide probe should have at least about 14 nucleotides, usually at least about 18 nucleotides, and the polynucleotide probes may be up to several kilobases. Various detectable labels may be employed, most commonly radionuclides, particularly $^{32}$P. However, other techniques may also be employed, such as using biotin modified nucleotides for introduction into a polynucleotide. The biotin then serves as the site for binding to avidin or antibodies, which may be labeled with a wide variety of labels, such as radionuclides, fluorophores, enzymes, or the like. Alternatively, antibodies may be employed which can recognize specific duplexes, including DNA duplexes, RNA duplexes, DNA-RNA hybrid duplexes, or DNA-protein duplexes. The antibodies in turn may be labeled and the assay carried out where the duplex is bound to a surface, so that upon the formation of duplex on the surface, the presence of antibody bound to the duplex can be detected. The use of probes to the novel anti-sense RNA may be carried out using many conventional techniques such as nucleic acid hybridization, plus and minus screening, recombinational probing, hybrid released translation (HRT), and hybrid arrested translation (HART). This also includes amplification techniques such as polymerase chain reaction (PCR).

Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet, et al. (1989) *Progress in Growth Factor Res.* 1:89–97.

XII. Substrate Identification

Having isolated a protease, methods exist for identifying a target substrate. For example, a candidate substrate can be contacted with an F06B09 protein in an enzymatic reaction. The resulting cleavage or product can be analyzed, e.g., using SDS-PAGE, HPLC, spectroscopy or other forms of analysis. For example, the molecular weight of a protease cleavage product should be compared against the molecular weights of the uncleaved substrate and the F06B09 protein. The successful candidate substrate will exhibit a shift to a lower molecular weight. Analysis of the substrate should determine what site specificity may exist for the enzyme under the tested conditions. Alternatively, if the protease acts by transforming an inactive substrate to the active form, the resulting activity can be assayed, e.g., by the result of the activated factor, e.g., proliferation, apoptosis, or activation of a target cell.

Sequence specificity of products may allow search through sequence databases to identify candidate proteins as physiologically natural substrates. Alternatively, the protease may be involve in antigen processing and presentation to appropriate immune cells.

The broad scope of this invention is best understood with reference to the following examples, which are not intended to limit the invention to specific embodiments.

EXAMPLES

I. General Methods

Many of the standard methods below are described or referenced, e.g., in Maniatis, et al. (1982) *Molecular Cloning. A Laboratory Manual* Cold Spring Harbor Laboratory, Cold Spring Harbor Press, NY; Sambrook, et al. (1989) *Molecular Cloning: A Laboratory Manual* (2d ed.) Vols. 1–3, CSH Press, NY; Ausubel, et al., *Biology* Greene Publishing Associates, Brooklyn, N.Y.; or Ausubel, et al. (1987 and Supplements) *Current Protocols in Molecular Biology* Wiley/Greene, NY; Innis, et al. (eds. 1990) *PCR Protocols: A Guide to Methods and Applications* Academic Press, NY. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification," *Methods in Enzymology* vol. 182, and other volumes in this series; and manufacturer's literature on use of protein purification products, e.g., Pharmacia, Piscataway, N.J., or Bio-Rad, Richmond, Calif. Combination with recombinant techniques allow fusion to appropriate segments (epitope tags), e.g., to a FLAG sequence or an equivalent which can be fused, e.g., via a protein-removable sequence. See, e.g., Hochuli (1989) *Chemische Industrie* 12:69–70; Hochuli (1990) "Purification of Recombinant Proteins with Metal Chelate Absorbent" in Setlow (ed.) *Genetic Engineering, Principle and Methods* 12:87–98, Plenum Press, NY; and Crowe, et al. (1992) *OIAexpress: The High Level Expression & Protein Purification System* QUIAGEN, Inc., Chatsworth, Calif.

Standard immunological techniques are described, e.g., in Hertzenberg, et al. (eds. 1996) *Weir's Handbook of Experimental Immunology* vols. 1–4, Blackwell Science; Coligan (1991) *Current Protocols in Immunology* Wiley/Greene, NY; and *Methods in Enzymology* volumes. 70, 73, 74, 84, 92, 93, 108, 116, 121, 132, 150, 162, and 163. Assays for neural cell biological activities are described, e.g., in Wouterlood (ed. 1995) *Neuroscience Protocols* modules 10, Elsevier; *Methods in Neurosciences* Academic Press; and *Neuromethods* Humana Press, Totowa, N.J. Methodology of developmental systems is described, e.g., in Meisami (ed.) *Handbook of Human Growth and Developmental Biology* CRC Press; and Chrispeels (ed.) *Molecular Techniques and Approaches in Developmental Biology* Interscience.

FACS analyses are described in Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y.

II. Hematopoietic Factors, Cells, and Cell Lines rhGM-CSF (specific activity : $2 \times 10^6$ U/mg; Schering-Plough Research Institute, Kenilworth, N.J.) was used at a saturating concentration of 100 ng/ml (200 U/ml). rhTNFα (specific activity : $2 \times 10^7$ U/mg; Genzyme, Boston, Mass.) was used at an optimal concentration of 2.5 ng/ml (50 U/ml). rhSCF (specific activity : $4 \times 10^5$ U/mg; R&D, Abington, U.K.) and rhM-CSF (specific activity : $2 \times 10^6$ U/mg; R&D) were used at optimal concentration of 25 ng/ml. rhG-CSF ($ED_{50}$: 0.01–0.03 ng/ml R&D) was used at an optimal concentration of 25 ng/ml.

Peripheral blood mononuclear cells (PBMC) were obtained from healthy donors after Ficoll-Hypaque gradient centrifugation (d=1.077; Eurobio, Paris, France). T cells were purified from PBMC by immunomagnetic depletion (Dynal, Oslo, Norway) using a cocktail of mAbs (CD14, CD16, CD35, HLA-DR, (Immunotech, Marseille, France), CD19 (ascites), NKH1 (Coulter, Hialeah, Fla.), CD40 (mAb 89 produced in the laboratory)). The purity of $CD3^+$ T cells was higher than 95%. T cells were activated with coated anti-CD3 and soluble anti-CD28 mAbs for 3, 12 and 24 h. B cells were obtained from human tonsils as described (Liu, et al. (1996) *Immunity.* 4:603–613). Briefly, T cells were first depleted by rosetting sheep red blood cells and then the residual non-B cells were removed by immunomagnetic depletion using a cocktail of mAbs (CD2, CD3, CD4, CD14, CD16, NKH1, CD35). The purity of $CD19^+$ B cells was higher than 98%. Langerhans cells were prepared from normal skin by CD1a positive selection as described (Le Varlet, et al. (1992) *J. Leukoc. Biol.* 51:415–420). Granulogytes were generated in vitro from $CD34^+$ progenitors in the presence of G-CSF and SCF for 12 days. Macrophages were generated in vitro by culturing human cord blood $CD34^+$ progenitors with M-CSF and SCF for 12 days (Szabolcs, et al. (1996) *Blood.* 87:4520–4530). Cells were unactivated or activated by PMA-ionomycin for 1 and 6 h (PMA: 1 ng/ml, Sigma, St. Louis, Mo.; Ionomycin: 1 µg/ml, Calbiochem, La Jolla, Calif.) and pooled. The TF1 (erythrocytic), Jurkat (T cell), MRC5 (fibroblastic), JY (lymphoblastoid B cell), and U937 (myelomonocytic) cell lines were obtained from American Type Culture Collection (ATCC, Rockville, Md.). CHA is an epithelial kidney carcinoma cell line kindly provided by C. Bain (Centre Léon Bérard, Lyon, France). All cell lines were stimulated by PMA-ionomycin for 1 h and 6 h and pooled. Murine fibroblasts transfected with human CD40 ligand (CD40L L cells) were produced in the laboratory (Garrone, et al. (1995) *J. Exp. Med.* 182:1265–1273. All cell types were cultured in RPMI 1640 (GIBCO BRL, Gaithersburg, Md.) supplemented with 10% (vol/vol) heat-inactivated fetal bovine serum (FBS; Flow laboratories, Irvine, UK), 10 mM Hepes, 2 mM L-glutamine, $5 \times 10^{-5}$ M 2-mercaptoethanol, penicillin (100 U/ml) and streptomycin (100 µg/ml; hereafter referred to as complete medium). Generation of DC from $CD34^+$ cells and from monocytes.

Umbilical cord blood samples were obtained according to appropriate institutional guidelines. Isolation of $CD34^+$ progenitors was achieved using Minimacs separation columns (Miltenyi Biotec GmbH) as described by Caux, et al. (1996) *J. Exp. Med.* 184:695–706. In all experiments, the isolated cells were 80 to 99% $CD34^+$ as judged by staining with anti-CD34 mAb. Cultures of $CD34^+$ cells were established in the presence of SCF, GM-CSF, and TNFα as described by Caux, et al. (1992) *Nature* 360:258–261; or Caux, et al. (1996) *J. Exp. Med.* 184:695–706. Cells collected after 6 days of culture were separated according to CD1a and CD14 expression into $CD14^+CD1a^-$ and $CD14-CD1a^+$ using a $FACStar^+$ (Becton Dickinson, Mountain View, Calif.) as described (Caux, et al. (1996) *J. Exp. Med.* 184:695–706). Cells were further cultured in presence of GM-CSF and TNFα until day 12–17, when 70–90% of cells are $CD1a^+$ DC. Monocytes were purified by immunomagnetic depletion (Dynal) after preparation of PBMC followed by a 52% Percoll gradient. The depletion was performed with anti-CD3, anti-CD19, and anti-CD8 ascites, and with purified anti-NKH1 (Coulter) and anti-CD16 (Immunotech) mAbs. Monocyte-derived dendritic cells were produced by culturing purified monocytes for 6 days in the presence of GM-CSF and IL-4 (Sallusto and Lanzavecchia (1994) *J. Exp. Med.* 179:1109–1118). Cells were activated with LPS at the concentration of 25 ng/ml for 1 h to 72 h or with CD40L transfected L cells (one L cell for five DC) (Caux, et al. (1994) *J. Exp. Med.* 180:1263–1272).

III. cDNA Libraries and Isolation of F06B09 cDNA Clone

Total RNA was isolated from PMA-ionomycin activated $CD1a^-CD14^+$ DC (at day 12 of the culture) and from activated CHA cell line. See Chomczynski and Sacchi (1987) *Anal. Biochem.* 162:156–159. RNA was treated with DNase I before mRNA purification using the Oligotex-dT kit (Qiagen GmbH, Hilden, Germany). PolyA+ RNA (2 µg) was used to make a cDNA library in the pSport vector (Superscript Plasmid System Kit, GIBCO BRL). A subtraction library was made using the method of Hara et al. (1994) *Blood* 84:189–199, with minor modifications. In this protocol, tracer (subtracted) cDNA was the $CD14^+$-derived DC cDNA, and driver (subtractive) cDNA was CHA cDNA. A 0.6 Kb cDNA containing a polyA tail was isolated from the $CD14^+$-derived DC subtraction library. The cDNA of this gene was first amplified using the RACE MARATHON™ kit (Clontech, Palo Alto, Calif.) and two oligonucleotides: 5'CAGAAATGCCACGAAACAGCCAGG-TACT (NGSP1; SEQ ID NO: 5) and 5'GCCCCAGTTGCTCATACAAACAGATCAG (GSP1; SEQ ID NO: 6) with a recommended cycling program 1. PCR products were cloned in the pCRII plasmid (Invitrogen, San Diego, Calif.). A lambda $CD34^+$-derived DC cDNA library was constructed using the GREAT LENGTHS™ cDNA Synthesis kit with the λTriplEx vector (Clontech), and was next screened with a 5' F06B09 probe to obtain a full-length cDNA. Sequencing was performed on both strands by the dideoxynucleotide method using a Taq Dye Deoxy Terminator Cycle Sequencing kit (Applied Biosystems, Foster City, Calif.) and an automated sequencer (Applied Biosystems).

A clone encoding the human F06B09 protein is isolated from a natural human dendritic cell or other source, by one of many different possible methods. Given the sequences provided herein, PCR primers or hybridization probes are selected and/or constructed to isolate a nucleic acid, e.g., genomic DNA segments or cDNA reverse transcripts. Appropriate cell sources include human tissues, e.g., dendritic cell libraries. Tissue distribution below also suggests source tissues. Genetic and polymorphic or allelic variants are isolated by screening a population of individuals.

This clone was discovered via EST analysis of human dendritic cell subtraction cDNA library. The driver was CD34+ derived, CD14+, PMA, and ionomycin activated dendritic cell cDNA, while subtractor was PMA and ionomycin activated, kidney carcinoma cell line CHA. The initial poly-A containing EST was selected for its restricted distribution after Northern blot and semi-quantitative PCR analysis. A novel 0.6 Kb partial cDNA (F06B09) was isolated by screening a PMA-ionomycin activated CD34+-derived DC subtraction library. Northern blots probed with the F06B09 clone showed a 3.7 Kb mRNA transcript predominantly expressed in dendritic cells. This mRNA was absent by RT-PCR in CHA, the driver epithelial cell line used for subtraction. The 5' end of the original sequence was extended by RACE and by the screening of a lambda DC cDNA library, to a final 3691 bp cDNA. This cDNA contains a methionine codon located in a consensus Kozak sequence. See Kozak (1986) *Cell*. 44:283–292. The full-length cDNA (see Table 1) shows a 342 bp 5' untranslated sequence (nt 1–342), a 1689 bp open reading frame (nt 343–2031), a 3' untranslated sequence of 1660 bp (nt 2032–3691) and a polyadenylation signal AATAAA at position 3638–3643 followed by a poly(A)tail. The encoded protein of 562 amino acids reveals a strong homology with membrane-type matrix metalloproteinase (MT-MMP). As a member of the metalloproteinase family, F06B09 contains a propeptide domain with a cysteine-switch activation domain at Cys69 (Van Wart and Birkedal-Hansen (1990) *Proc. Natl. Acad. Sci. USA*. 87:5578–5582) and the core enzyme domain contains three zinc-chelating histidine (H) residues at positions 212, 216 and 222 in the zinc binding motif. Like other MT-MMP members, F06B09 presents a consensus insertion RRRR between residues 82–86, corresponding to a furin cleavage site (Table 1). The sequence is followed by a hinge region (260–290) and a potential transmembrane domain of 12 amino acids (526–577) in a hemopexin-like domain (291–538) and a short intracytoplasmic domain (538–541). Multiple alignment with members of the membrane-type matrix metalloproteinase (MT-MMP) family revealed the closest homology with the MT4-MMP (48%) (Puente, et al. (1996) *Cancer Res*. 56:944–949), and 38%, 39% and 35% respectively with the MT1-MMP (Sato, et al. (1994) *Nature* 370:61–65) the MT2-MMP (Will and Hinzmann (1995) *Eur. J. Biochem*. 231:602–608) and the MT3-MMP (Takino, et al. (1995) *J. Biol. Chem*. 270:23013–23020). Comparison of the most conserved domain, the catalytic domain, showed that F06B09 presents the highest homology to MT4-MMP (48%) (Puente, et al. (1996) *Cancer Res*. 56:944–949) and significant homologies to other members of the matrix membrane metalloproteinase family (MMP), like the type IV collagenases MMP-9 and MMP-2 (Collier, et al. (1988) *J. Biol. Chem*. 263:6579–6587; Wilhelm, et al. (1989) *J. Biol. Chem*. 264:17213–17221).

Therefore, it is suggested that the F06B09 is a fifth member of the MT-MMP subgroup of the MMP.

The coding sequence appears to be complete, encoding a 21 amino acid putative signal peptide followed by a 541 residue polypeptide with significant homology to the membrane-type matrix metalloproteases MT-MMP1 to 4. No evidence yet suggests alternative splicing of this message The limited EST distribution is indicative of a restricted expression pattern.

Further clones will be isolated, e.g., using an antibody based selection procedure. Standard expression cloning methods are applied including, e.g., FACS staining of membrane associated expression product. The antibodies are used to identify clones producing a recognized protein. Alternatively, antibodies are used to purify an F06B09 protein, with protein sequencing and standard means to isolate a gene encoding that protein.

Genomic or cDNA sequence based methods will also allow for identification of sequences naturally available, or otherwise, which exhibit homology to the provided sequences.

IV. Isolation of Mouse F06B09

Similar methods are used as above to isolate an appropriate F06B09 protein gene. See, e.g., GenBank Accession numbers X91785, X83537, D63579, and U54984. Similar source materials as indicated above are used to isolate natural genes, including genetic, polymorphic, allelic, or strain variants. Species variants are also isolated using similar methods. Various sequence databases may suggest related or counterpart sequences. See, e.g., Capone, et al. (1996) *J. Immunol*. 157:969–973.

V. Isolation of an Avian F06B09 Protein Clone

An appropriate avian source is selected as above. Similar methods are utilized to isolate other species variants, though the level of similarity will typically be lower for avian F06B09 protein as compared to a human to mouse sequence.

VI. Message Distribution

PCR based detection is performed by standard methods, preferably using appropriate primers from opposite ends of the coding sequence, but flanking segments might be selected for specific purposes.

Alternatively, hybridization probes are selected. Particular AT or GC contents of probes are selected depending upon the expected homology and mismatching expected. Appropriate stringency conditions are selected to balance an appropriate positive signal to background ratio. Successive washing steps are used to identify clones of greater homology.

Total RNA (20 μg), extracted from cell lines or cell preparations as described above, were fractionated by electrophoresis on a 1% agarose-formaldehyde gel and transferred onto positively charged nylon membrane (GeneScreenPlus, NEN Life Science Products, Boston, Mass.) as described by Thomas (1980) *Proc. Natl. Acad. Sci. USA*. 77:5201–5205. After transfer, blots were cross-linked by UV light (Stratalinker, La Jolla, Calif.). The original cloned 600 bp fragment was labeled by random priming with $^{32}$P-dCTP (3000 Ci/mmol, Amersham; Ready to Go, Pharmacia Biotech, Orsay, France) and unincorporated nucleotides were removed by spin column chromatography (Chromaspin-100, Clontech). Hybridization and washes were performed in stringent conditions (0.1×SSC/0.1% SDS at 65° C.). X-ray films (Kodak, Rochester, N.Y.) were exposed for 3 weeks at −80° C. with intensifying screens. Multiple tissue normal fetal and adult organs Northern blots (purchased from Clontech) were similarly used according to the manufacturer's recommendations.

For RT-PCR methods, sotal RNA extracted from 1 to 10×10$^6$ cells (Chomczynski and Sacchi (1987) *Anal. Biochem*. 162:156–159) were reverse transcribed using random hexamer primers (Pharmacia, Upsalla, Sweden) and the Superscript RNase-H reverse transcriptase (GIBCO BRL). PCR was performed in a 100 μl volume using 5 ng cDNA, 10 μl 10×PCR reaction buffer (Perkin Elmer Cetus, Norwalk, Conn.), 2.5 U of Taq polymerase (Gene Amp PCR reagents kit: Perkin Elmer Cetus) and 200 mM dNTPs and 500 nM of the 5' and 3' amplification primers. The PCR reactions were made in a DNA thermal cycler (Perkin Elmer) for 35 cycles (1 min denaturation at 94° C., 1 min annealing at 60° C., and 2 min elongation at 72° C.). β actin RT-PCR was used as positive control for the efficiency of the reaction using sense and antisense primers. Appropriate sense and antisense primers were used to amplify F06B09. See Table 1.

Northern blot showed a single band of about 4.5 kb in non-activated and PMA and ionomycin-activated, CD34+ derived human DC, and a weak signal in in vitro generated granulogytes. No signal was detected in TF1, Jurkat, CHA, or JY cell lines, nor in freshly isolated monocytes, activated T cells, resting and activated PBLs, or B cells. No expression was found in either fetal or adult tissues. PCR distribution analysis showed expression in activated DC and the MRC5 lung fibroblast cell line, as well as very low signal in U937. The original EST was extended by 5' RACE. A lambda DC cDNA library was screened with a 5' probe. An ORF was identified, which showed highest homology with the human MT4-MMP, a recent addition to the membrane type matrix metalloprotease family. Positive signals were also detected in granulogytes.

Northern blot analysis showed a single ~4 Kb transcript predominantly expressed in resting CD34+-derived DC, to a lesser extent in PMA-ionomycin activated DC, and weakly in granulogytes generated in vitro. The expression pattern of this novel gene was also analyzed by RT-PCR, on freshly isolated cells and on various cell lines. Similarly, RT-PCR analysis confirmed the higher level of F06B09 expression in resting and activated CD34+-derived DC, in granulogytes and to a weaker extent in resting PBLs. F06B09 mRNA is also weakly present on the B cell line, JY. No messenger was detected in TF1 (myelo-erythrocytic), CHA (carcinoma), Jurkat (T cell), MRC5 (fibroblastic) or U937 (myelo-monocytic) cell lines, nor in freshly isolated monocytes, activated T and B cells or activated PBLs. Among normal human tissues tested, a significant band of ~4 Kb was seen in spleen, lymph node, thymus, appendix, PBL and in bone marrow but absent in fetal tissues. An additional 6 Kb band corresponding probably to unspecific expression or to a longer existing form, was also detected in spleen, PBL and bone marrow but absent in lymph node, thymus, and appendix.

The cellular distribution of F06B09 was next determined by the extent of hybridization among the gel-fractionated population of cDNA inserts from libraries made from different cell types. Consistent with the above observations, F06B09 is present in both CD34+-derived DC and in monocyte-derived DC, but also in effector T cells, including Th1 and Th2 cells, and to a weaker extent in NK cells. F06B09 mRNA expression is down-regulated after PMA-ionomycin activation at once in DC and T cells. No signal was detected in monocytes, B cell lines nor in different fetal tissues.

In conclusion, the novel MT-MMP appears to be mainly transcribed by resting DC and weakly by effector T cells.

F06B09 mRNA is strongly expressed in different types of DC and down-regulated by CD40L activation. Since the original F06B09 clone was identified in a DC library, further characterization was performed by semi-quantitative RT-PCR. The expression of this gene was analyzed during DC differentiation and maturation, either in DC generated in vitro from CD34+ cord blood progenitors cultured with GM-CSF and TNFα or from monocytes cultured with GM-CSF and IL-4. During the culture of CD34+ human cord blood progenitors, F06B09 is first detected at day 6 and increases up to day 12. This messenger is down-regulated after triggering final maturation of the DC by 4 days co-culture with CD40L-transfected L cells. Similarly, while monocytes do not express detectable amount of F06B09 mRNA, a significant expression could be detected after 6 days of culture in the presence of GM-CSF and IL-4. In contrast, following activation of these monocyte-derived DC through CD40, the level of mRNA decreases rapidly within 3 h to 12 h. A low amount of F06B09 mRNA is also found in 1 h PMA-ionomycin activated CD1a+ and CD14+ DC subsets, which is down-regulated after 6h PMA-ionomycin activation. Day 12 macrophages generated in vitro express also weakly F06B09, and 6 h PMA-ionomycin activation of these cells is enough to switch off the signal. In contrast, no signal is detected in freshly isolated Langerhans cells, in basal keratinocytes, in freshly isolated and CD40L activated B cells, and in anti-CD3 and anti-CD28 activated T cells.

Taken together, these results confirm that F06B09 mRNA is expressed in different DC subtypes and rapidly down-regulated upon DC maturation.

VII. Chromosomal Localization.

The full-length cDNA sequence of F06B09 was analyzed against the EMBL nucleotide and EST databases and resulted in identification of a 436 bp EST (W72721), matching exactly with the F06B09 sequence.

Comparison of the full-length cDNA sequence of F06B09 with the EMBL nucleotide and EST databases identifies a 436 bp EST (W72721), corresponding exactly to the F06B09 sequence. This EST is located on chromosome 16p13.3. In contrast, MT1-MMP and MT3-MMP have been previously located on chromosome 14q11–12 and 8q21.3–22.1 respectively (Mattei, et al. (1997) *Genomics.* 40:168–169.; Mignon, et al. (1995) *Genomics.* 28:360–361). Of note, the novel F06B09 MT-MMP gene is on the same chromosome than MT2-MMP, but both genes are located on a different loci; MT2-MMP is on chromosome 16q12 (Mattei, et al. (1997) *Genomics.* 40:168–169; Yasumitsu, et al. (1997) *DNA Res.* 4:77–79) whereas the novel MT-MMP is on chromosome 16p13.3.

VIII. Expression; Purification; Characterization

With an appropriate clone from above, the coding sequence is inserted into an appropriate expression vector. This may be in a vector specifically selected for a prokaryote, yeast, insect, or higher vertebrate, e.g., mammalian expression system. Standard methods are applied to produce the gene product, preferably as a soluble secreted molecule, but will, in certain instances, also be made as an intracellular protein. Intracellular proteins typically require cell lysis to recover the protein, and insoluble inclusion bodies are a common starting material for further purification.

With a clone encoding a vertebrate F06B09 protein, recombinant production means are used, although natural forms may be purified from appropriate sources, e.g., expressing cell lines. The protein product is purified by standard methods of protein purification, in certain cases, e.g., coupled with imuunoaffinity methods. Immunoaffinity methods are used either as a purification step, as described above, or as a detection assay to determine the partition properties of the protein.

Preferably, the protein is secreted into the medium, and the soluble product is purified from the medium in a soluble form. Standard purification techniques applied to soluble proteins are then applied, with enzyme assays or immuno-detection methods useful for following where the protease purifies. Alternatively, as described above, inclusion bodies from prokaryotic expression systems are a useful source of material. Typically, the insoluble protein is solubilized from the inclusion bodies and refolded using standard methods. Purification methods are developed as described above.

In certain embodiments, the protein is made in a eukaryotic cell which glycosylates the protein normally. The purification methods may be affected thereby, as may biological activities. The intact protein can be processed to release the protein domain, probably due to a cleavage event. While recombinant protein appears to be processed, the physiological processes which normally do such in native cells remain to be determined.

The product of the purification method described above is characterized to determine many structural features. Standard physical methods are applied, e.g., amino acid analysis and protein sequencing. The resulting protein is subjected to CD spectroscopy and other spectroscopic methods, e.g., NMR, ESR, mass spectroscopy, etc. The product is characterized to determine its molecular form and size, e.g., using gel chromatography and similar techniques. Understanding of the chromatographic properties will lead to more gentle or efficient purification methods.

Prediction of glycosylation sites may be made, e.g., as reported in Hansen, et al. (1995) *Biochem. J.* 308:801–813.

IX. Preparation of Antibodies Against Vertebrate F06B09 Protein

With protein produced and purified, as above, animals are immunized to produce antibodies. Polyclonal antiserum may be raised using non-purified antigen, though the resulting serum will exhibit higher background levels. Preferably, the antigen is purified using standard protein purification techniques, including, e.g., affinity chromatography using polyclonal serum indicated above. Presence of specific antibodies is detected using defined synthetic peptide fragments.

Alternatively, polyclonal serum is raised against a purified antigen, purified as indicated above, or using synthetic peptides. A series of overlapping synthetic peptides which encompass all of the full length sequence, if presented to an animal, will produce serum recognizing most linear epitopes on the protein. Such an antiserum is used to affinity purify protein. This purified protein, in turn, may be used to immunize another animal to produce another antiserum preparation.

Standard techniques are used to generate induce monoclonal antibodies to either unpurified antigen, or, preferably, purified antigen.

X. Structure Activity Relationship

Information on the criticality of particular residues is determined using standard procedures and analysis. Standard mutagenesis analysis is performed, e.g., by generating many different variants at determined positions, e.g., at the positions identified above, and evaluating biological activities of the variants. This may be performed to the extent of determining positions which modify activity, or to focus on specific positions to determine the residues which can be substituted to either retain, block, or modulate biological activity.

Alternatively, analysis of natural variants can indicate what positions tolerate natural mutations. This may result from populational analysis of variation among individuals, or across strains or species. Samples from selected individuals are analyzed, e.g., by PCR analysis and sequencing. This allows evaluation of population polymorphisms.

All references cited herein are incorporated herein by reference to the same extent as if each individual publication or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A substantially pure or isolated polypeptide comprising:
    (a) an amino acid sequence which is at least 65% identical to the mature sequence of SEQ ID NO: 2 or
    (b) an amino acid sequence which is at least 65% identical to the mature sequence of SEQ ID NO: 4;
wherein said polypeptide has proteolytic activity.

2. The polypeptide of claim 1, comprising an amino acid sequence which is at least 65% identical to the mature sequence of SEQ ID NO:2.

3. The polypeptide of claim 2, comprising an amino acid sequence which is at least 80% identical to the mature sequence of SEQ ID NO:2.

4. The polypeptide of claim 3, comprising an amino acid sequence which is at least 95% identical to the mature sequence of SEQ ID NO:2.

5. The polypeptide of claim 1, comprising an amino acid sequence which is at least 65% identical to the mature sequence of SEQ ID NO:4.

6. The polypeptide of claim 5, comprising an amino acid sequence which is at least 80% identical to the mature sequence of SEQ ID NO:4.

7. The polypeptide of claim 6, comprising an amino acid sequence which is at least 95% identical to the mature sequence of SEQ ID NO:4.

8. A polypeptide, comprising an amino acid sequence that is identical to the mature sequence of SEQ ID NO: 2.

9. The polypeptide of claim 1, further comprising:
    (a) a detection or purification tag selected from the group consisting of FLAG, His6, and Ig; or
    (b) sequence of a heterologous protein.

10. A polypeptide, comprising an amino acid sequence that is identical to the mature sequence of SEQ ID NO: 4.

11. The polypeptide of claim 1 that is a synthetic polypeptide.

12. A sterile composition comprising:
    (a) the polypeptide of claim 1 that is sterile; or
    (b) said polypeptide of claim 1 and a suitable pharmaceutical carrier, wherein said carrier is formulated for oral, rectal, nasal, topical, or parenteral administration.

13. A kit comprising a polypeptide of claim 1, and:
    (a) a compartment comprising said polypeptide; and/or
    (b) instructions for use or disposal of reagent in said kit.

* * * * *

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 3695 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 344..2032

(ix) FEATURE:
      (A) NAME/KEY: mat_peptide
      (B) LOCATION: 398..2032

(ix) FEATURE:
      (A) NAME/KEY: misc_feature
      (B) LOCATION: 3458
      (D) OTHER INFORMATION: /note= "nucleotide 3458 designated
          W, may be A or T"

(xi) SEQUENCE DESCRIPTION: SEQ ID NO:1:

```
CATGCAACAT AATCTTGCTC GATTCTAAAG TCAACGGATC CTGCAAAATT CGCGGCCGCG      60

TCAACCCATT AGGTCTTGGC CTTGGAATAA AATTGCTTCT CGTCTGATTC CCGGGCCCAC     120

CCGACCCAGC GGCGCAACCC TGGCCCTCCG GGACCCTCCG CTGACTCCAC CGCGCACTTC     180

CCGGGACCCC CACACACATC CCAGCCCTCC GGCCGATCCC TCCCTACTCG GTGCCGGGTG     240

CCCCCCTTTT TTTTCTAGGC CCGGATCTCC TCCCCCAGGT CCCCGGGGCG GCCCCAACCA     300

GGCCCCCTTC AAACCCCGCC GGCGGCCCGG GCTGGGGCGC ACC ATG CGG CTG CGG       355
                                              Met Arg Leu Arg
                                              -18          -15

CTC CGG CTT CTG GCG CTG CTG CTT CTG CAT GCT GGC ACC GCC CGC GCG      403
Leu Arg Leu Leu Ala Leu Leu Leu Leu His Ala Gly Thr Ala Arg Ala
             -10                  -5                        1

CGC CCC GAA GCC CTC GGC GCA GGA CTT AGC CTG GGC TGT GAG AAC TGG      451
Arg Pro Glu Ala Leu Gly Ala Gly Leu Ser Leu Gly Cys Glu Asn Trp
         5                  10                  15

CTG ACT CGC TAT GGT TAC CTA CCG CCA CCC GAC CCT GCC CAG GCC CAG      499
Leu Thr Arg Tyr Gly Tyr Leu Pro Pro Pro Asp Pro Ala Gln Ala Gln
     20                  25                  30

CTG CAG AGC CCT GAA AAT TTG CGC GAT GCC ATC AAA GTC ATG CAA AGG      547
Leu Gln Ser Pro Glu Asn Leu Arg Asp Ala Ile Lys Val Met Gln Arg
35                  40                  45                  50

TTC GCG GGG CTG CCG GAG ACC GGC CGC ATG GAC CCA GGG ACA GTG GCC      595
Phe Ala Gly Leu Pro Glu Thr Gly Arg Met Asp Pro Gly Thr Val Ala
                 55                  60                  65

ACC ATG CGT AAG CCC CGC TGC TCC CTG CCT GAC GTG CTG GGG GTG GCG      643
Thr Met Arg Lys Pro Arg Cys Ser Leu Pro Asp Val Leu Gly Val Ala
                 70                  75                  80

GGG CTG GTC AGG CGG CGT CGC CGG TAC GGT CTG AGC GGC AGC GTG TGG      691
Gly Leu Val Arg Arg Arg Arg Arg Tyr Gly Leu Ser Gly Ser Val Trp
             85                  90                  95

GAG AAG CGA ACC GTG ACA TGG AGG GTA CGT TCC TTC CCC CAG AGC TCC      739
Glu Lys Arg Thr Val Thr Trp Arg Val Arg Ser Phe Pro Gln Ser Ser
        100                 105                 110

CAG GTG AGC CAG GAG ACC GTG CGG GTC CTC GTG AGC TAT GCC CTG ATG      787
Gln Val Ser Gln Glu Thr Val Arg Val Leu Val Ser Tyr Ala Leu Met
115                 120                 125                 130

GCG TGG GGC ATG GAG TCA GGC CTC ACA TTT CAT GAG GTG GAT TCC CCC      835
Ala Trp Gly Met Glu Ser Gly Leu Thr Phe His Glu Val Asp Ser Pro
                135                 140                 145

CAG GGC CAG GAG CCC GAC ATC CTC ATA GAC TTT GCC CGC GCC TTC CAA      883
Gln Gly Gln Glu Pro Asp Ile Leu Ile Asp Phe Ala Arg Ala Phe Gln
            150                 155                 160

CAG GAC AGC TAC CCC TTC GAC GGG TTG GGG GGC ACC CTA GCC CAT GCC      931
Gln Asp Ser Tyr Pro Phe Asp Gly Leu Gly Gly Thr Leu Ala His Ala
        165                 170                 175

TTC TTC CCT GGG GAG CAC CCC ATC TCC GGG GAC ACT CAC TTT GAC GAT      979
Phe Phe Pro Gly Glu His Pro Ile Ser Gly Asp Thr His Phe Asp Asp
        180                 185                 190

GAG GAG ACC TGG ACT TTT GGG TCA AAA GAC GGC GAG GGG ACC GAC CTG     1027
Glu Glu Thr Trp Thr Phe Gly Ser Lys Asp Gly Glu Gly Thr Asp Leu
195                 200                 205                 210

TTT GCC GTG GCT GTC CAT GAG TTT GGC CAC GCC CTG GGC ATG GGC CAC     1075
Phe Ala Val Ala Val His Glu Phe Gly His Ala Leu Gly Met Gly His
                215                 220                 225

TCC TCA GCC CCC GAC TCC ATT ATG AGG CCC TTC TAC CAG GGT CCG GTG     1123
Ser Ser Ala Pro Asp Ser Ile Met Arg Pro Phe Tyr Gln Gly Pro Val
            230                 235                 240
```

-continued

```
GGC GAC CCT GAC AAG TAC CGC CTG TCT CTG GAT GAC CGC GAT GGC CTG         1171
Gly Asp Pro Asp Lys Tyr Arg Leu Ser Leu Asp Asp Arg Asp Gly Leu
        245                 250                 255

CAG CAA CTC TAT GGG AAG GCG CCC CAA ACC CCA TAT GAC AAG CCC ACA         1219
Gln Gln Leu Tyr Gly Lys Ala Pro Gln Thr Pro Tyr Asp Lys Pro Thr
260                 265                 270

AGG AAA CCC CTG GCT CCT CCG CCC CAG CCC CCG GCC TCG CCC ACA CAC         1267
Arg Lys Pro Leu Ala Pro Pro Pro Gln Pro Pro Ala Ser Pro Thr His
275                 280                 285                 290

AGC CCA TCC TTC CCC ATC CCT GAT CGA TGT GAG GGC AAT TTT GAC GCC         1315
Ser Pro Ser Phe Pro Ile Pro Asp Arg Cys Glu Gly Asn Phe Asp Ala
                295                 300                 305

ATC GCC AAC ATC CGA GGG GAA ACT TTC TTC TTC AAA GGC CCC TGG TTC         1363
Ile Ala Asn Ile Arg Gly Glu Thr Phe Phe Phe Lys Gly Pro Trp Phe
            310                 315                 320

TGG CGC CTC CAG CCC TCC GGA CAG CTG GTG TCC CCG CGA CCC GCA CGG         1411
Trp Arg Leu Gln Pro Ser Gly Gln Leu Val Ser Pro Arg Pro Ala Arg
        325                 330                 335

CTG CAC CGC TTC TGG GAG GGG CTG CCC GCC CAG GTG AGG GTG GTG CAG         1459
Leu His Arg Phe Trp Glu Gly Leu Pro Ala Gln Val Arg Val Val Gln
340                 345                 350

GCC GCC TAT GCT CGG CAC CGA GAC GGC CGA ATC CTC CTC TTT AGC GGG         1507
Ala Ala Tyr Ala Arg His Arg Asp Gly Arg Ile Leu Leu Phe Ser Gly
355                 360                 365                 370

CCC CAG TTC TGG GTG TTC CAG GAC CGG CAG CTG GAG GGC GGG GCG CGG         1555
Pro Gln Phe Trp Val Phe Gln Asp Arg Gln Leu Glu Gly Gly Ala Arg
                375                 380                 385

CCG CTC ACG GAG CTG GGG CTG CCC CCG GGA GAG GAG GTG GAC GCC GTG         1603
Pro Leu Thr Glu Leu Gly Leu Pro Pro Gly Glu Glu Val Asp Ala Val
            390                 395                 400

TTC TCG TGG CCA CAG AAC GGG AAG ACC TAC CTG GTC CGC GGC CGG CAG         1651
Phe Ser Trp Pro Gln Asn Gly Lys Thr Tyr Leu Val Arg Gly Arg Gln
        405                 410                 415

TAC TGG CGC TAC GAC GAG GCG GCG GCG CGC CCG GAC CCC GGC TAC CTT         1699
Tyr Trp Arg Tyr Asp Glu Ala Ala Ala Arg Pro Asp Pro Gly Tyr Leu
420                 425                 430

CGC GAC CTG AGC CTC TGG GAA GGC GCG CCC CCC TCC CCT GAC GAT GTC         1747
Arg Asp Leu Ser Leu Trp Glu Gly Ala Pro Pro Ser Pro Asp Asp Val
435                 440                 445                 450

ACC GTC AGC AAC GCA GGT GAC ACC TAC TTC TTC AAG GGC GCC CAC TAC         1795
Thr Val Ser Asn Ala Gly Asp Thr Tyr Phe Phe Lys Gly Ala His Tyr
                455                 460                 465

TGG CGC TTC CCC AAG AAC AGC ATC AAG ACC GAG CCG GAC GCC CCC CAG         1843
Trp Arg Phe Pro Lys Asn Ser Ile Lys Thr Glu Pro Asp Ala Pro Gln
            470                 475                 480

CCC ATG GGG CCC AAC TGG CTG GAC TGC CCC GCC CCG AGC TCT GGT CCC         1891
Pro Met Gly Pro Asn Trp Leu Asp Cys Pro Ala Pro Ser Ser Gly Pro
        485                 490                 495

CGC GCC CCC AGG CCC CCC AAA GGG ACC CCC GTG TCC GAA ACC TGC GAT         1939
Arg Ala Pro Arg Pro Pro Lys Gly Thr Pro Val Ser Glu Thr Cys Asp
500                 505                 510

TGT CAG TGC GAG CTC AAC CAG GCC GCA GGA CGT TGG CCT GCT CCC ATC         1987
Cys Gln Cys Glu Leu Asn Gln Ala Ala Gly Arg Trp Pro Ala Pro Ile
515                 520                 525                 530

CCG CTG CTC CTC TTG CCC CTG CTG GTG GGG GGT GTA GCC TCC CGC             2032
Pro Leu Leu Leu Leu Pro Leu Leu Val Gly Gly Val Ala Ser Arg
                535                 540                 545

TGATGGGGGG AGCCATCCAG ACCGAACAGC CCCTCCACG GCCGAGTCCC CCGCCGCTGG       2092

ACCTGGTCGG GGGTTGTGAG GCGCTGCGGA GGCCCCTTGT CTGTTCCCAC GGACGGGGGC      2152
```

-continued

```
TCGGGCGCGG ACTAAGCAGG GGGGATCTCC CGCGCAGGGG CGGCGGCGGC GGGGACCGGT    2212

CGCCTGGCGC TGGGCTCAGT CTCCTCAGGG TCTGAGACCC CGGCGCTGCC ACCGGAACCC    2272

GCCTTCAGGG GCGCACGCGC GCTGGGACCA TGCGTCGGTC GTCGCCCCCG TCGTTCCCTC    2332

CCGGCTGCCG CCAGGGGGCG GTCGGACCCC GCCTCCCGAG CCCGGGGAGG GGCGGGGAGG    2392

ACAAGGGGCG GGCCCGCGGC CTCACCCGGA GGGACGGCAG CCCCGGTCGC GCGCTGGCCC    2452

CGCAGGACCT TCCTTTTCCA GGAAGAGCCA GCTTTTCTCG GAGCGCAGTC CTGGGACTCT    2512

CCGCAGCCCC GCCCCGCCTG GCCACTGCGT CTGGCATTCC TGGGTCGTTA GAGGACAGGC    2572

CTGACTGCGA AGCTGTGCCT TGCCCCTCTC CCACCCGCAG TTTCTCACCC CGTTCTGCTC    2632

CCACAAGGCC CCCCTACAGT CACTGCCACA CTGGTGGGGA CCTGGGACCC AGACCCGGAA    2692

CCAGCCCAGA TATCACCCCT GAGGACCCAT GCGCCACGTC CTGGGTGGTG GAATCAGTGG    2752

GTGGAGGGAC GACCCTTGCT CTCCAGGCTG TTAACCTTTT CCGTTGCTCC CCCGCCACCC    2812

ACCTCCTCCT CCCCAGGCCA CCCAACTTGG GCACCTCCCT GGGCCCAGAA CTGCCTTCCA    2872

TTCAATGGGG AACCCTTCTA TCCCCAAGAA CCCCTTCCCT GCTTGCACCC TGGAGAGAAC    2932

AGCTTGACTC CCATCAACTC AACGCTGGTG GAAAGACAGG GACCGAACCC TGGCTCAGGC    2992

CTGGTCATTG CCTCCTCAGC ACTCCCTCCT GGGAGGCCTT AGCTCTAGAG TGAGGGGTGG    3052

GTGGAACCTG GGGGCACCTC GTTCACCCTG TCCCCACTCC CCACAGTTTT AGGATCTAAA    3112

TGATTGCCTC TGGAACTATT CTTCTAGACT ATCCCACATC AGAATCACTG GGAAATTTAA    3172

GTTTGCAGAT CCCACACTCA CCCTGAATCC TCACTCAGGG TGGGGTCAGG AATCTGCATT    3232

TTAACTAGTC GCGGGGATTG TGGGGGGCAG TAGCTGGCTG TTTCGTGGCA TTTCTGTGGC    3292

TCTGCAGTGT TCCTCCACCC CAGGACCAAT ATGTTCAGGC CACACCGATG GCCTGAACCC    3352

CATGGGTAGA GTCACTTAGG GGCCACTTCC TAAGTTGCTG TCCAGCCTCA GTGACCCCCT    3412

AGTGCTTCCT GGAGCTGAGG CTGTGGGCGG CTGTCCCAGC AACCAWGCGA GGGGTTGCCC    3472

CAGTTGCTCA TACAAACAGA TCAGCATGAG GACAGAAGGC AGGAGACTTT GGTCAGTTAC    3532

CTGGGAATTC TGGGCTGCCA GGAAACGATT TGGGCCTCTG TCAGTTTCTT TTCCATGTAT    3592

GAGGAGGGGG AAATTTGTAT ATTAGATACT TATTCATCCC ACTCTGGACA ATAAAAACGA    3652

ATGTACAAAA AAAACATAAA AAAAAAAAAT AAAGAAAATC AAA                     3695
```

(2) INFORMATION FOR SEQ ID NO:2:

(i) SEQUENCE CHARACTERISTICS:
        (A) LENGTH: 563 amino acids
        (B) TYPE: amino acid
        (D) TOPOLOGY: linear (ii) MOLECULE TYPE: protein (xi) SEQUENCE DESCRIPTION: SEQ ID NO:2:

```
Met Arg Leu Arg Leu Arg Leu Leu Ala Leu Leu Leu His Ala Gly
-18         -15             -10              -5

Thr Ala Arg Ala Arg Pro Glu Ala Leu Gly Ala Gly Leu Ser Leu Gly
         1           5                  10

Cys Glu Asn Trp Leu Thr Arg Tyr Gly Tyr Leu Pro Pro Asp Pro
 15              20              25                  30

Ala Gln Ala Gln Leu Gln Ser Pro Glu Asn Leu Arg Asp Ala Ile Lys
                 35              40                  45

Val Met Gln Arg Phe Ala Gly Leu Pro Glu Thr Gly Arg Met Asp Pro
         50              55              60
```

-continued

Gly Thr Val Ala Thr Met Arg Lys Pro Arg Cys Ser Leu Pro Asp Val
            65                  70                  75
Leu Gly Val Ala Gly Leu Val Arg Arg Arg Arg Tyr Gly Leu Ser
 80                  85                  90
Gly Ser Val Trp Glu Lys Arg Thr Val Thr Trp Arg Val Arg Ser Phe
 95                 100                 105                 110
Pro Gln Ser Ser Gln Val Ser Gln Glu Thr Val Arg Val Leu Val Ser
                115                 120                 125
Tyr Ala Leu Met Ala Trp Gly Met Glu Ser Gly Leu Thr Phe His Glu
            130                 135                 140
Val Asp Ser Pro Gln Gly Gln Glu Pro Asp Ile Leu Ile Asp Phe Ala
            145                 150                 155
Arg Ala Phe Gln Gln Asp Ser Tyr Pro Phe Asp Gly Leu Gly Gly Thr
160                 165                 170
Leu Ala His Ala Phe Phe Pro Gly Glu His Pro Ile Ser Gly Asp Thr
175                 180                 185                 190
His Phe Asp Asp Glu Glu Thr Trp Thr Phe Gly Ser Lys Asp Gly Glu
                195                 200                 205
Gly Thr Asp Leu Phe Ala Val Ala Val His Glu Phe Gly His Ala Leu
            210                 215                 220
Gly Met Gly His Ser Ser Ala Pro Asp Ser Ile Met Arg Pro Phe Tyr
            225                 230                 235
Gln Gly Pro Val Gly Asp Pro Asp Lys Tyr Arg Leu Ser Leu Asp Asp
            240                 245                 250
Arg Asp Gly Leu Gln Gln Leu Tyr Gly Lys Ala Pro Gln Thr Pro Tyr
255                 260                 265                 270
Asp Lys Pro Thr Arg Lys Pro Leu Ala Pro Pro Gln Pro Pro Ala
                275                 280                 285
Ser Pro Thr His Ser Pro Ser Phe Pro Ile Pro Asp Arg Cys Glu Gly
            290                 295                 300
Asn Phe Asp Ala Ile Ala Asn Ile Arg Gly Glu Thr Phe Phe Phe Lys
            305                 310                 315
Gly Pro Trp Phe Trp Arg Leu Gln Pro Ser Gly Gln Leu Val Ser Pro
            320                 325                 330
Arg Pro Ala Arg Leu His Arg Phe Trp Glu Gly Leu Pro Ala Gln Val
335                 340                 345                 350
Arg Val Val Gln Ala Ala Tyr Ala Arg His Arg Asp Gly Arg Ile Leu
                355                 360                 365
Leu Phe Ser Gly Pro Gln Phe Trp Val Phe Gln Asp Arg Gln Leu Glu
            370                 375                 380
Gly Gly Ala Arg Pro Leu Thr Glu Leu Gly Leu Pro Pro Gly Glu Glu
            385                 390                 395
Val Asp Ala Val Phe Ser Trp Pro Gln Asn Gly Lys Thr Tyr Leu Val
            400                 405                 410
Arg Gly Arg Gln Tyr Trp Arg Tyr Asp Glu Ala Ala Arg Pro Asp
415                 420                 425                 430
Pro Gly Tyr Leu Arg Asp Leu Ser Leu Trp Glu Gly Ala Pro Pro Ser
                435                 440                 445
Pro Asp Asp Val Thr Val Ser Asn Ala Gly Asp Thr Tyr Phe Phe Lys
            450                 455                 460
Gly Ala His Tyr Trp Arg Phe Pro Lys Asn Ser Ile Lys Thr Glu Pro
            465                 470                 475

```
Asp Ala Pro Gln Pro Met Gly Pro Asn Trp Leu Asp Cys Pro Ala Pro
    480                 485                 490

Ser Ser Gly Pro Arg Ala Pro Arg Pro Pro Lys Gly Thr Pro Val Ser
495                 500                 505                 510

Glu Thr Cys Asp Cys Gln Cys Glu Leu Asn Gln Ala Ala Gly Arg Trp
                515                 520                 525

Pro Ala Pro Ile Pro Leu Leu Leu Leu Pro Leu Leu Val Gly Gly Val
                530                 535                 540

Ala Ser Arg
    545
```

(2) INFORMATION FOR SEQ ID NO:3:

(i) SEQUENCE CHARACTERISTICS:
        (A) LENGTH: 3691 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 343..2028

(ix) FEATURE:
        (A) NAME/KEY: mat_peptide
        (B) LOCATION: 406..2028

(ix) FEATURE:
        (A) NAME/KEY: misc_feature
        (B) LOCATION: 3454
        (D) OTHER INFORMATION: /note= "nucleotide 3454 designated W,
            may be A or T."

(xi) SEQUENCE DESCRIPTION: SEQ ID NO:3:

```
CATGCAACAT AATCTTGCTC GATTCTAAAG TCAACGGATC CTGCAAAATT CGCGGCCGCG       60

TCAACCCATT AGGTCTTGGC CTTGGAATAA AATTGCTTCT CGTCTGATTC CCGGGCCCAC      120

CCGACCCAGC GGCGCAACCC TGGCCCTCCG GGACCCTCCG CTGACTCCAC CGCGCACTTC      180

CCGGGACCCC CACACACATC CCAGCCCTCC GGCCGATCCC TCCCTACTCG GTGCCGGGTG      240

CCCCCCGCCC TCTCCAGGCC CGGATCTCCT CCCCCAGGTC CCCGGGCGG CCCCAGCCAG       300

GCCCCCTTCG AACCCCGCCG GCGGCCCGGG CTGGGGCGCA CC ATG CGG CTG CGG        354
                                             Met Arg Leu Arg
                                             -21 -20

CTC CGG CTT CTG GCG CTG CTG CTT CTG CTG CTG GCA CCG CCC GCG CGC        402
Leu Arg Leu Leu Ala Leu Leu Leu Leu Leu Leu Ala Pro Pro Ala Arg
        -15                 -10                  -5

GCC CCG AAG CCC TCG GCG CAG GAC GTG AGC CTG GGC GTG GAC TGG CTG        450
Ala Pro Lys Pro Ser Ala Gln Asp Val Ser Leu Gly Val Asp Trp Leu
 1                5                  10                  15

ACT CGC TAT GGT TAC CTG CCG CCA CCC CAC CCT GCC CAG GCC CAG CTG        498
Thr Arg Tyr Gly Tyr Leu Pro Pro Pro His Pro Ala Gln Ala Gln Leu
                20                  25                  30

CAG AGC CCT GAG AAG TTG CGC GAT GCC ATC AAA GTC ATG CAG AGG TTC        546
Gln Ser Pro Glu Lys Leu Arg Asp Ala Ile Lys Val Met Gln Arg Phe
                35                  40                  45

GCG GGG CTG CCG GAG ACC GGC CGC ATG GAC CCA GGG ACA GTG GCC ACC        594
Ala Gly Leu Pro Glu Thr Gly Arg Met Asp Pro Gly Thr Val Ala Thr
         50                  55                  60

ATG CGT AAG CCC CGC TGC TCC CTG CCT GAC GTG CTG GGG GTG GCG GGG        642
Met Arg Lys Pro Arg Cys Ser Leu Pro Asp Val Leu Gly Val Ala Gly
```

|   |   |
|---|---|
| CTG GTC AGG CGG CGT CGC CGG TAC GCT CTG AGC GGC AGC GTG TGG AAG<br>Leu Val Arg Arg Arg Arg Arg Tyr Ala Leu Ser Gly Ser Val Trp Lys<br>80                     85                     90                     95 | 690 |
| AAG CGA ACC CTG ACA TGG AGG GTA CGT TCC TTC CCC CAG AGC TCC CAG<br>Lys Arg Thr Leu Thr Trp Arg Val Arg Ser Phe Pro Gln Ser Ser Gln<br>                     100                     105                   110 | 738 |
| CTG AGC CAG GAG ACC GTG CGG GTC CTC ATG AGC TAT GCC CTG ATG GCC<br>Leu Ser Gln Glu Thr Val Arg Val Leu Met Ser Tyr Ala Leu Met Ala<br>             115                     120                     125 | 786 |
| TGG GGC ATG GAG TCA GGC CTC ACA TTT CAT GAG GTG GAT TCC CCC CAG<br>Trp Gly Met Glu Ser Gly Leu Thr Phe His Glu Val Asp Ser Pro Gln<br>130                     135                     140 | 834 |
| GGC CAG GAG CCC GAC ATC CTC ATC GAC TTT GCC CGC GCC TTC CAC CAG<br>Gly Gln Glu Pro Asp Ile Leu Ile Asp Phe Ala Arg Ala Phe His Gln<br>145                     150                     155 | 882 |
| GAC AGC TAC CCC TTC GAC GGG TTG GGG GGC ACC CTA GCC CAT GCC TTC<br>Asp Ser Tyr Pro Phe Asp Gly Leu Gly Gly Thr Leu Ala His Ala Phe<br>160                     165                     170                     175 | 930 |
| TTC CCT GGG GAG CAC CCC ATC TCC GGG GAC ACT CAC TTT GAC GAT GAG<br>Phe Pro Gly Glu His Pro Ile Ser Gly Asp Thr His Phe Asp Asp Glu<br>             180                     185                     190 | 978 |
| GAG ACC TGG ACT TTT GGG TCA AAA GAC GGC GAG GGG ACC GAC CTG TTT<br>Glu Thr Trp Thr Phe Gly Ser Lys Asp Gly Glu Gly Thr Asp Leu Phe<br>195                     200                     205 | 1026 |
| GCC GTG GCT GTC CAT GAG TTT GGC CAC GCC CTG GGC CTG GGC CAC TCC<br>Ala Val Ala Val His Glu Phe Gly His Ala Leu Gly Leu Gly His Ser<br>             210                     215                     220 | 1074 |
| TCA GCC CCC AAC TCC ATT ATG AGG CCC TTC TAC CAG GGT CCG GTG GGC<br>Ser Ala Pro Asn Ser Ile Met Arg Pro Phe Tyr Gln Gly Pro Val Gly<br>225                     230                     235 | 1122 |
| GAC CCT GAC AAG TAC CGC CTG TCT CAG GAT GAC CGC GAT GGC CTG CAG<br>Asp Pro Asp Lys Tyr Arg Leu Ser Gln Asp Asp Arg Asp Gly Leu Gln<br>240                     245                     250                     255 | 1170 |
| CAA CTC TAT GGG AAG GCG CCC CAA ACC CCA TAT GAC AAG CCC ACA AGG<br>Gln Leu Tyr Gly Lys Ala Pro Gln Thr Pro Tyr Asp Lys Pro Thr Arg<br>             260                     265                     270 | 1218 |
| AAA CCC CTG GCT CCT CCG CCC CAG CCC CCG GCC TCG CCC ACA CAC AGC<br>Lys Pro Leu Ala Pro Pro Pro Gln Pro Pro Ala Ser Pro Thr His Ser<br>             275                     280                     285 | 1266 |
| CCA TCC TTC CCC ATC CCT GAT CGA TGT GAG GGC AAT TTT GAC GCC ATC<br>Pro Ser Phe Pro Ile Pro Asp Arg Cys Glu Gly Asn Phe Asp Ala Ile<br>             290                     295                     300 | 1314 |
| GCC AAC ATC CGA GGG GAA ACT TTC TTC TTC AAA GGC CCC TGG TTC TGG<br>Ala Asn Ile Arg Gly Glu Thr Phe Phe Phe Lys Gly Pro Trp Phe Trp<br>305                     310                     315 | 1362 |
| CGC CTC CAG CCC TCC GGA CAG CTG GTG TCC CCG CGA CCC GCA CGG CTG<br>Arg Leu Gln Pro Ser Gly Gln Leu Val Ser Pro Arg Pro Ala Arg Leu<br>320                     325                     330                     335 | 1410 |
| CAC CGC TTC TGG GAG GGG CTG CCC GCC CAG GTG AGG GTG GTG CAG GCC<br>His Arg Phe Trp Glu Gly Leu Pro Ala Gln Val Arg Val Val Gln Ala<br>             340                     345                     350 | 1458 |
| GCC TAT GCT CGG CAC CGA GAC GGC CGA ATC CTC CTC TTT AGC GGG CCC<br>Ala Tyr Ala Arg His Arg Asp Gly Arg Ile Leu Leu Phe Ser Gly Pro<br>             355                     360                     365 | 1506 |
| CAG TTC TGG GTG TTC CAG GAC CGG CAG CTG GAG GGC GGG GCG CGG CCG<br>Gln Phe Trp Val Phe Gln Asp Arg Gln Leu Glu Gly Gly Ala Arg Pro<br>             370                     375                     380 | 1554 |
| CTC ACG GAG CTG GGG CTG CCC CCG GGA GAG GAG GTG GAC GCC GTG TTC | 1602 |

```
Leu Thr Glu Leu Gly Leu Pro Pro Gly Glu Glu Val Asp Ala Val Phe
    385                 390                 395

TCG TGG CCA CAG AAC GGG AAG ACC TAC CTG GTC CGC GGC CGG CAG TAC      1650
Ser Trp Pro Gln Asn Gly Lys Thr Tyr Leu Val Arg Gly Arg Gln Tyr
400                 405                 410                 415

TGG CGC TAC GAC GAG GCG GCG GCG CGC CCG GAC CCC GGC TAC CCT CGC      1698
Trp Arg Tyr Asp Glu Ala Ala Ala Arg Pro Asp Pro Gly Tyr Pro Arg
                420                 425                 430

GAC CTG AGC CTC TGG GAA GGC GCG CCC CCC TCC CCT GAC GAT GTC ACC      1746
Asp Leu Ser Leu Trp Glu Gly Ala Pro Pro Ser Pro Asp Asp Val Thr
            435                 440                 445

GTC AGC AAC GCA GGT GAC ACC TAC TTC TTC AAG GGC GCC CAC TAC TGG      1794
Val Ser Asn Ala Gly Asp Thr Tyr Phe Phe Lys Gly Ala His Tyr Trp
        450                 455                 460

CGC TTC CCC AAG AAC AGC ATC AAG ACC GAG CCG GAC GCC CCC CAG CCC      1842
Arg Phe Pro Lys Asn Ser Ile Lys Thr Glu Pro Asp Ala Pro Gln Pro
    465                 470                 475

ATG GGG CCC AAC TGG CTG GAC TGC CCC GCC CCG AGC TCT GGT CCC CGC      1890
Met Gly Pro Asn Trp Leu Asp Cys Pro Ala Pro Ser Ser Gly Pro Arg
480                 485                 490                 495

GCC CCC AGG CCC CCC AAA GCG ACC CCC GTG TCC GAA ACC TGC GAT TGT      1938
Ala Pro Arg Pro Pro Lys Ala Thr Pro Val Ser Glu Thr Cys Asp Cys
                500                 505                 510

CAG TGC GAG CTC AAC CAG GCC GCA GGA CGT TGG CCT GCT CCC ATC CCG      1986
Gln Cys Glu Leu Asn Gln Ala Ala Gly Arg Trp Pro Ala Pro Ile Pro
            515                 520                 525

CTG CTC CTC TTG CCC CTG CTG GTG GGG GGT GTA GCC TCC CGC              2028
Leu Leu Leu Leu Pro Leu Leu Val Gly Gly Val Ala Ser Arg
        530                 535                 540

TGATGGGGGG AGCCATCCAG ACCGAACAGC GCCCTCCACG GCCGAGTCCC CCGCCGCTGG    2088

ACCTGGTCGG GGGTTGTGAG GCGCTGCGGA GGCCCCTTGT CTGTTCCCAC GGACGGGGGC    2148

TCGGGCGCGG ACTAAGCAGG GGGGATCTCC CGCGCAGGGG CGGCGGCGGC GGGGACCGGT    2208

CGCCTGGCGC TGGGCTCAGT CTCCTCAGGG TCTGAGACCC CGGCGCTGCC ACCGGAACCC    2268

GCCTTCAGGG GCGCACGCGC GCTGGGACCA TGCGTCGGTC GTCGCCCCCG TCGTTCCCTC    2328

CCGGCTGCCG CCAGGGGGCG GTCGGACCCC GCCTCCCGAG CCCGGGGAGG GGCGGGGAGG    2388

ACAAGGGGCG GGCCCGCGGC CTCACCCGGA GGGACGGCAG CCCCGGTCGC GCGCTGGCCC    2448

CGCAGGACCT TCCTTTTCCA GGAAGAGCCA GCTTTTCTCG GAGCGCAGTC CTGGGACTCT    2508

CCGCAGCCCC GCCCCGCCTG CCACTGCGT CTGGCATTCC TGGGTCGTTA GAGGACAGGC     2568

CTGACTGCGA AGCTGTGCCT TGCCCCTCTC CCACCCGCAG TTTCTCACCC CGTTCTGCTC    2628

CCACAAGGCC CCCCTACAGT CACTGCCACA CTGGTGGGGA CCTGGGACCC AGACCCGGAA    2688

CCAGCCCAGA TATCACCCCT GAGGACCCAT GCGCCACGTC CTGGGTGGTG AATCAGTGG     2748

CTGGAGGGAC GACCCTTGCT CTCCAGGCTG TTAACCTTTT CCGTTGCTCC CCCGCCACCC    2808

ACCTCCTCCT CCCCAGGCCA CCCAACTTGG GCACCTCCCT GGGCCCAGAA CTGCCTTCCA    2868

TTCAATGGGG AACCCTTCTA TCCCCAAGAA CCCCTTCCCT GCTTGCACCC TGGAGAGAAC    2928

AGCTTGACTC CCATCAACTC AACGCTGGTG GAAAGACAGG GACCGAACCC TGGCTCAGGC    2988

CTGGTCATTG CCTCCTCAGC ACTCCCTCCT GGGAGGCCTT AGCTCTAGAG TGAGGGGTGG    3048

GTGGAACCTG GGGGCACCTC GTTCACCCTG TCCCCACTCC CCACAGTTTT AGGATCTAAA    3108

TGATTGCCTC TGGAACTATT CTTCTAGACT ATCCACACATC AGAATCACTG GGAAATTTAA   3168

GTTTGCAGAT CCCACACTCA CCCTGAATCC TCACTCAGGG TGGGGTCAGG AATCTGCATT    3228
```

-continued

```
TTAACTAGTC GCGGGGATTG TGGGGGGCAG TAGCTGGCTG TTTCGTGGCA TTTCTGTGGC    3288

TCTGCAGTGT TCCTCCACCC CAGGACCAAT ATGTTCAGGC CACACCGATG GCCTGAACCC    3348

CATGGGTAGA GTCACTTAGG GGCCACTTCC TAAGTTGCTG TCCAGCCTCA GTGACCCCCT    3408

AGTGCTTCCT GGAGCTGAGG CTGTGGGCGG CTGTCCCAGC AACCAWGCGA GGGGTTGCCC    3468

CAGTTGCTCA TACAAACAGA TCAGCATGAG GACAGAAGGC AGGAGACTTT GGTCAGTTAC    3528

CTGGGAATTC TGGGCTGCCA GGAAACGATT TGGGCCTCTG TCAGTTTCTT TTCCATGTAT    3588

GAGGAGGGGG AAATTTGTAT ATTAGATACT TATTCATCCC ACTCTGGACA ATAAAAACGA    3648

ATGTACAAAA AAAACATAAA AAAAAAAAAT AAAGAAAATC AAA                      3691
```

(2) INFORMATION FOR SEQ ID NO:4:

(i) SEQUENCE CHARACTERISTICS:
        (A) LENGTH: 562 amino acids
        (B) TYPE: amino acid
        (D) TOPOLOGY: linear (ii) MOLECULE TYPE: protein (xi) SEQUENCE DESCRIPTION: SEQ ID NO:4:

```
Met Arg Leu Arg Leu Arg Leu Leu Ala Leu Leu Leu Leu Leu Ala
-21 -20              -15              -10

Pro Pro Ala Arg Ala Pro Lys Pro Ser Ala Gln Asp Val Ser Leu Gly
 -5               1               5                  10

Val Asp Trp Leu Thr Arg Tyr Gly Tyr Leu Pro Pro His Pro Ala
             15              20              25

Gln Ala Gln Leu Gln Ser Pro Glu Lys Leu Arg Asp Ala Ile Lys Val
         30              35              40

Met Gln Arg Phe Ala Gly Leu Pro Glu Thr Gly Arg Met Asp Pro Gly
         45              50              55

Thr Val Ala Thr Met Arg Lys Pro Arg Cys Ser Leu Pro Asp Val Leu
 60              65              70              75

Gly Val Ala Gly Leu Val Arg Arg Arg Arg Tyr Ala Leu Ser Gly
             80              85              90

Ser Val Trp Lys Lys Arg Thr Leu Thr Trp Arg Val Arg Ser Phe Pro
             95              100             105

Gln Ser Ser Gln Leu Ser Gln Glu Thr Val Arg Val Leu Met Ser Tyr
         110             115             120

Ala Leu Met Ala Trp Gly Met Glu Ser Gly Leu Thr Phe His Glu Val
         125             130             135

Asp Ser Pro Gln Gly Gln Glu Pro Asp Ile Leu Ile Asp Phe Ala Arg
140             145             150             155

Ala Phe His Gln Asp Ser Tyr Pro Phe Asp Gly Leu Gly Gly Thr Leu
             160             165             170

Ala His Ala Phe Phe Pro Gly Glu His Pro Ile Ser Gly Asp Thr His
             175             180             185

Phe Asp Asp Glu Glu Thr Trp Thr Phe Gly Ser Lys Asp Gly Glu Gly
             190             195             200

Thr Asp Leu Phe Ala Val Ala Val His Glu Phe Gly His Ala Leu Gly
         205             210             215

Leu Gly His Ser Ser Ala Pro Asn Ser Ile Met Arg Pro Phe Tyr Gln
220             225             230             235

Gly Pro Val Gly Asp Pro Asp Lys Tyr Arg Leu Ser Gln Asp Asp Arg
             240             245             250
```

-continued

```
Asp Gly Leu Gln Gln Leu Tyr Gly Lys Ala Pro Gln Thr Pro Tyr Asp
            255                 260                 265

Lys Pro Thr Arg Lys Pro Leu Ala Pro Pro Gln Pro Pro Ala Ser
            270                 275                 280

Pro Thr His Ser Pro Ser Phe Pro Ile Pro Asp Arg Cys Glu Gly Asn
            285                 290                 295

Phe Asp Ala Ile Ala Asn Ile Arg Gly Glu Thr Phe Phe Lys Gly
300                 305                 310                 315

Pro Trp Phe Trp Arg Leu Gln Pro Ser Gly Gln Leu Val Ser Pro Arg
                320                 325                 330

Pro Ala Arg Leu His Arg Phe Trp Glu Gly Leu Pro Ala Gln Val Arg
                335                 340                 345

Val Val Gln Ala Ala Tyr Ala Arg His Arg Asp Gly Arg Ile Leu Leu
                350                 355                 360

Phe Ser Gly Pro Gln Phe Trp Val Phe Gln Asp Arg Gln Leu Glu Gly
365                 370                 375

Gly Ala Arg Pro Leu Thr Glu Leu Gly Leu Pro Pro Gly Glu Glu Val
380                 385                 390                 395

Asp Ala Val Phe Ser Trp Pro Gln Asn Gly Lys Thr Tyr Leu Val Arg
                400                 405                 410

Gly Arg Gln Tyr Trp Arg Tyr Asp Glu Ala Ala Arg Pro Asp Pro
                415                 420                 425

Gly Tyr Pro Arg Asp Leu Ser Leu Trp Glu Gly Ala Pro Ser Pro
                430                 435                 440

Asp Asp Val Thr Val Ser Asn Ala Gly Asp Thr Tyr Phe Lys Gly
                445                 450                 455

Ala His Tyr Trp Arg Phe Pro Lys Asn Ser Ile Lys Thr Glu Pro Asp
460                 465                 470                 475

Ala Pro Gln Pro Met Gly Pro Asn Trp Leu Asp Cys Pro Ala Pro Ser
                480                 485                 490

Ser Gly Pro Arg Ala Pro Arg Pro Lys Ala Thr Pro Val Ser Glu
                495                 500                 505

Thr Cys Asp Cys Gln Cys Glu Leu Asn Gln Ala Ala Gly Arg Trp Pro
                510                 515                 520

Ala Pro Ile Pro Leu Leu Leu Leu Pro Leu Leu Val Gly Gly Val Ala
            525                 530                 535

Ser Arg
540

(2) INFORMATION FOR SEQ ID NO:5:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:5:

CAGAAATGCC ACGAAACAGC CAGGTACT                                      28

(2) INFORMATION FOR SEQ ID NO:6:

(i) SEQUENCE CHARACTERISTICS:
        (A) LENGTH: 28 base pairs
        (B) TYPE: nucleic acid
```

```
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:6:

GCCCCAGTTG CTCATACAAA CAGATCAG                                              28

(2) INFORMATION FOR SEQ ID NO:7:

(i) SEQUENCE CHARACTERISTICS:
        (A) LENGTH: 519 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO:7:
```

Met Gln Gln Phe Gly Gly Leu Glu Ala Thr Gly Ile Leu Asp Glu Ala
1               5                   10                  15

Thr Leu Ala Leu Met Lys Thr Pro Arg Cys Ser Leu Pro Asp Leu Pro
            20                  25                  30

Val Leu Thr Gln Ala Arg Arg Arg Gln Ala Pro Ala Pro Thr Lys
        35                  40                  45

Trp Asn Lys Arg Asn Leu Ser Trp Arg Val Arg Thr Phe Pro Arg Asp
 50                 55                  60

Ser Pro Leu Gly His Asp Thr Val Arg Ala Leu Met Tyr Tyr Ala Leu
65                  70                  75                  80

Lys Val Trp Ser Asp Ile Ala Pro Leu Asn Phe His Glu Val Ala Gly
                85                  90                  95

Ser Thr Ala Asp Ile Gln Ile Asp Phe Ser Lys Ala Asp His Asn Asp
            100                 105                 110

Gly Tyr Pro Phe Asp Gly Pro Gly Gly Thr Val Ala His Ala Phe Phe
        115                 120                 125

Pro Gly His His His Thr Ala Gly Asp Thr His Phe Asp Asp Asp Glu
    130                 135                 140

Ala Trp Thr Phe Arg Ser Ser Asp Ala His Gly Met Asp Leu Phe Ala
145                 150                 155                 160

Val Ala Val His Glu Phe Gly His Ala Ile Gly Leu Ser His Val Ala
                165                 170                 175

Ala Ala His Ser Ile Met Arg Pro Tyr Tyr Gln Gly Pro Val Gly Asp
            180                 185                 190

Pro Leu Arg Tyr Gly Leu Pro Tyr Glu Asp Lys Val Arg Val Trp Gln
        195                 200                 205

Leu Tyr Gly Val Arg Glu Ser Val Ser Pro Thr Ala Gln Pro Glu Glu
    210                 215                 220

Pro Pro Leu Leu Pro Glu Pro Pro Asp Asn Arg Ser Ser Ala Pro Pro
225                 230                 235                 240

Arg Lys Asp Val Pro His Arg Cys Ser Thr His Phe Asp Ala Val Ala
                245                 250                 255

Gln Ile Arg Gly Glu Ala Phe Phe Phe Lys Gly Lys Tyr Phe Trp Arg
            260                 265                 270

Leu Thr Arg Asp Arg His Leu Val Ser Leu Gln Pro Ala Gln Met His
        275                 280                 285

Arg Phe Trp Arg Gly Leu Pro Leu His Leu Asp Ser Val Asp Ala Val
    290                 295                 300

-continued

```
Tyr Glu Arg Thr Ser Asp His Lys Ile Val Phe Phe Lys Gly Asp Arg
305                 310                 315                 320

Tyr Trp Val Phe Lys Asp Asn Asn Val Glu Glu Gly Tyr Pro Arg Pro
                325                 330                 335

Val Ser Asp Phe Ser Leu Pro Pro Gly Gly Ile Asp Ala Ala Phe Ser
            340                 345                 350

Trp Ala His Asn Asp Arg Thr Tyr Phe Phe Lys Asp Gln Leu Tyr Trp
        355                 360                 365

Arg Tyr Asp Asp His Thr Arg His Met Asp Pro Gly Tyr Pro Ala Gln
    370                 375                 380

Ser Pro Leu Trp Arg Gly Val Pro Ser Thr Leu Asp Asp Ala Met Arg
385                 390                 395                 400

Trp Ser Asp Gly Ala Ser Tyr Phe Phe Arg Gly Gln Glu Tyr Trp Lys
                405                 410                 415

Val Leu Asp Gly Glu Leu Glu Val Ala Pro Gly Tyr Pro Gln Ser Thr
            420                 425                 430

Ala Arg Asp Trp Leu Val Cys Gly Asp Ser Gln Ala Asp Gly Ser Val
        435                 440                 445

Ala Ala Gly Val Asp Ala Ala Glu Gly Pro Arg Ala Pro Pro Gly Gln
    450                 455                 460

His Asp Gln Ser Arg Ser Glu Asp Gly Tyr Glu Val Cys Ser Cys Thr
465                 470                 475                 480

Ser Gly Ala Ser Ser Pro Pro Gly Ala Pro Gly Pro Leu Val Ala Ala
                485                 490                 495

Thr Met Leu Leu Leu Leu Pro Pro Leu Ser Pro Gly Ala Leu Trp Thr
            500                 505                 510

Ala Ala Gln Ala Leu Thr Leu
        515
```

(2) INFORMATION FOR SEQ ID NO:8:

(i) SEQUENCE CHARACTERISTICS:
        (A) LENGTH: 564 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO:8:

```
Met Lys Arg Pro Arg Cys Gly Val Pro Asp Gln Phe Gly Val Arg Val
1               5                   10                  15

Lys Ala Asn Leu Arg Arg Arg Arg Lys Arg Tyr Ala Leu Thr Gly Arg
            20                  25                  30

Lys Trp Asn Asn His His Leu Thr Phe Ser Ile Gln Asn Tyr Thr Glu
        35                  40                  45

Lys Leu Gly Trp Tyr His Ser Met Glu Ala Val Arg Arg Ala Phe Arg
    50                  55                  60

Val Trp Glu Gln Ala Thr Pro Leu Val Phe Gln Glu Val Pro Tyr Glu
65                  70                  75                  80

Asp Ile Arg Leu Arg Arg Gln Lys Glu Ala Asp Ile Met Val Leu Phe
                85                  90                  95

Ala Ser Gly Phe His Gly Asp Ser Ser Pro Phe Asp Gly Thr Gly Gly
            100                 105                 110

Phe Leu Ala His Ala Tyr Phe Pro Gly Pro Gly Leu Gly Gly Asp Thr
        115                 120                 125
```

-continued

```
His Phe Asp Ala Asp Glu Pro Trp Thr Phe Ser Ser Thr Asp Leu His
    130                 135                 140

Gly Asn Asn Leu Phe Leu Val Ala Val His Glu Leu Gly His Ala Leu
145                 150                 155                 160

Gly Leu Glu His Ser Ser Asn Pro Asn Ala Ile Met Ala Pro Phe Tyr
                165                 170                 175

Gln Trp Lys Asp Val Asp Asn Phe Lys Leu Pro Glu Asp Asp Leu Arg
            180                 185                 190

Gly Ile Gln Gln Leu Tyr Gly Thr Pro Asp Gly Gln Pro Gln Pro Thr
        195                 200                 205

Gln Pro Leu Pro Thr Val Thr Pro Arg Arg Pro Gly Arg Pro Asp His
    210                 215                 220

Arg Pro Pro Arg Pro Pro Gln Pro Pro Pro Gly Gly Lys Pro Glu
225                 230                 235                 240

Arg Pro Pro Lys Pro Gly Pro Pro Val Gln Pro Arg Ala Thr Glu Arg
                245                 250                 255

Pro Asp Gln Tyr Gly Pro Asn Ile Cys Asp Gly Asp Phe Asp Thr Val
                260                 265                 270

Ala Met Leu Arg Gly Glu Met Phe Val Phe Lys Gly Arg Trp Phe Trp
    275                 280                 285

Arg Val Arg His Asn Arg Val Leu Asp Asn Tyr Pro Met Pro Ile Gly
    290                 295                 300

His Phe Trp Arg Gly Leu Pro Gly Asp Ile Ser Ala Ala Tyr Glu Arg
305                 310                 315                 320

Gln Asp Gly Arg Phe Val Phe Phe Lys Gly Asp Arg Tyr Trp Leu Phe
                325                 330                 335

Arg Glu Ala Asn Leu Glu Pro Gly Tyr Pro Gln Pro Leu Thr Ser Tyr
                340                 345                 350

Gly Leu Gly Ile Pro Tyr Asp Arg Ile Asp Thr Ala Ile Trp Trp Glu
            355                 360                 365

Pro Thr Gly His Thr Phe Phe Phe Gln Glu Asp Arg Tyr Trp Arg Phe
    370                 375                 380

Asn Glu Glu Thr Gln Arg Gly Asp Pro Gly Tyr Pro Lys Pro Ile Ser
385                 390                 395                 400

Val Trp Gln Gly Ile Pro Ala Ser Pro Lys Gly Ala Phe Leu Ser Asn
                405                 410                 415

Asp Ala Ala Tyr Thr Tyr Phe Tyr Lys Gly Thr Lys Tyr Trp Lys Phe
                420                 425                 430

Asp Asn Glu Arg Leu Arg Met Glu Pro Gly Tyr Pro Lys Ser Ile Leu
            435                 440                 445

Arg Asp Phe Met Gly Cys Gln Glu His Val Glu Pro Gly Pro Arg Trp
    450                 455                 460

Pro Asp Val Ala Arg Pro Pro Phe Asn Pro His Gly Gly Ala Glu Pro
465                 470                 475                 480

Gly Ala Asp Ser Ala Glu Gly Asp Val Gly Asp Gly Asp Phe
                485                 490                 495

Gly Ala Gly Val Asn Lys Asp Arg Gly Ser Arg Val Val Gln Met
                500                 505                 510

Glu Glu Val Ala Arg Thr Val Asn Val Val Met Val Leu Val Pro Leu
            515                 520                 525

Leu Leu Leu Leu Cys Val Leu Gly Leu Thr Tyr Ala Leu Val Gln Met
    530                 535                 540
```

-continued

```
Gln Arg Lys Gly Ala Pro Arg Val Leu Leu Tyr Cys Lys Arg Ser Leu
545                 550                 555                 560

Gln Glu Trp Val
```

(2) INFORMATION FOR SEQ ID NO:9:

(i) SEQUENCE CHARACTERISTICS:
        (A) LENGTH: 582 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO:9:

```
Met Ser Pro Ala Pro Arg Pro Ser Arg Cys Leu Leu Pro Leu Leu
1               5                   10                  15

Thr Leu Gly Thr Ala Leu Ala Ser Leu Gly Ser Ala Gln Ser Ser
                20                  25                  30

Phe Ser Pro Glu Ala Trp Leu Gln Gln Tyr Gly Tyr Leu Pro Pro Gly
                35                  40                  45

Asp Leu Arg Thr His Thr Gln Arg Ser Pro Gln Ser Leu Ser Ala Ala
            50                  55                  60

Ile Ala Ala Met Gln Lys Phe Tyr Gly Leu Gln Val Thr Gly Lys Ala
65                  70                  75                  80

Asp Ala Asp Thr Met Lys Ala Met Arg Arg Pro Arg Cys Gly Val Pro
                85                  90                  95

Asp Lys Phe Gly Ala Glu Ile Lys Ala Asn Val Arg Arg Lys Arg Tyr
                100                 105                 110

Ala Ile Gln Gly Leu Lys Trp Gln His Asn Glu Ile Thr Phe Cys Ile
            115                 120                 125

Gln Asn Tyr Thr Pro Lys Val Gly Glu Tyr Ala Thr Tyr Glu Ala Ile
            130                 135                 140

Arg Lys Ala Phe Arg Val Trp Glu Ser Ala Thr Pro Leu Arg Phe Arg
145                 150                 155                 160

Glu Val Pro Tyr Ala Tyr Ile Arg Glu Gly His Glu Lys Gln Ala Asp
                165                 170                 175

Ile Met Ile Phe Phe Ala Glu Gly Phe His Gly Asp Ser Thr Pro Phe
            180                 185                 190

Asp Gly Glu Gly Gly Phe Leu Ala His Ala Tyr Phe Pro Gly Pro Asn
            195                 200                 205

Ile Gly Gly Asp Thr His Phe Asp Ser Ala Glu Pro Trp Thr Val Arg
            210                 215                 220

Asn Glu Asp Leu Asn Gly Asn Asp Ile Phe Leu Val Ala Val His Glu
225                 230                 235                 240

Leu Gly His Ala Leu Gly Leu Glu His Ser Ser Asp Pro Ser Ala Ile
                245                 250                 255

Met Ala Pro Phe Tyr Gln Trp Met Asp Thr Glu Asn Phe Val Leu Pro
                260                 265                 270

Asp Asp Asp Arg Arg Gly Ile Gln Gln Leu Tyr Gly Gly Glu Ser Gly
            275                 280                 285

Phe Pro Thr Lys Met Pro Pro Gln Pro Arg Thr Thr Ser Arg Pro Ser
            290                 295                 300

Val Pro Asp Lys Pro Lys Asn Pro Thr Tyr Gly Pro Asn Ile Cys Asp
305                 310                 315                 320

Gly Asn Phe Asp Thr Val Ala Met Leu Arg Gly Glu Met Phe Val Phe
```

```
                    325                 330                 335
Lys Glu Arg Trp Phe Trp Arg Val Arg Asn Asn Gln Val Met Asp Gly
                340                 345                 350
Tyr Pro Met Pro Ile Gly Gln Phe Trp Arg Gly Leu Pro Ala Ser Ile
            355                 360                 365
Asn Thr Ala Tyr Glu Arg Lys Asp Gly Lys Phe Val Phe Lys Gly
        370                 375                 380
Asp Lys His Trp Val Phe Asp Glu Ala Ser Leu Glu Pro Gly Tyr Pro
385                 390                 395                 400
Lys His Ile Lys Glu Leu Gly Arg Gly Leu Pro Thr Asp Lys Ile Asp
                405                 410                 415
Ala Ala Leu Phe Trp Met Pro Asn Gly Lys Thr Tyr Phe Phe Arg Gly
            420                 425                 430
Asn Lys Tyr Tyr Arg Phe Asn Glu Glu Leu Arg Ala Val Asp Ser Glu
        435                 440                 445
Tyr Pro Lys Asn Ile Lys Val Trp Glu Gly Ile Pro Glu Ser Pro Arg
    450                 455                 460
Gly Ser Phe Met Gly Ser Asp Glu Val Phe Thr Tyr Phe Tyr Lys Gly
465                 470                 475                 480
Asn Lys Tyr Trp Lys Phe Asn Asn Gln Lys Leu Lys Val Glu Pro Gly
                485                 490                 495
Tyr Pro Lys Ser Ala Leu Arg Asp Trp Met Gly Cys Pro Ser Gly Gly
            500                 505                 510
Arg Pro Asp Glu Gly Thr Glu Glu Thr Glu Val Ile Ile Ile Glu
        515                 520                 525
Val Asp Glu Glu Gly Gly Gly Ala Val Ser Ala Ala Ala Val Val Leu
    530                 535                 540
Pro Val Leu Leu Leu Leu Leu Val Leu Ala Val Gly Leu Ala Val Phe
545                 550                 555                 560
Phe Phe Arg Arg His Gly Thr Pro Arg Arg Leu Leu Tyr Cys Gln Arg
                565                 570                 575
Ser Leu Leu Asp Lys Val
            580

(2) INFORMATION FOR SEQ ID NO:10:

(i) SEQUENCE CHARACTERISTICS:
        (A) LENGTH: 607 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO:10:

Met Ile Leu Leu Thr Phe Ser Thr Gly Arg Arg Leu Asp Phe Val His
1               5                   10                  15

His Ser Gly Val Phe Phe Leu Gln Thr Leu Leu Trp Ile Leu Cys Ala
                20                  25                  30

Thr Val Cys Gly Thr Glu Gln Tyr Phe Asn Val Glu Val Trp Leu Gln
            35                  40                  45

Lys Tyr Gly Tyr Leu Pro Pro Thr Asp Pro Arg Met Ser Val Leu Arg
        50                  55                  60

Ser Ala Glu Thr Met Gln Ser Ala Leu Ala Ala Met Gln Gln Phe Tyr
65                  70                  75                  80

Gly Ile Asn Met Thr Gly Lys Val Asp Arg Asn Thr Ile Asp Trp Met
```

```
                    85                  90                  95
Lys Lys Pro Arg Cys Gly Val Pro Asp Gln Thr Arg Gly Ser Ser Lys
                100                 105                 110
Phe His Ile Arg Arg Lys Arg Tyr Ala Leu Thr Gly Gln Lys Trp Gln
            115                 120                 125
His Lys His Ile Thr Tyr Ser Ile Lys Asn Val Thr Pro Lys Val Gly
        130                 135                 140
Asp Pro Glu Thr Arg Lys Ala Ile Arg Arg Ala Phe Asp Val Trp Gln
145                 150                 155                 160
Asn Val Thr Pro Leu Thr Phe Glu Glu Val Pro Tyr Ser Glu Leu Glu
                165                 170                 175
Asn Gly Lys Arg Asp Val Asp Ile Thr Ile Ile Phe Ala Ser Gly Phe
            180                 185                 190
His Gly Asp Ser Ser Pro Phe Asp Gly Glu Gly Gly Phe Leu Ala His
        195                 200                 205
Ala Tyr Phe Pro Gly Pro Gly Ile Gly Gly Asp Thr His Phe Asp Ser
210                 215                 220
Asp Glu Pro Trp Thr Leu Gly Asn Pro Asn His Asp Gly Asn Asp Leu
225                 230                 235                 240
Phe Leu Val Ala Val His Glu Leu Gly His Ala Leu Gly Leu Glu His
                245                 250                 255
Ser Asn Asp Pro Thr Ala Ile Met Ala Pro Phe Tyr Gln Tyr Met Glu
            260                 265                 270
Thr Asp Asn Phe Lys Leu Pro Asn Asp Asp Leu Gln Gly Ile Gln Lys
        275                 280                 285
Ile Tyr Gly Pro Pro Asp Lys Ile Pro Pro Thr Arg Pro Leu Pro
        290                 295                 300
Thr Val Pro Pro His Arg Ser Ile Pro Ala Asp Pro Arg Lys Asn
305                 310                 315                 320
Asp Arg Pro Lys Pro Arg Pro Pro Thr Gly Arg Pro Ser Tyr Pro
                325                 330                 335
Gly Ala Lys Pro Asn Ile Cys Asp Gly Asn Phe Asn Thr Leu Ala Ile
            340                 345                 350
Leu Arg Arg Glu Met Phe Val Phe Lys Asp Gln Trp Phe Trp Arg Val
        355                 360                 365
Arg Asn Asn Arg Val Met Asp Gly Tyr Pro Met Gln Ile Thr Tyr Phe
    370                 375                 380
Trp Arg Gly Leu Pro Pro Ser Ile Asp Ala Val Tyr Glu Asn Ser Asp
385                 390                 395                 400
Gly Asn Phe Val Phe Phe Lys Gly Asn Lys Tyr Trp Val Phe Lys Asp
                405                 410                 415
Thr Thr Leu Gln Pro Gly Tyr Pro His Asp Leu Ile Thr Leu Gly Ser
            420                 425                 430
Gly Ile Pro Pro His Gly Ile Asp Ser Ala Ile Trp Trp Glu Asp Val
        435                 440                 445
Gly Lys Thr Tyr Phe Phe Lys Gly Asp Arg Tyr Trp Arg Tyr Ser Glu
    450                 455                 460
Glu Met Lys Thr Met Asp Pro Gly Tyr Pro Lys Pro Ile Thr Val Trp
465                 470                 475                 480
Lys Gly Ile Pro Glu Ser Pro Gln Gly Ala Phe Val His Lys Glu Asn
                485                 490                 495
Gly Phe Thr Tyr Phe Tyr Lys Gly Lys Glu Tyr Trp Lys Phe Asn Asn
            500                 505                 510
```

```
Gln Ile Leu Lys Val Glu Pro Gly Tyr Pro Arg Ser Ile Leu Lys Asp
        515                 520                 525
Phe Met Gly Cys Asp Gly Pro Thr Asp Arg Val Lys Glu Gly His Ser
    530                 535                 540
Pro Pro Asp Asp Val Asp Ile Val Ile Lys Leu Asp Asn Thr Ala Ser
545                 550                 555                 560
Thr Val Lys Ala Ile Ala Ile Val Ile Pro Cys Ile Leu Ala Leu Cys
                565             570                     575
Leu Leu Val Leu Val Tyr Thr Val Phe Gln Phe Lys Arg Lys Gly Thr
            580                 585                 590
Pro Arg His Ile Leu Tyr Cys Lys Arg Ser Met Gln Glu Trp Val
        595             600                 605
```